US011034933B2

(12) United States Patent
Yang et al.

(10) Patent No.: US 11,034,933 B2
(45) Date of Patent: Jun. 15, 2021

(54) METHODS FOR SELECTIVELY EXPANDING AND ENRICHING CELLS TRANSDUCED WITH CHIMERIC ANTIGEN RECEPTORS AND TREATING HIV INFECTION

(71) Applicant: The Regents of the University of California, Oakland, CA (US)

(72) Inventors: Otto O. Yang, Los Angeles, CA (US); Ayub Ali, Porter Ranch, CA (US); Hwee Ng, Los Angeles, CA (US); Scott G. Kitchen, Los Angeles, CA (US); Jerome A. Zack, Tarzana, CA (US); Irvin Chen, Palos Verdes Estates, CA (US)

(73) Assignee: The Regents of the University of California, Oakland, CA (US)

( * ) Notice: Subject to any disclaimer, the term of this patent is extended or adjusted under 35 U.S.C. 154(b) by 249 days.

(21) Appl. No.: 16/070,745

(22) PCT Filed: Jan. 27, 2017

(86) PCT No.: PCT/US2017/015388
§ 371 (c)(1),
(2) Date: Jul. 17, 2018

(87) PCT Pub. No.: WO2017/132535
PCT Pub. Date: Aug. 3, 2017

(65) Prior Publication Data
US 2019/0024049 A1    Jan. 24, 2019

Related U.S. Application Data

(60) Provisional application No. 62/287,928, filed on Jan. 28, 2016.

(51) Int. Cl.
| | |
|---|---|
| *C12N 5/0783* | (2010.01) |
| *A61K 39/21* | (2006.01) |
| *C07K 14/705* | (2006.01) |
| *C07K 14/725* | (2006.01) |
| *C07K 16/28* | (2006.01) |
| *C07K 16/10* | (2006.01) |
| *A61K 35/17* | (2015.01) |
| *C07K 16/42* | (2006.01) |
| *A61P 31/18* | (2006.01) |
| *A61K 39/00* | (2006.01) |

(52) U.S. Cl.
CPC ............ *C12N 5/0638* (2013.01); *A61K 35/17* (2013.01); *A61K 39/21* (2013.01); *A61P 31/18* (2018.01); *C07K 14/7051* (2013.01); *C07K 14/70517* (2013.01); *C07K 14/70578* (2013.01); *C07K 16/1045* (2013.01); *C07K 16/2863* (2013.01); *C07K 16/42* (2013.01); *C12N 5/0636* (2013.01); *A61K 2039/5156* (2013.01); *A61K 2039/5158* (2013.01); *C07K 2317/53* (2013.01); *C07K 2317/55* (2013.01);

*C07K 2317/622* (2013.01); *C07K 2319/00* (2013.01); *C07K 2319/02* (2013.01); *C07K 2319/03* (2013.01); *C12N 2501/2302* (2013.01); *C12N 2501/515* (2013.01); *C12N 2501/998* (2013.01); *C12N 2510/00* (2013.01)

(58) Field of Classification Search
None
See application file for complete search history.

(56) References Cited

U.S. PATENT DOCUMENTS

| 10,246,505 B2 * | 4/2019 | Berger ............ C07K 14/70564 |
|---|---|---|
| 10,273,300 B2 | 4/2019 | Bedoya et al. |
| 2007/0248951 A1 | 10/2007 | Yagasaki et al. |
| 2014/0322216 A1 | 10/2014 | Kaplan |

FOREIGN PATENT DOCUMENTS

| WO | 2015017755 A1 | 2/2015 |
|---|---|---|
| WO | 2015095895 A1 | 6/2015 |
| WO | 2015164594 A1 | 10/2015 |

OTHER PUBLICATIONS

"ATCC® Animal Cell Culture Guide: tips and techniques for continuous cell lines", Authors unknown, Published by American Type Culture Collection, Manassas, VA, USA, at https://www.atcc.org/~/media/PDFs/Culture%20Guides/AnimCellCulture_Guide.ashx, published 2014, 39 pages, hereinafter "ATCC Guide". (Year: 2014).*
International Search Report received in PCT/US2017/015388 dated Apr. 17, 2017.
Written Opinion received in PCT/US2017/015388 dated Apr. 17, 2017.
Cartellieri, et al., "A Novel Ex Vivo Isolation and Expansion Procedure for Chimeric Antigen Receptor Engrafted Human T Cells", Apr. 3, 2014, p. e93745, vol. 9, No. 4, Publisher: PLoS One.
Edl, et al., "Assays for selection of single-chain fragment variable recombinant antibodies to metal nanoclusters", 2005, pp. 113-120, vol. 303, Publisher: Methods Mol Biol.
Feldhaus, et al., "Flow-cytometric isolation of human antibodies from a nonimmune *Saccharomyces cerevisiae* surface display library", Feb. 1, 2003, pp. 163-170, vol. 21, No. 2, Publisher: Nature Biotechnology.
Liu, et al., "Novel CD4-Based Bispecific Chimeric Antigen Receptor Designed for Enhanced Anti-HIV Potency and Absence of HIV Entry Receptor Activity", Jul. 1, 2015, pp. 6685-6694, vol. 89, No. 13, Publisher: Journal of Virology.

(Continued)

*Primary Examiner* — Robert M Kelly
(74) *Attorney, Agent, or Firm* — Suzannah K. Sundby, Esq.; Canady + Lortz LLP

(57) ABSTRACT

Disclosed herein are methods for selectively expanding cells expressing chimeric antigen receptors and enriching cells expressing chimeric antigen receptors in compositions and methods of treating HIV infection in subjects by administering the expanded and/or enriched cells.

12 Claims, 12 Drawing Sheets
Specification includes a Sequence Listing.

(56) References Cited

OTHER PUBLICATIONS

Trickett, et al., "T cell stimulation and expansion using anti-CD3/CD28 beads", Jan. 4, 2003, pp. 251-255, vol. 275, No. 1-2, Publisher: Journal of Immunological Meth.
Ali, et al., "HIV-1-Specific Chimeric Antigen Receptors Based on Broadly Neutralizing Antibodies", Jul. 11, 2016, pp. 6999-7006, vol. 90, No. 15, Publisher: J Virol.
Supplementary European Search report received in EP17744990 dated Aug. 6, 2019.
Guedan Et Alo., "ICOS-based chimeric antigen receptors program bipolar TH17/TH1 cells", Aug. 14, 2014, pp. 1070-1080, vol. 124, No. 7, Publisher: Blood.

* cited by examiner

METHODS FOR SELECTIVELY EXPANDING AND ENRICHING CELLS TRANSDUCED WITH CHIMERIC ANTIGEN RECEPTORS AND TREATING HIV INFECTION

REFERENCE TO A SEQUENCE LISTING SUBMITTED VIA EFS-WEB

The content of the ASCII text file of the sequence listing named "20170127_034044_163WO1_ST25" which is 81.7 kb in size was created on Jan. 25, 2017, and electronically submitted via EFS-Web herewith the application is incorporated herein by reference in its entirety.

BACKGROUND OF THE INVENTION

1. Field of the Invention

The present invention generally relates to expanding and enriching cells transduced with chimeric antigen receptors.

2. Description of the Related Art

Chimeric Antigen Receptors (CARs) are artificial T cell receptors (TCRs). CARs generally comprise an extracellular domain coupled to an intracellular signaling domain comprising a CD3 zeta chain. The extracellular domain binds a target ligand (e.g., a tumor antigen) on target cells (e.g., tumor cells). When the extracellular domain binds its target ligand, the intracellular signaling domain comprising the CD3 zeta chain produces a TCR signal that triggers the cell expressing the CAR to kill the target cell. Most CARs comprise, as the extracellular domain, a single chain antibody (SCA) that specifically binds the target ligand.

A key problem with using CARs for gene therapies (and gene therapies in general) is the relatively low transduction efficiency of the cells. Achieving high efficiency transduction is often difficult. For example, the transduction efficiency of peripheral blood T cells is usually less than 50% and often around 10-20%. A conventional prior art method for addressing the low transduction efficiency is to start with huge numbers of cells so that the final number of transduced cells is sufficient. This method, however, is costly and results in a relatively significant loss of transduced cells when the transduced cells are separated from the non-transduced cells.

SUMMARY OF THE INVENTION

In some embodiments, the present invention provides a method of expanding cells expressing a chimeric antigen receptor (CAR), which comprises contacting the cells with an antibody against the CAR while culturing the cells. In some embodiments, the antibody specifically binds the CAR. In some embodiments, the CAR specifically binds an HIV antigen. In some embodiments, the HIV antigen is an HIV-1 antigen. In some embodiments, the HIV antigen is an HIV envelope protein or a portion thereof. In some embodiments, the HIV antigen is gp120 or a portion thereof. In some embodiments the HIV antigen is the CD4 binding site on gp120. In some embodiments, the HIV antigen is the CD4-induced binding site on gp120. In some embodiments, the HIV antigen is the N-glycan on gp120. In some embodiments, the HIV antigen is the V2 of gp120. In some embodiments, the HIV antigen is the membrane proximal region on gp41. In some embodiments, the antibody binds the CAR with a higher binding affinity than any endogenous T cell receptors expressed by the cells. In some embodiments, the CAR comprises a single chain antibody domain (SCA) and the antibody binds the SCA. In some embodiments, the antibody is an anti-human $F_{ab}$ antibody. In some embodiments, the antibody is a non-human antibody, such as a goat, pig, rat, mouse, or the like. In some embodiments, the antibody is a chimeric antibody. In some embodiments, the antibody is a recombinantly produced antibody. In some embodiments, the antibody is an anti-IgG antibody. In some embodiments, the cells are cultured for at least one cell passage. In some embodiments, the cells are cultured for two or more cell passages. In some embodiments, the cells are T cells. In some embodiments, the T cells are $CD8^+$ T cells.

In some embodiments, the present invention provides a method of enriching cells expressing a chimeric antigen receptor (CAR) over cells not expressing the CAR in a composition, which comprises contacting the cells with an antibody against the CAR while culturing the cells. In some embodiments, the cells expressing the CAR are cells transduced with a nucleic acid molecule encoding the CAR. In some embodiments, the cells expressing the CAR are clones of the cells transduced with a nucleic acid molecule encoding the CAR that express the CAR. In some embodiments, the antibody specifically binds the CAR. In some embodiments, the CAR specifically binds an HIV antigen. In some embodiments, the HIV antigen is an HIV-1 antigen. In some embodiments, the HIV antigen is an HIV envelope protein or a portion thereof. In some embodiments, the HIV antigen is gp120 or a portion thereof. In some embodiments the HIV antigen is the CD4 binding site on gp120. In some embodiments, the HIV antigen is the CD4-induced binding site on gp120. In some embodiments, the HIV antigen is the N-glycan on gp120. In some embodiments, the HIV antigen is the V2 of gp120. In some embodiments, the HIV antigen is the membrane proximal region on gp41. In some embodiments, the antibody binds the CAR with a higher binding affinity than any endogenous T cell receptors expressed by the cells. In some embodiments, the CAR comprises a single chain antibody domain (SCA) and the antibody binds the SCA. In some embodiments, the antibody is an anti-human $F_{ab}$ antibody. In some embodiments, the antibody is a non-human antibody, such as a goat, pig, rat, mouse, or the like. In some embodiments, the antibody is a chimeric antibody. In some embodiments, the antibody is a recombinantly produced antibody. In some embodiments, the antibody is an anti-IgG antibody. In some embodiments, the cells are cultured for at least one cell passage. In some embodiments, the cells are cultured for two or more cell passages. In some embodiments, the cells are T cells. In some embodiments, the T cells are $CD8^+$ T cells.

In some embodiments, the present invention provides a composition comprising, consisting essentially of, or consisting of one or more cells expressing one or more CARs that have been expanded and/or enriched according to one or more of the methods of the present invention. As used herein, a composition "comprising" one or more cells expressing one or more CARs that have been expanded and/or enriched according to one or more of the methods of the present invention, may contain other compounds and cells. As used herein, a composition "consisting essentially of" one or more cells expressing one or more CARs that have been expanded and/or enriched according to one or more of the methods of the present invention may comprise other compounds and cells so long as they do not materially change the activity or function of the cells expressing the one or more CARs in the composition. As used herein, a composition "consisting of" one or more cells expressing one or more CARs that have been expanded and/or enriched according to one or more of the methods of the present invention means that the composition does not contain other functional cells in addition to the one or more cells expressing one or more CARs. Compositions consisting of one or more cells expressing one or more CARs that have been expanded and/or enriched according to one or more of the methods of the present invention may comprise ingredients other than cells, e.g., compounds, proteins, pharmaceutically acceptable carriers, surfactants, preservatives, etc. In some embodiments, compositions consisting of one or more cells expressing one or more CARs that have been expanded and/or enriched according to one or more of the methods of the present invention may contain insignificant amounts of contaminants. In some embodiments, the amount of the one or more cells expressing one or more CARs is at least about 50% of the total cells in the composition. In some embodiments, the amount of the one or more cells expressing one or more CARs is at least about 60% of the total cells in the composition. In some embodiments, the amount of the one or more cells expressing one or more CARs is at least about 70% of the total cells in the composition. In some embodiments, the amount of the one or more cells expressing one or more CARs is at least about 80% of the total cells in the composition. In some embodiments, the amount of the one or more cells expressing one or more CARs is at least about 90% of the total cells in the composition. In some embodiments, the amount of the one or more cells expressing one or more CARs is at least about 95% of the total cells in the composition. In some embodiments, the compositions according to the present invention comprise a therapeutically effective amount of the one or more cells expressing one or more CARs.

In some embodiments, the present invention provides a method of treating an HIV infection in a subject which comprises administering to the subject a therapeutically effective amount of one or more cells expressing one or more CARs that have been expanded and/or enriched according to one or more of the methods of the present invention. In some embodiments, the one or more cells expressing one or more CARs are administered in the form of a composition according to the present invention.

In some embodiments, the CAR expressed by the cells comprises an amino acid sequence having at least 90%, preferably at least 95%, more preferably at least 97%, and most preferably 99-100% sequence identity to a sequence selected from the group consisting of SEQ ID NO:5, SEQ ID NO:8, SEQ ID NO:11, SEQ ID NO:14, SEQ ID NO:17, SEQ ID NO:20, and SEQ ID NO:23. In some embodiments, the CAR expressed by the cells comprises an amino acid sequence having at least 90%, preferably at least 95%, more preferably at least 97%, and most preferably 99-100% sequence identity to a sequence selected from the group consisting of SEQ ID NO:6, SEQ ID NO:9, SEQ ID NO:12, SEQ ID NO:15, SEQ ID NO:18, SEQ ID NO:21, and SEQ ID NO:24. In some embodiments, the CAR expressed by the cells comprises a first amino acid sequence having at least 90%, preferably at least 95%, more preferably at least 97%, and most preferably 99-100% sequence identity to a sequence selected from the group consisting of SEQ ID NO:5, SEQ ID NO:8, SEQ ID NO:11, SEQ ID NO:14, SEQ ID NO:17, SEQ ID NO:20, and SEQ ID NO:23; and a second amino acid sequence having at least 90%, preferably at least 95%, more preferably at least 97%, and most preferably 99-100% sequence identity to a sequence selected from the group consisting of SEQ ID NO:6, SEQ ID NO:9, SEQ ID NO:12, SEQ ID NO:15, SEQ ID NO:18, SEQ ID NO:21, and SEQ ID NO:24. In some embodiments, the CAR expressed by the cells comprises an amino acid sequence having at least 90%, preferably at least 95%, more preferably at least 97%, and most preferably 99-100% sequence identity to a sequence selected from the group consisting of SEQ ID NO:4, SEQ ID NO:7, SEQ ID NO:10, SEQ ID NO:13, SEQ ID NO:16, SEQ ID NO:19, and SEQ ID NO:22. In some embodiments, the CAR expressed by the cells is encoded by a nucleic acid sequence having at least 90%, preferably at least 95%, more preferably at least 97%, and most preferably 99-100% sequence identity to a sequence selected from the group consisting of SEQ ID NO:25, SEQ ID NO:26, SEQ ID NO:27, SEQ ID NO:28, SEQ ID NO:29, SEQ ID NO:30, and SEQ ID NO:31.

Both the foregoing general description and the following detailed description are exemplary and explanatory only and are intended to provide further explanation of the invention as claimed. The accompanying drawings are included to provide a further understanding of the invention and are incorporated in and constitute part of this specification, illustrate several embodiments of the invention, and together with the description serve to explain the principles of the invention.

DESCRIPTION OF THE DRAWINGS

This invention is further understood by reference to the drawings wherein:

In FIG. 8, the initial order of the CAR-SCAs from top to bottom is PGT128, 10E8, VRC01, 3BNC117, X5 and PGT127 (same initial starting amount), and PG9. The order of the CAR-SCAs from top to bottom at Passage 2 is PGT126, VRC01, PGT128, X5, 10E8, 3BNC117, and PG9.

In FIG. 9, the order of the CAR-SCAs at Passage 2 from top to bottom is PG9, PGT126, PGT128, VRC01, 10E8, and 3BNC117.

DETAILED DESCRIPTION OF THE INVENTION

Figure 1:
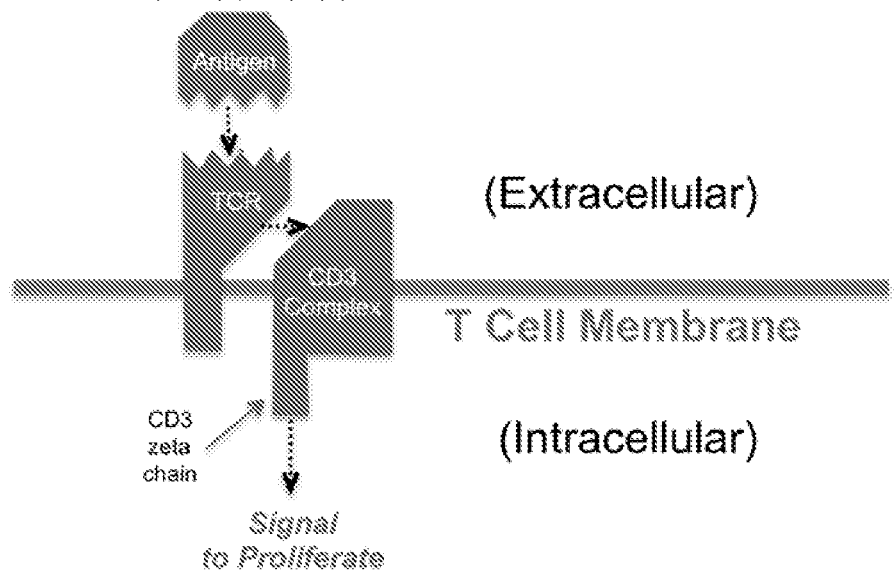
FIG. 1 schematically shows a T cell is specifically expanded if the TCR binds only a specific antigen (typically a small foreign peptide bound by a major histocompatibility complex). Binding of the antigen to the TCR triggers a change in the CD3 complex that sends a signal through the zeta chain for the cell to proliferate.
Figure 2:
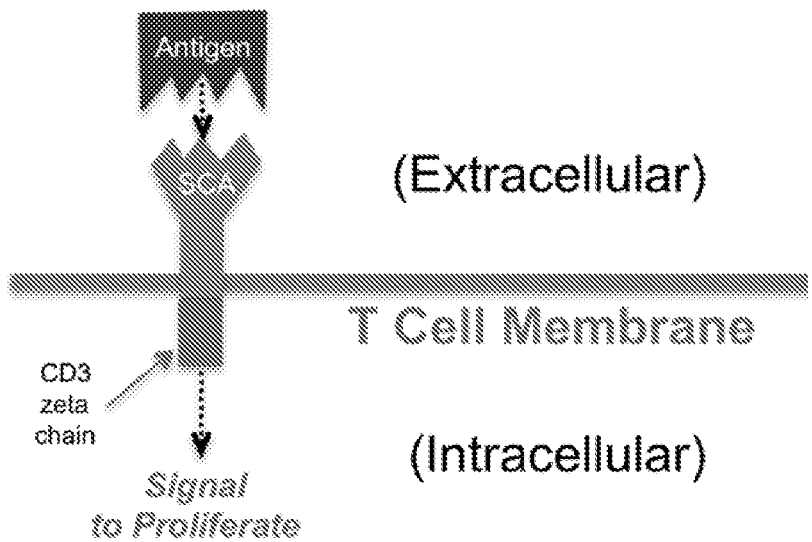
FIG. 2 schematically shows the expansion of a cell expressing a CAR with a single chain antibody (SCA) domain fused to the zeta chain of CD3 by antigen binding to the SCA of the CAR-SCA.
Figure 3:
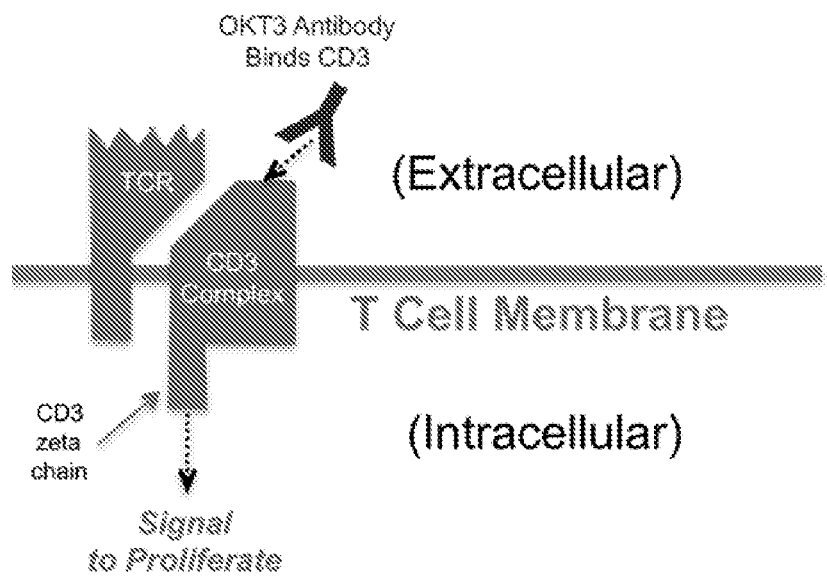
FIG. 3 schematically shows the in vitro expansion of T cells through directly triggering the CD3 complex by binding it with a monoclonal antibody such as OKT3, thereby triggering a signal through the CD3 zeta chain.

Cells expressing a native T cell receptor (TCR) can be expanded by antigen binding, i.e., binding the TCR with the antigen it specifically binds. FIG. 1 schematically shows antigen binding to a TCR results in a signal for the cell to proliferate. Binding of the antigen to the TCR triggers a change in the CD3 complex that sends a signal through the zeta chain for the cell to proliferate. Similarly, cells expressing CARs can be expanded by antigen binding as schematically shown in FIG. 2. As schematically shown in FIG. 3, cells expressing TCRs can be expanded by directly triggering the CD3 complex by binding it with a monoclonal antibody, such as OKT3, which triggers the signal to proliferate through the CD3 zeta chain. Alternatively, a lectin such as phytohemagglutinin, with or without an ionophore like ionomycin, can be used to elicit the downstream activators from CD3 zeta signaling.

While using an antigen to selectively expand cells expressing a CAR could be an approach to selectively expand CAR-transduced cells, this is problematic because CARs are generally designed to recognize cell surface target antigens, and thus whole cells with the appropriate target antigen would need to be used. This is not generally practical since adding non-autologous cells may pose additional risk of transmitting infectious agents or unwanted genes. Also, non-autologous cells will cause unwanted expansion of non-CAR-transduced cells that are allo-specific.

Therefore, in some embodiments, the present invention provides methods for selectively expanding and enriching cells expressing a chimeric antigen receptor having a single chain antibody domain (CAR-SCA) over cells that do not express the CAR-SCA by contacting the cells with an antibody that specifically binds the CAR-SCA. In some embodiments, the antibody specifically binds the CAR-SCA, but does not bind any endogenous TCRs expressed by the non-transduced cells. In some embodiments, the antibody has a higher binding affinity for the CAR-SCA as compared to any endogenous TCRs. In some embodiments, the antibody specifically binds the SCA domain of the CAR-SCA.

Figure 4:
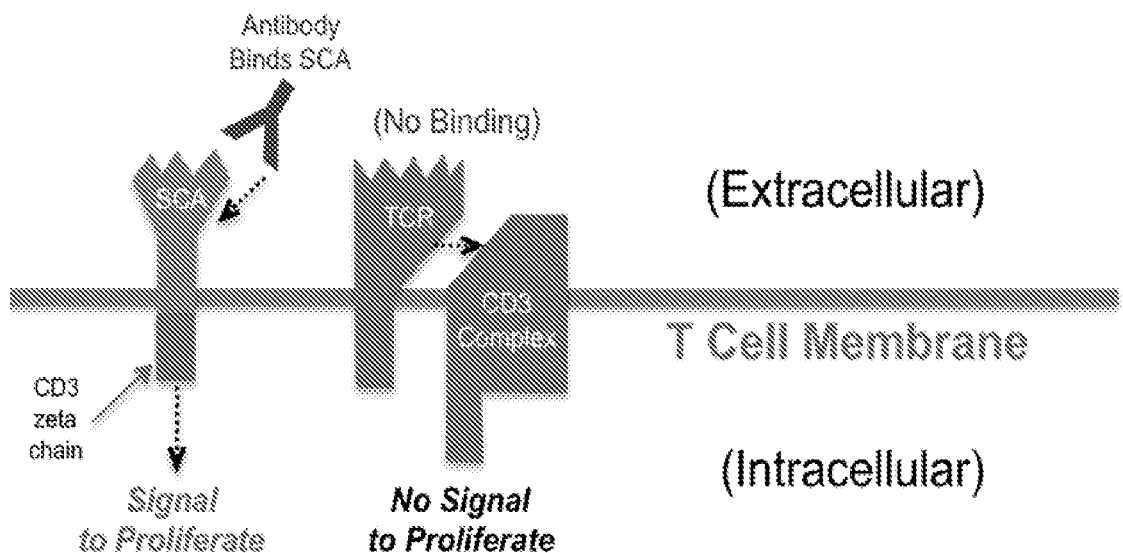
FIG. 4 schematically shows a method according to the present invention, e.g., binding the SCA with an antibody that specifically binds the CAR-SCA but not the native TCR or CD3 complex.

FIG. 4 schematically shows antibody binding to a CAR-SCA to result in a signal for cell proliferation and the lack antibody binding to the TCR and hence a lack of a cell proliferation signal from the TCR. As generally referred to herein, CARs having SCAs are referenced as "CAR-SCAs" and CAR-SCAs having a specific SCA and cell lines expressing such are referenced by the specific SCA, e.g., "CAR-10E8" or "10E8".

Figure 5:
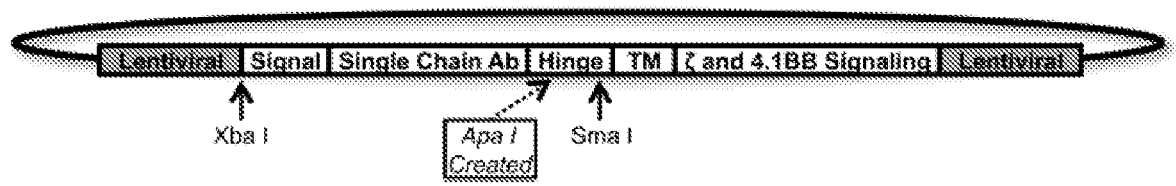
FIG. 5 schematically shows construction of a CAR-SCA construct. The parental vector contained a CAR based on a single chain antibody. This vector was modified with a silent mutation to create an Apa I site in the hinge region of the CAR gene (within a sequence confirmed Xba I-Sma I intermediate plasmid vector). One construct was generated for each version with different signaling domains (CD28-ζ 4-1BB-ζ and ζ). CAR-SCA constructs were generated by synthesis of single chain antibody and partial hinge DNA sequences that were substituted into this vector via Xba I-Apa I restriction fragments.

CAR constructs as described in WO 2015/017755, which is herein incorporated by reference in its entirety, were used to transduce a population of T cells using transduction methods known in the art. Specifically, a set of broadly neutralizing antibodies (bnAbs) against HIV-1 was selected based on binding of different HIV-1 Env domains and availability of sequences. These included seven antibodies targeting the CD4 binding site, the CD4 binding-induced site on gp120, the gp120 V2 loop, gp120 N-glycans, and the membrane proximal region of gp41. As set forth in Example 1, genes for single chain versions of each antibody were created by synthesis of codon-optimized sequences for the heavy and light chains, separated by a linker (SEQ ID NO:2), and these genes were substituted for the single chain antibody in a second generation CAR vector containing the 4-1BB signaling domain fused to the CD3 signaling domain (FIG. 5).

Figure 6:
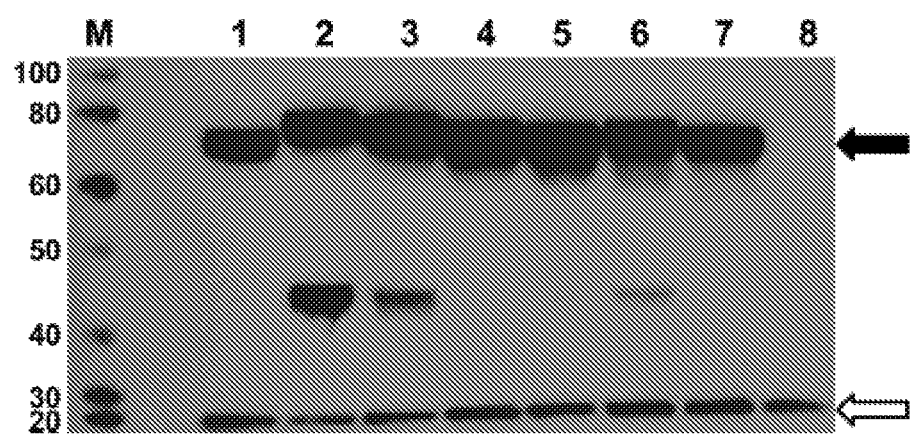
FIG. 6 is a picture of a Western blot confirming CAR-SCA expression of transduced Jurkat cells. Western blotting for CD3 ζ was performed on Jurkat cells after transduction with expression lentiviral vectors encoding CAR-SCAs. The open arrow indicates the expected size of the native CD3 ζ chain, and the closed arrow indicates the approximate expected size of the CAR-SCA (including the single chain antibody, hinge, 4-1BB signaling, and CD3 ζ signaling domains). Lane M: Marker; Lanes 1-8: CAR-10E8, CAR- 3BN117, CAR-PG9, CAR-PGT126, CAR-PGT128, CAR-VRC01, CAR-X5, and non-transduced Jurkat control, respectively.

Jurkat cells and primary human CD8$^+$ T cells were transduced with CAR-SCAs as set forth in Example 2. The CAR constructs were delivered by lentiviral vectors to Jurkat cells for initial confirmation of expression and functionality of the CAR-SCAs. Western blotting for CD3 ζ confirmed that the transduced cells contained both native CD3 ζ and the expected larger CD3 ζ-containing CAR for all seven constructs (FIG. 6). After transduction, the cells expressing the CAR-SCAs were selectively expanded and enriched by exposing the T cell populations to 400 ng/ml of goat anti-human IgG-F(ab)$_2$ antibodies in supplemented RPMI 1640 medium as described in Example 3. After culturing for 7 days, the T cell populations were stained with an anti-human IgG antibody having a fluorescent label.

Figure 7:
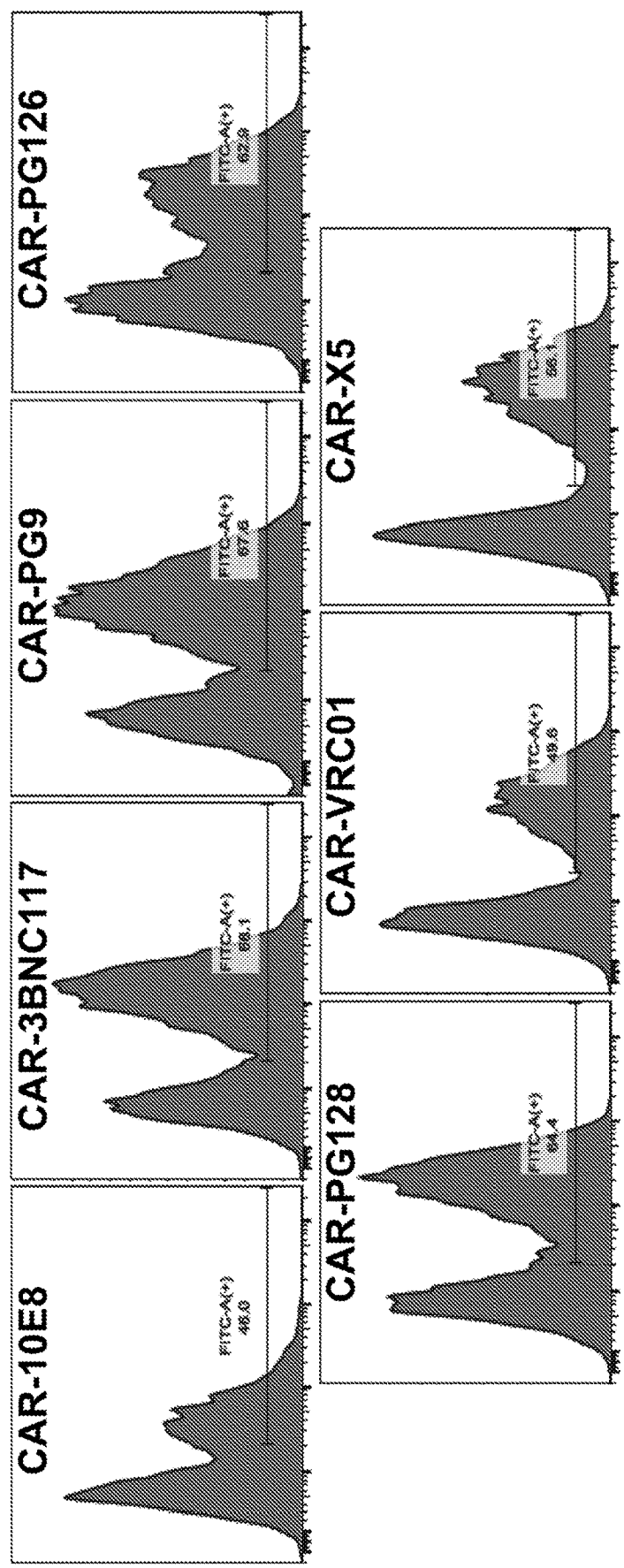
FIG. 7 shows histograms from flow cytometry of CAR-SCA transduced T cells stained with a fluorescent goat anti-human $F_{ab}$ antibody that specifically binds the CAR-SCAs. The stained histograms for 7 different CAR-SCAs show distinct populations of nontransduced and transduced T cells (about 50% each for all 7 CAR-SCAs).

FIG. 7 are stained histograms from flow cytometry showing distinct populations of about 50% non-transduced cells and about 50% cells expressing the CAR-SCAs for all 7 CAR constructs. Assuming an initial transduction efficiency of around 10-20%, enrichment methods according to the present invention result in selective expansion and enrichment of cells transduced with CAR-SCAs. As evidenced by the data provided in FIG. 7, the exemplary protocol resulted in selective expansion of cells expressing the CAR-SCAs by about 2.5 to about 5 times and an enrichment of cells expressing the CAR-SCAs by about 25% to about 40%.

Figure 8:
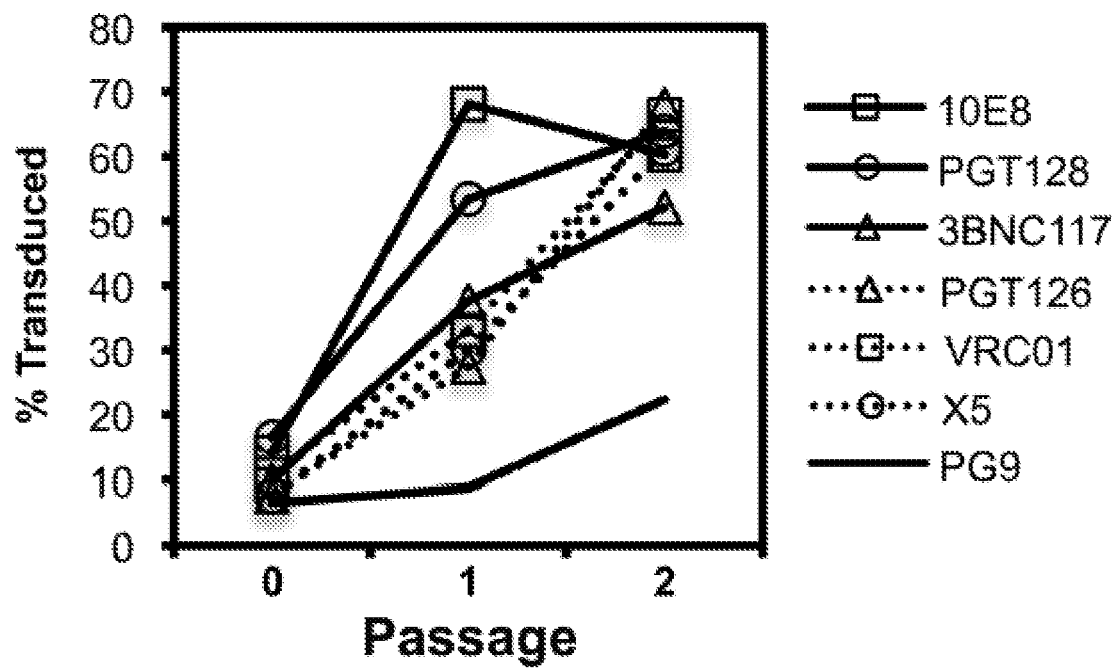
FIG. 8 are graphs showing the enrichment of CAR-SCA transduced primary CD8+ T lymphocytes through receptor-specific stimulation. After transduction of primary CD8+ T lymphocytes with each of the seven CAR-SCA vectors, the cells were restimulated twice using anti-Human $F_{ab}$ antibody with irradiated allogeneic feeder PBMC and IL-2. Each passage was about 10 days. The percentage of cells determined to express CAR-SCA was determined by flow cytometry as in FIG. 7.
Figure 9:
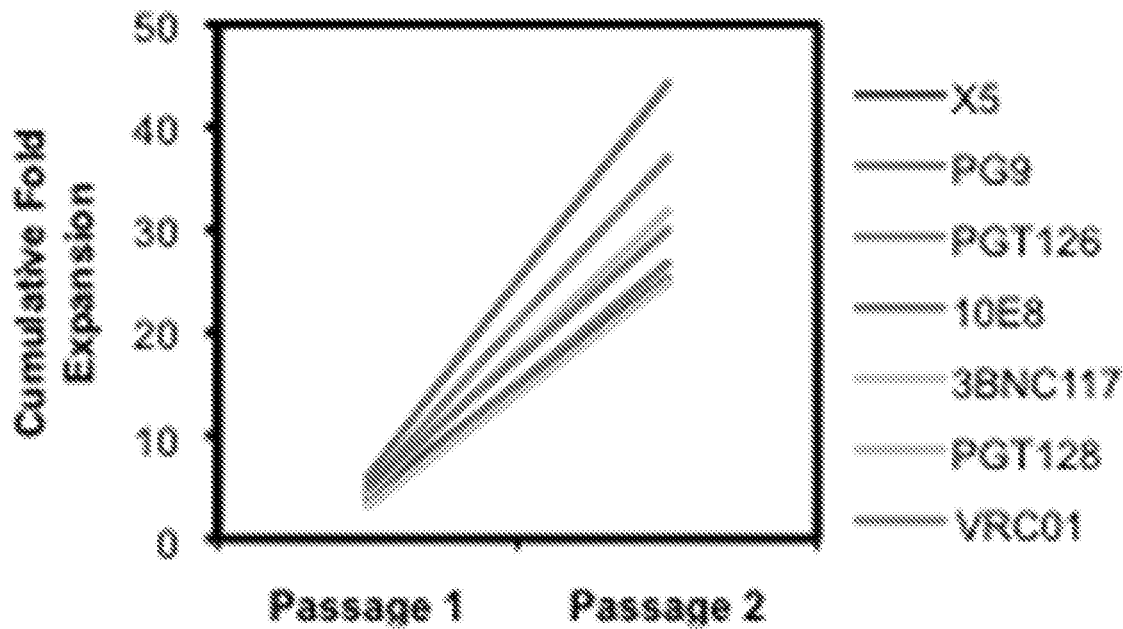
FIG. 9 graphically summarizes the cumulative fold expansion of CAR-SCA transduced primary CD8+ T lymphocytes through receptor-specific stimulation. For the cell stimulations shown in FIG. 8, the fold expansions for the two passages are plotted. Controls with CAR non-transduced cells show no expansion with $F_{ab}$ stimulation and similar levels of expansion using anti-CD3 antibody stimulation (not shown).
Figure 10:
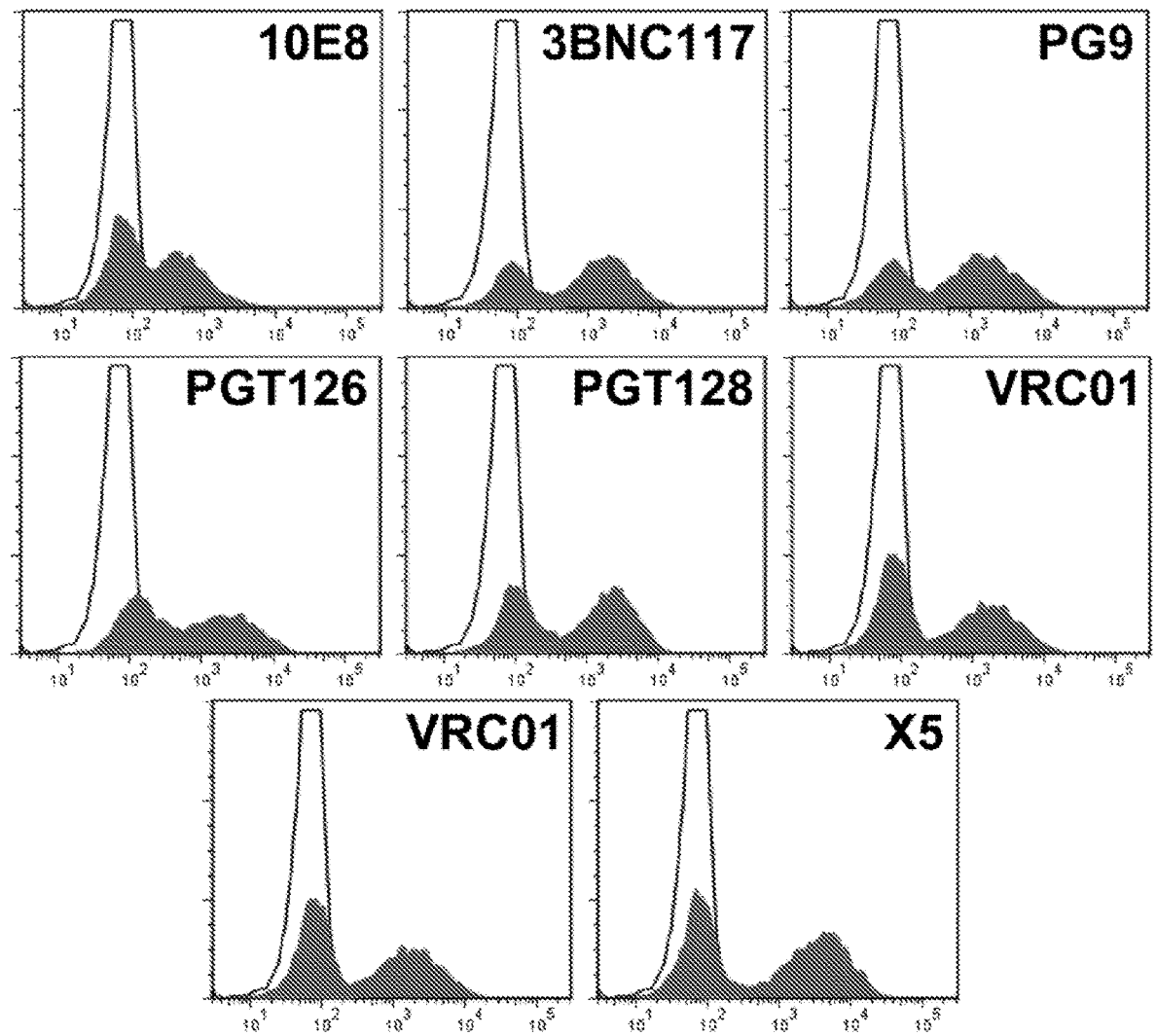
FIG. 10 are graphs summarizing data confirming CAR-SCA expression via flow cytometry for cell surface immunoglobulin of transduced Jurkat cells. Transduced Jurkat cells were stained with goat antibody against-Human $F_{ab}$ and assessed by flow cytometry. Histogram negative gating was set on non-transduced control cells (not shown).

Primary CD8$^+$ T lymphocytes were also transduced with the lentiviral vectors, and flow cytometry also confirmed cell surface expression of CAR-SCA for each CAR construct, although the transduction efficiency was lower than for Jurkat cells. Using the goat anti-human F$_{ab}$ antibody as a stimulus, there was selective expansion and enrichment of CAR-SCA transduced cells within the bulk population (FIG. 8), indicating that cross-linking of CARs induced proliferation of the transduced cells analogous to anti-CD3 antibody induced proliferation of normal T lymphocytes. As shown in FIG. 8, when starting with a relatively low starting transduction rate, just two cell passages and stimulation with antibody that specifically binds the CAR-SCAs result in a selective expansion that is greater than 5 times and an enrichment that is greater than 40% of cells expressing the CAR-SCAs. FIG. 9 shows the cumulative fold expansion by antibody stimulation as disclosed herein of primary CD8$^+$ T lymphocytes transduced with CAR-SCA. Flow cytometry for cell surface CAR-SCA expression using a goat antibody against human F$_{ab}$ (antigen-binding antibody fragment) further demonstrated cell surface expression of each CAR-SCA (FIG. 10).

CAR-SCA Transduced Primary CD8+T Lymphocytes Proliferated in Response to HIV-1-Infected Cells The compositions comprising the cells expressing the CAR-SCAs were tested for their activity against their antigenic target in accordance with Example 4. As an example, T1-CCR5 cells were infected with HIV virus strains NL4-3, 873, and 33931N at multiplicity of infection 10-1 TCID$_{50}$/cell and cultured with CD8$^+$ T cells transduced with CAR-10E8 as the exemplary CAR-SCA (>90% enriched, effector:target ratio of 1:4) and non-transduced CD8$^+$ T cells. The cells transduced with CAR-10E8 were expanded and enriched to >90% purity.

Additional experiments, as described in Example 4, were performed to test the capacity of expanded and enriched CAR-SCA transduced (≥90%) primary CD8$^+$ T lymphocyte effector cells to proliferate in response to HIV-1-infected cells. Generally, CD8$^+$ T lymphocytes transduced with the panel of CARs expanded and enriched to >90% purity by multiple rounds of anti-F$_{ab}$ stimulation (except CD4, a control HIV-1-specific CAR) were labeled with CellTrace Violet and co-cultured with irradiated HIV-1 NL4-3-infected T2 cells (which are MHC-I low, minimizing mixed lymphocyte reactions). CellTrace Violet fluorescence was assessed by flow cytometry after 7 days.

Figure 11:
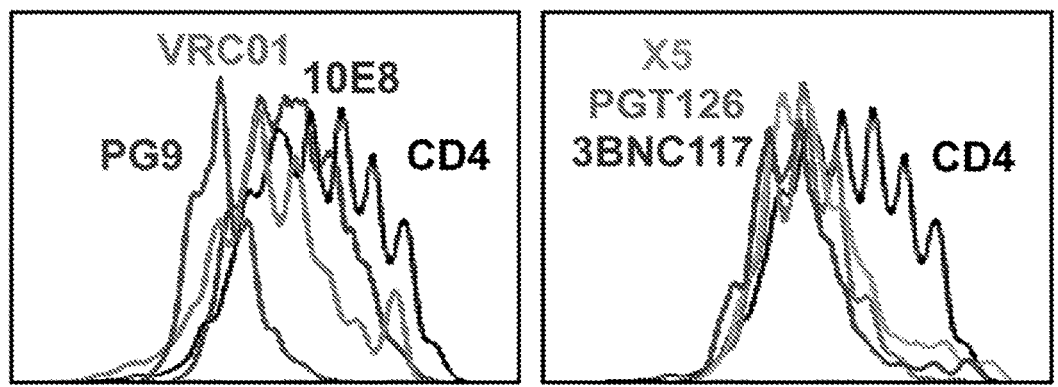
FIG. 11 graphically shows the proliferative capacity of anti-$F_{ab}$-enriched CAR-SCA transduced CD8+ T lymphocytes in response to HIV-1-infected cells. CD8+ T lymphocytes transduced with the panel of CAR-SCAs enriched to >90% purity by multiple rounds of anti-$F_{ab}$ stimulation (except CD4, a control HIV-1-specific CAR) were labeled with CellTrace Violet and co-cultured with irradiated HIV-1 NL4-3-infected T2 cells (which are MHC-I low, minimizing mixed lymphocyte reactions). CellTrace Violet fluorescence was assessed by flow cytometry after 7 days. The lines in the graph on the left are as follows: PG9 is the highest peak on the left, CD4 is the right most line, VRC01 is the line that starts the farthest left, and 10E8 has a peak that is higher than VRC01. In the graph on the right, the line for CD4 has a pattern that is the same as that in the graph on the left and the remaining lines from top to bottom under the highest peak for CD4 are as follows: X5, PGT126, and 3BNC117.
Figure 12:
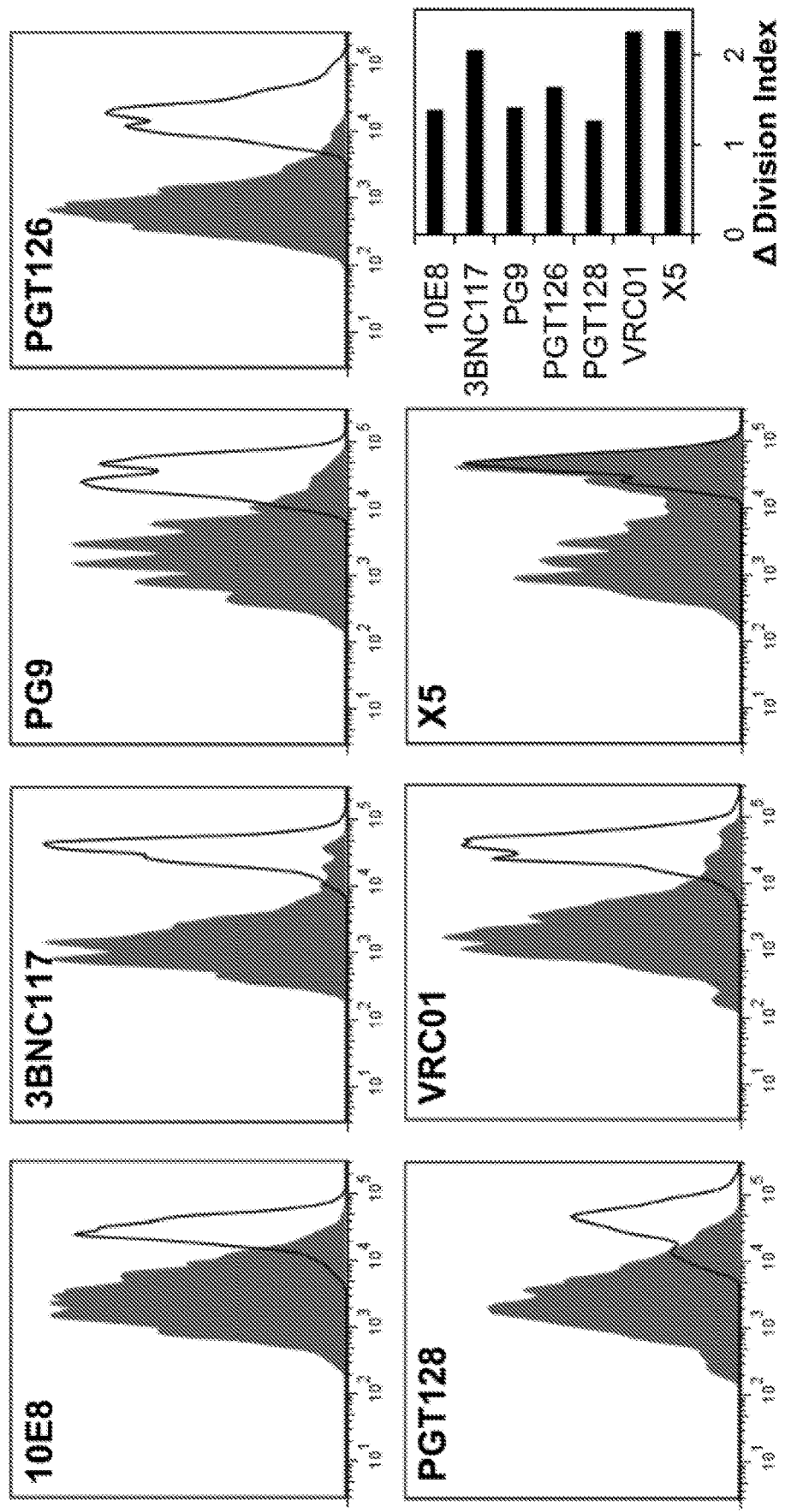
FIG. 12 are graphs showing proliferation mediated by CAR-SCA interaction with HIV-1-infected target cells. Primary CD8+ T lymphocytes transduced with the panel of CAR-SCAs were enriched to >90% purity and labeled with CellTrace Violet, then co-cultured with irradiated HIV-1 NL4-3-infected T2 cells. CellTrace Violet fluorescence was assessed by flow cytometry after 7 days. The open histograms indicate transduced cells exposed to control uninfected cells, while the shaded histograms indicated those exposed to the infected cells.

As shown in FIG. 11, CD8$^+$ T lymphocytes expressing the CAR-SCAs that were expanded and enriched by antibody stimulation according to the present invention proliferate in response to HIV-1 infected cells. In further experiments, after co-culture with irradiated HIV-1 strain NL4-3-infected T2 cells or control uninfected T2 cells, all effector cells transduced with the CAR-SCAs exhibited HIV-1-specific proliferation to varying degrees (FIG. 12). These results confirm that the SCA portion of the CAR-SCAs retained the specificity of the parental antibodies against HIV-1 envelope on the surface of infected cells.

HIV-1 Suppressive Activity of CAR-SCAs in Primary CD8+T Lymphocytes

Figure 13:
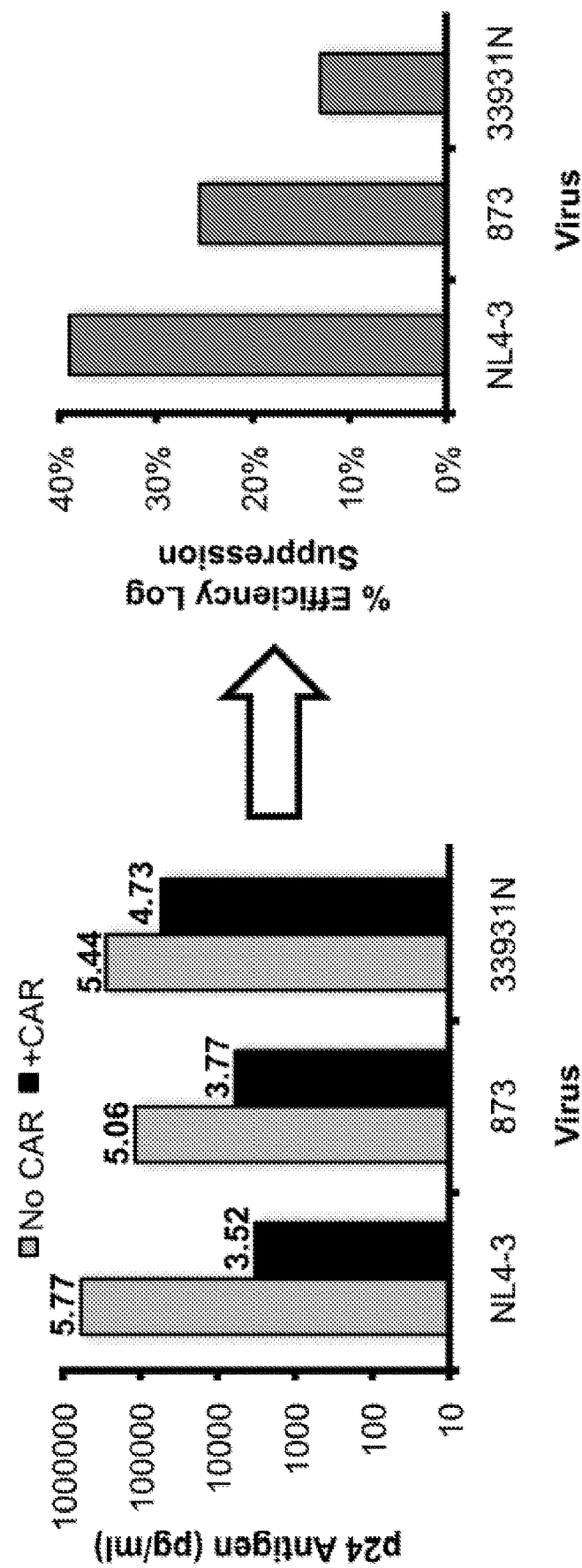
FIG. 13 are graphs exemplifying the calculation of "% Efficiency Log Suppression." T1-CCR5 cells were infected with the indicated viruses at multiplicity of infection 10-1 $TCID_{50}$/cell and cultured with or without the HIV-1-specific CAR-10E8-transduced CD8+ T cells (>90% enriched, effector:target ratio of 1:4). The transduced cells were enriched to >90% purity. Left: HIV-1 p24 antigen was measured by ELISA on Day 6; log units of p24 antigen are indicated above each bar; first bar of each set is No CAR and second bar of each set is +CAR. Right: the efficiency of suppression was plotted as the percentage drop in log units of p24 antigen comparing cultures with and without CAR T cells added.
Figure 14:
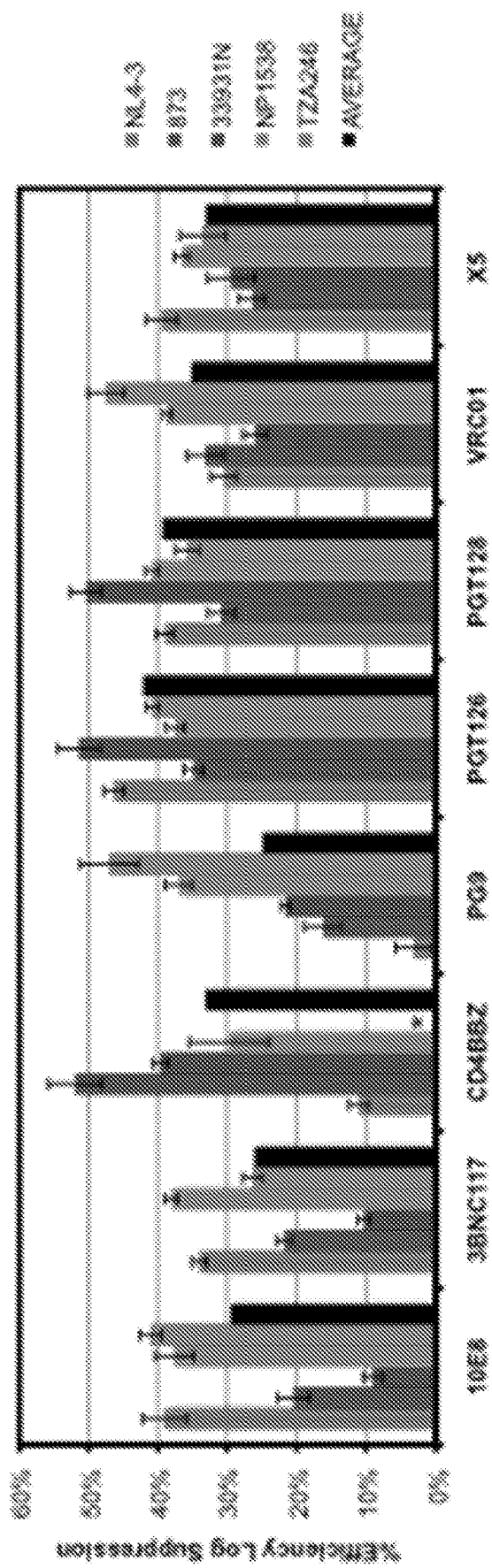
FIG. 14 is a graph showing the efficiencies of anti-$F_{ab}$-enriched CAR-SCAs clones against a panel of HIV-1 isolates. Clones expressing CAR-SCAs that had been expanded to >90% purity with multiple rounds of anti-$F_{ab}$ stimulation (except CD4-BBZ, a control HIV-1-specific CAR) enrichment/expansion were tested against a panel of 5 viruses (clade B except for TZA246, clade C) as shown in FIG. 13. In each set of bars, the order from left to right is: NL4-3, 873, 33931N, NP1538, TZA246, and Average. For the bars representing each indicated virus, each bar represents the median of all replicates from 1-6 experiments (mean 2.9 experiments, standard deviation 1.1 experiments) each with triplicates, with standard error bars. The Average bars represent the average across all viruses. Most culture controls without CARs had viral replication of 4 to 6 logs pg p24 antigen; thus a 40% efficiency value of log suppression in an experiment where the control was 5 logs would indicate 0.4×5=2 logs of virus suppression (100-fold drop).

As set forth in Example 5, the ability of expanded and enriched T cells expressing the CAR-SCAs to suppress HIV viral replication was tested. Using 10E8 clones as an example, HIV-1 p24 antigen was measured by ELISA on Day 6 and the efficiency of suppression was plotted as the percentage drop in log units of p24 antigen comparing cultures having added thereto T cells expressing the CAR-10E8 and T cells without the CAR-10E8. The results are shown in FIG. 13. Compositions comprising cells expressing the CAR-SCAs that were expanded to >90% using multiple rounds of anti-F$_{ab}$ stimulation (except CD4-BBZ, a control HIV-1-specific CAR) enrichment/expansion according to the present invention were tested against a panel of 5 viruses (clade B except for TZA246, clade C). The results are shown in FIG. 14. Each set of bars represent the median of all replicates from 1-6 experiments (mean 2.9 experiments, standard deviation 1.1 experiments) each with triplicates, with standard error bars for the following viruses in order from left to right: NL4-3, 873, 33931N, NP1538, and TZA246. The last (right) bar in each set represents the average across all viruses. Most culture controls without CAR-SCAs had viral replication of 4 to 6 logs pg p24 antigen; thus a 40% efficiency value of log suppression in an experiment where the control was 5 logs would indicate 0.4×5=2 logs of virus suppression (100-fold drop). For this limited set of viruses, some CAR-SCAs, such as CAR-PGT126, appeared to have broader coverage than others, such as CAR-3BNC117.

Figure 15:
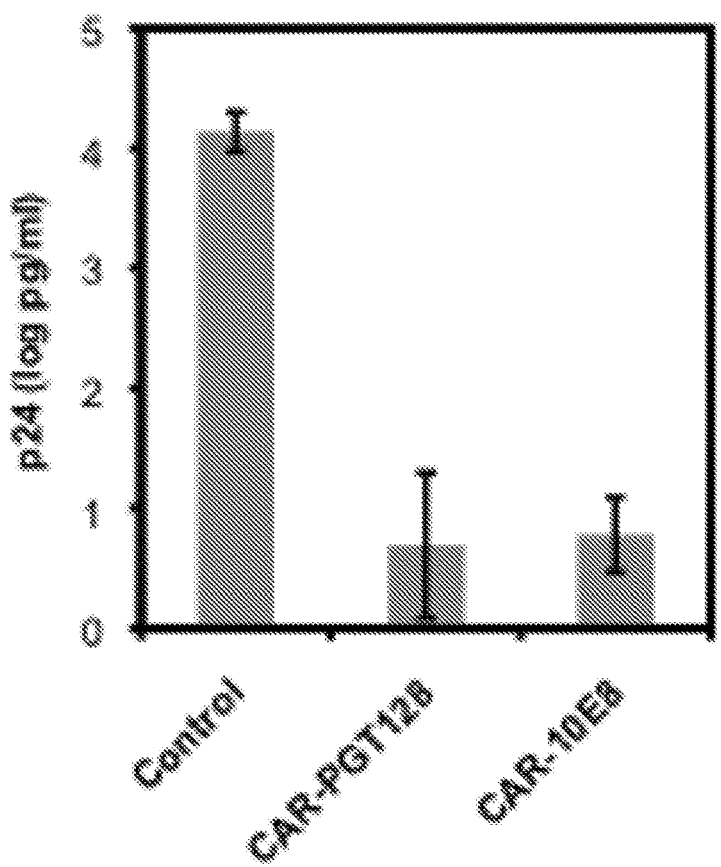
FIG. 15 is a graph summarizing the ability of CAR-SCA transduced primary CD8+ T lymphocytes to suppress HIV-1 replication. T2 cells were acutely infected with HIV-1 strain NL4-3 at a multiplicity of $10^{-2}$ $TCID_{50}$/cell and co-cultured with cloned CAR-SCA transduced primary CD8+ T lymphocytes at a ratio of $5\times10^4$ and $1.25\times10^4$ respectively in triplicate in a 96 well plate. The concentrations of p24 antigen determined by ELISA on day 6 are plotted.

Additional experiments with two CAR-SCA transduced primary CD8$^+$ T lymphocyte clones were performed to test their antiviral suppressive activity. As shown in FIG. 15, clones expressing CAR-X5 and CAR-PGT128, showed potent antiviral activity (>3 log units). Additional assays may be performed using lower or different effector:target ratios than the 1:4 ratio used in this experiment to assess differences between various CAR-SCAs.

Mediated Specific Killing of HIV-1-Infected Target Cells

Figure 16:
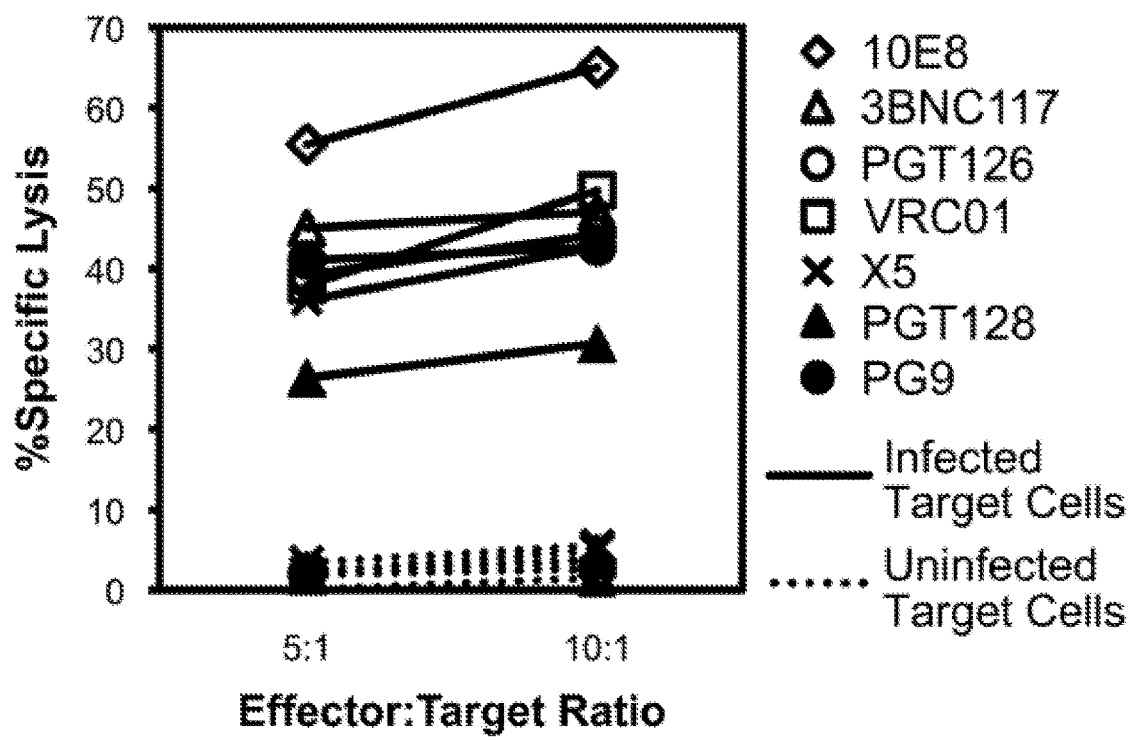
FIG. 16 is a graph summarizing specific killing of HIV-1-infected target cells mediated by clones expressing CAR-SCAs. CAR-SCA transduced primary CD8+ T lymphocytes were co-cultured with HIV-1-infected T2 cells in standard four-hour chromium release assays to assess killing mediated by the CARs. CAR-PGT128 and CAR-PG9, tested for killing in a separate experiment from the other CAR-SCAs, exhibited similar killing activity. The relative efficiencies of the CAR-SCAs varied between experiments and no single CAR-SCA appeared consistently superior.

The expanded and enriched CAR-SCA transduced effector cells were tested for specific killing of HIV-1-infected CD4$^+$ lymphocytes. Chromium release killing assays according to Example 6 were performed to determine whether the cells expressing CAR-SCAs that were selectively expanded and enriched effectively kill HIV-1 infected target cells. Briefly, the expanded and enriched CAR-SCA transduced cells were assayed in chromium release assays against HIV-1 strain NL4-3-infected T2 cells or control uninfected T2 cells. The results in FIG. 16 show that all CAR-SCA effector cells that were expanded and enriched mediated substantial killing of infected versus uninfected target cells at effector:target ratios of 5:1, thereby indicating specific targeting of HIV-1-infected cells.

Figure 17:
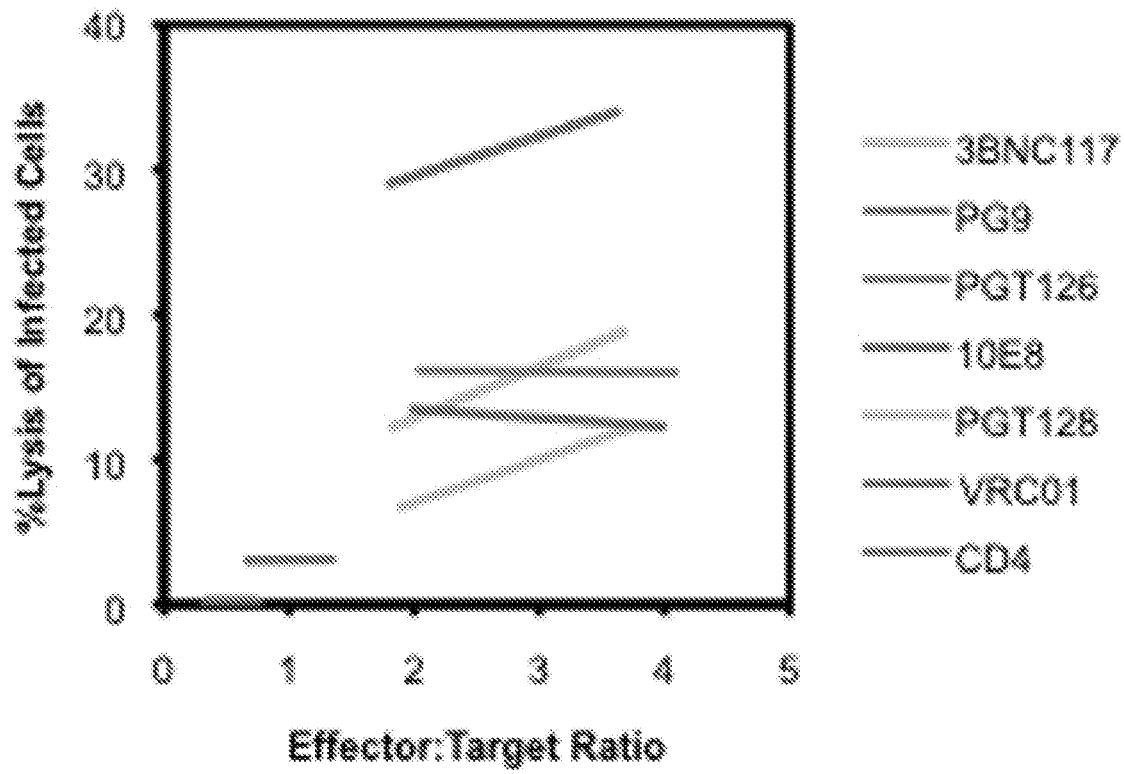
FIG. 17 is a graph summarizing the HIV-1-specific killing activity of bulk CAR-SCA transduced CD8+ T lymphocyte lines. The killing activity of bulk (uncloned) CAR-SCA transduced cells was determined by $^{51}$Cr release assays using T2 cells infected with HIV-1 strain NL4-3. The calculated effector:target ratio was calculated according to the percentage of CAR-SCA expressing effector cells (range from 8% to 54%, original gross effector:target ratios of 10:1 and 5:1). The cytolysis of infected cells was background-subtracted for uninfected cell killing. CAR-X5 was not tested and the effector:target ratios of the CAR-CD4 (the index CAR using CD4 as a receptor for gp120) and CAR-VRC01 were too low to be interpretable in this experiment. In the graph, the first line on the left is CD4 followed by VRC01. Then the lines starting at the Effector:Target Ratio of 2, from top to bottom are as follows: 10E8, PGT126, PG9, 3BNC117, and PGT128.
Figure 18:
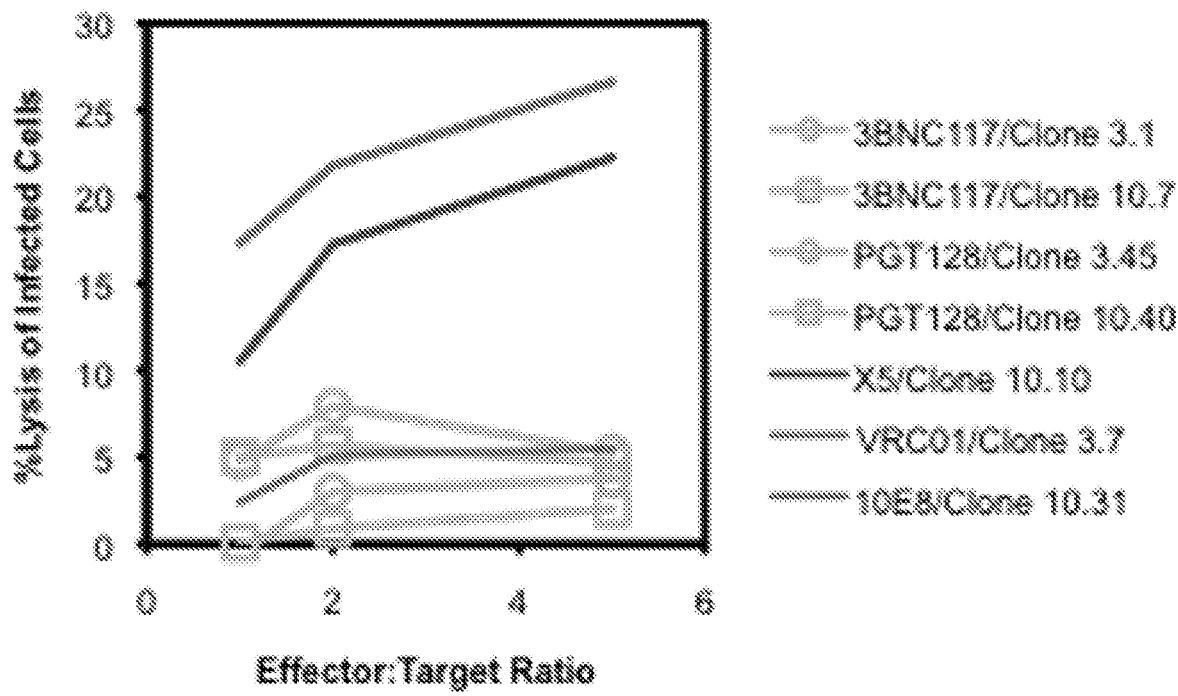
FIG. 18 is a graph summarizing the HIV-1-specific killing activity of cloned CAR-SCA transduced CD8$^+$ T lymphocytes. The killing activity of CAR-SCA transduced cells cloned at limiting dilution was determined by $^{51}$Cr release assays using T2 cells infected with HIV-1 strain NL4-3. Observed cytolysis (background-subtracted for uninfected cell killing) is plotted for the indicated 5 CAR-SCAs (two clones each for 3BNC117 and PGT128). CAR-SCAs derived from PGT126, PG9, and CD4 were not tested. About 90% of target cells were infected with HIV-1. In the graph, starting at the Effector:Target Ratio of 2, from top to bottom are as follows: 10E8, X5, 3BNC117/Clone 3.1, PGT128/Clone 10.40, VRC01, PGT128/Clone 3.45, and 3BNC117/Clone 10.7.

Bulk (uncloned) CAR-SCA transduced CD8$^+$ T lymphocyte lines were tested for HIV-1-specific cytolytic capacity against HIV-1-infected cells. In initial studies, six of the cell lines transduced with the CAR-SCAs showed high activity of CAR-10E8 and potential lesser activity of CAR-3BNC117, CAR-PGT126, CAR-PGT128, and CAR-VRC01 as shown in FIG. 17. The expression level of CAR-PG9 was too low to evaluate for antiviral activity. Further testing of limited dilution clones expressing the CAR-SCAs that were derived from the bulk CD8$^+$ T lymphocyte lines was performed. The results shown in FIG. 18 confirm the potency of cell lines expressing CAR-10E8 and CAR-X5. Clones expressing CAR-VRC01, CAR-3BNC117, and CAR-PGT128 showed lower levels of activity compared to cell lines expressing CAR-10E8 and CAR-X5. Therefore, in some embodiments, CAR-10E8 and CAR-X5 are preferred.

Figure 19:
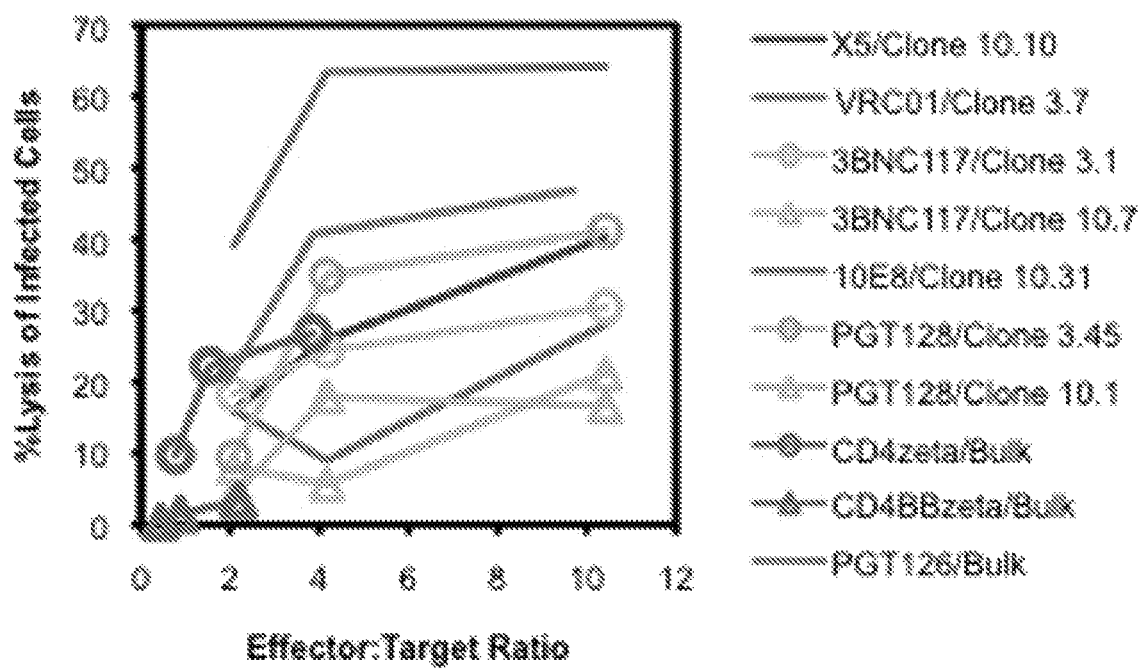
FIG. 19 is a graph summarizing the comparison of HIV-1-specific killing activity of CAR-SCAs versus CD4-based CAR in transduced CD8$^+$ T lymphocytes. The background-subtracted killing activity of CAR-SCA transduced cells (clones and bulk lines as indicated) was compared to that of cells transduced with CD4-based CAR. Both the effector:target ratio and specific lysis were adjusted to reflect killing of HIV-1-infected cells only (assay conditions were effector:target ratios ranging from 1:1 to 5:1 and 48% infection of the target cells). All CAR-SCAs contained the 4-1BB-ζ signaling chain; one CD4-based CAR contained the unmodified ζ and the other the 4-1BB-ζ signaling chain. As set forth in the graph, the left most line is CD4BBzeta/Bulk and the second most left line is CD4zeta/Bulk, then at the Effector:Target Ratio of 6, the lines from top to bottom are 10E8, PGT126/Bulk, PGT128/Clone 3.45, X5/Clone 10.10, 3BNC117/clone 3.1, PGT128/Clone 10.1, VRC01, and 3BNC117/Clone 10.7.

In additional experiments, CD8$^+$ T lymphocyte clones expressing CAR-X5, CAR-VRC01, CAR-3BNC117, CAR-10E8, and CAR-PGT128, bulk CD8$^+$ T lymphocyte lines expressing CAR-PGT126, and bulk CD8$^+$ T lymphocyte lines expressing CAR CD4 were compared for their cytolytic capacities. As shown in FIG. 19 cell line expressing CAR CD4 showed modest cytolytic capacity. At similar effector:target ratios, however, clones expressing CAR-10E8 showed the highest killing activity, and clones expressing other CAR-SCAs showed varying degrees of activity, with cell lines and clones expressing CAR-PGT126 and clones expressing CAR-X5 and CAR-PGT128 having activities that are lower than clones expressing CAR-10E8.

As described herein, cells expressing CAR-SCAs showed HIV-1-specific functional activity, which is somewhat unexpectedly given the uncertain affinity of antibodies converted to single chain versions. Each CAR construct resulted in conformationally relevant cell surface expression (by binding of a goat anti-human $F_{ab}$ antibody) and mediation of HIV-1-specific proliferation, killing, and suppression of viral replication. As disclosed herein, the cells transduced with CAR-SCAs are capable of being selectively expanded and enriched by stimulation with one or more antibodies that specifically bind the CAR-SCAs, and the expanded and enriched cells are capable of clearing HIV-1-infected cells in vivo.

Therefore, the present invention provides methods of selectively expanding and enriching cells expressing CAR-SCAs by antibody stimulation using one or more antibodies that specifically bind the CAR-SCAs, compositions comprising the selectively expanded and enriched cells, and treatment methods which comprise administering the selectively expanded and enriched cells to subjects. In some embodiments, one or more additional rounds of antibody stimulation may be performed to further expand and enrich the proportion of cells expressing the CAR-SCAs compared to cells that do not express the CAR-SCAs.

In some embodiments, the antibody used for antibody stimulation according to the present invention is an anti-human $F_{ab}$ antibody. In some embodiments, the antibody is an anti-human $F_{ab}$ goat antibody. In some embodiments, the antibody is AffiniPure F(ab')2 Fragment Goat Anti-Human IgG (H+L) (#109-096-003, Jackson ImmunoResearch Inc., West Grove, Pa.), AffiniPure F(ab')$_2$ Fragment Goat Anti-Human IgG (H+L) (#109-006-003, Jackson ImmunoResearch Inc., West Grove, Pa.), Anti-Human IgG $F_{ab}$ fragment antibody [401K] (#ab771, Abcam, Cambridge, Mass.), Anti-Human IgG ($F_{ab}$ specific) antibody produced in goat (#MFCD00162431, Sigma-Aldrich), or Monoclonal Anti-Human IgG ($F_{ab}$ specific) antibody produced in mouse (#MFCD00162431, Sigma-Aldrich).

Although whole antibodies were used for selectively expanding and enriching cells expressing CAR-SCAs in the experiments provided herein, antibody stimulation using antibody fragments that specifically bind the CAR-SCAs are contemplated therein. In some embodiments, the antibody fragment specifically binds the CAR-SCA, but does not bind any endogenous TCRs expressed by the non-transduced cells. In some embodiments, the antibody fragment has a higher binding affinity for the CAR-SCA as compared to any endogenous TCRs. In some embodiments, the antibody fragment specifically binds the SCA domain of the CAR-SCA. The antibodies that specifically bind CAR-SCAs and/or antibody fragments that specifically bind CAR-SCAs may be monoclonal, polyclonal, chimeric, and/or humanized.

Nucleic Acid Molecules and Vectors

In some embodiments, the present invention is directed to nucleic acid molecules that encode the CAR-SCAs disclosed herein. Such nucleic acid molecules may be operably linked to one or more regulatory elements, such as a promoter and enhancer, that allow expression of the nucleotide sequence in the intended target cells (e.g., a cell that is genetically modified to synthesize the encoded antibody). Suitable promoters and enhancers are known in the art.

Cells

In some embodiments, the present invention is directed to cells expressing a CAR-SCA that have been expanded and enriched by antibody stimulation with one or more antibodies that specifically bind the CAR-SCA.

Compositions

In some embodiments, compositions according to the present invention comprise cells expressing a CAR-SCA that have been expanded and enriched by antibody stimulation with one or more antibodies that specifically bind the CAR-SCA. In some embodiments, at least about 50%, preferably at least about 60%, more preferably at least about 70%, even more preferably at least about 80%, and most preferably at least about 90%, and most preferably 95% of the total cells in the composition express the CAR-SCA.

In some embodiments, compositions according to the present invention are pharmaceutical compositions. In some embodiments, the pharmaceutical compositions comprise a therapeutically effective amount cells expressing a CAR-SCA that have been expanded and enriched by antibody stimulation with one or more antibodies that specifically bind the CAR-SCA. As used herein, a "pharmaceutical composition" refers to a composition suitable for pharmaceutical use in a subject. A pharmaceutical composition generally comprises an effective amount of an active agent and a pharmaceutically acceptable carrier, e.g., a buffer, adjuvant, and the like. As used herein, a "pharmaceutically acceptable carrier" refers to solvents, dispersion media, coatings, antibacterial and antifungal agents, isotonic and absorption delaying agents, and the like, that are compatible with the active ingredient and comply with the applicable standards and regulations, e.g., the pharmacopeial standards set forth in the United States Pharmacopeia and the National Formulary (USP-NF) book, for pharmaceutical administration. Thus, for example, unsterile water is excluded as a pharmaceutically acceptable carrier for, at least, intravenous administration. Pharmaceutically acceptable vehicles include those known in the art. See, e.g., REMINGTON: THE SCIENCE AND PRACTICE OF PHARMACY. 20th ed. (2000) Lippincott Williams & Wilkins. Baltimore, Md.

As used herein, an "effective amount" refers to a dosage or amount sufficient to produce a desired result. The desired result may comprise an objective or subjective response in, for example, a treatment group as compared to a control group in, for example, an in vitro assay. In some embodiments, the effective amount is a "therapeutically effective amount". As used herein, a "therapeutically effective amount" refers to an amount sufficient to effect a beneficial or desired therapeutic (including preventative) result in a subject, such as a reduction of HIV infected cells and/or suppression of HIV viral replication, as compared to a control or a baseline measurement before treatment. A therapeutically effective amount may be administered as a single dose or as a series of several doses. The skilled artisan will appreciate that certain factors may influence the dosage required to effectively treat a subject, including the degree of symptoms, previous treatments, the general health and age of the subject, and the like. Nevertheless, effective and therapeutically effective amounts may be readily determined using methods known in the art.

Pharmaceutical compositions of the present invention may be formulated for the intended route of delivery, including intravenous, intramuscular, intra peritoneal, subcutaneous, intraocular, intrathecal, intraarticular, intrasynovial, cisternal, intrahepatic, intralesional injection, intracranial injection, infusion, and/or inhaled routes of administration using methods known in the art. Pharmaceutical compositions according to the present invention may include one or more of the following: pH buffered solutions, adjuvants (e.g., preservatives, wetting agents, emulsifying agents, and dispersing agents), liposomal formulations, nanoparticles, dispersions, suspensions or emulsions as well as sterile powders for reconstitution into sterile injectable solutions or dispersions. The compositions and formulations of the present invention may be optimized for increased stability and efficacy using methods known in the art.

Dosages and Regimen

Pharmaceutical compositions of the present invention may be provided in dosage unit forms. As used herein, "dosage unit form" refers to physically discrete units suited as unitary dosages for the subject to be treated; each unit containing a predetermined quantity of an active ingredient calculated to produce the desired therapeutic effect in association with the required pharmaceutically acceptable carrier. The specification for the dosage unit forms of the invention are dictated by the unique characteristics of the active ingredient and the particular therapeutic effect to be achieved, and the limitations inherent in the art of compounding such an active ingredient for the treatment of individuals.

Toxicity and therapeutic efficacy of the compositions according to the present invention can be determined by standard pharmaceutical procedures in cell cultures or experimental animals. For example, one may determine the lethal dose, $LC_{50}$ (the dose expressed as concentration× exposure time that is lethal to 50% of the population) or the $LD_{50}$ (the dose lethal to 50% of the population), and the $ED_{50}$ (the dose therapeutically effective in 50% of the population) by methods known in the art. The dose ratio between toxic and therapeutic effects is the therapeutic index and it can be expressed as the ratio $LD_{50}/ED_{50}$. Compositions that exhibit large therapeutic indices are preferred. While compositions that exhibit toxic side effects may be used, care should be taken to use a delivery system that targets such compositions to the site of affected tissue in order to reduce side effects.

The data obtained from the cell culture assays and animal studies can be used in formulating a range of dosages for various combinations of one or more compositions of the present invention for use in humans. The dosages are preferably within a range of circulating concentrations that include the $ED_{50}$ with little or no toxicity. The dosage may vary within this range depending upon the dosage form employed and the route of administration utilized. A therapeutically effective dose can be estimated from cell culture assays. A dose may be formulated in animal models to achieve a circulating plasma concentration range that includes the ICso (i.e., the concentration of the test composition which achieves a half-maximal inhibition of symptoms) as determined in cell culture. Such information can be used to more accurately determine useful doses in humans. Levels in plasma may be measured using methods known in the art.

Additionally, a suitable dosage for a given subject can be determined by an attending physician or other qualified medical personnel, based on various clinical factors. As is well known in the medical arts, dosages for any one subject depend upon many factors, including the subject's size, body surface area, age, the particular compound to be administered, sex of the subject, time, and route of administration, general health, and other drugs being administered concurrently. Those of skilled in the art will readily appreciate that dose levels can vary as a function of the specific composition, e.g., the specific CAR-SCA, the severity of the symptoms and the susceptibility of the subject to side effects. Nevertheless, preferred dosages may be readily determined by those of skill in the art.

Other Treatments

The methods of the present invention may be used to selectively expand and enrich cells expressing other CAR-SCAs that are effective in treating diseases and disorders other than HIV infection. Therefore, methods of the present invention comprise culturing cells transduced with a given CAR-SCA in the presence of an antibody that specifically binds the given CAR-SCA. Various methods known in the art can be used to obtain antibodies, including monoclonal antibodies, against a given CAR-SCA. In some embodiments, the anti-CAR-SCA antibodies specifically bind the given CAR-SCA, but do not bind any endogenous TCRs. In some embodiments, the anti-CAR-SCA antibodies have a higher binding affinity for the given CAR-SCA as compared to any endogenous TCRs. In some embodiments, the anti-CAR-SCA antibodies bind the SCA of the given CAR-SCA. In some embodiments, the anti-CAR-SCA antibody is an anti-human $F_{ab}$ antibody. In some embodiments, the anti-CAR-SCA antibody is an anti-human $F_{ab}$ goat antibody. In some embodiments, the anti-human $F_{ab}$ antibody is AffiniPure F(ab')2 Fragment Goat Anti-Human IgG (H+L) (#109-096-003, Jackson ImmunoResearch Inc., West Grove, Pa.), AffiniPure F(ab')$_2$ Fragment Goat Anti-Human IgG (H+L) (#109-006-003, Jackson ImmunoResearch Inc., West Grove, Pa.), Anti-Human IgG $F_{ab}$ fragment antibody [401K] (#ab771, Abcam, Cambridge, Mass.), Anti-Human IgG ($F_{ab}$ specific) antibody produced in goat (#MFCD00162431, Sigma-Aldrich), and Monoclonal Anti-Human IgG ($F_{ab}$ specific) antibody produced in mouse (#MFCD00162431, Sigma-Aldrich).

The following examples are intended to illustrate but not to limit the invention.

EXAMPLES

Antibodies

The anti-human $F_{ab}$ antibodies used in the exemplary experiments described herein include AffiniPure F(ab')2 Fragment Goat Anti-Human IgG (H+L) (#109-096-003, Jackson ImmunoResearch Inc., West Grove, Pa.) and AffiniPure F(ab')$_2$ Fragment Goat Anti-Human IgG (H+L) (#109-006-003, Jackson ImmunoResearch Inc., West Grove, Pa.). However, it should be noted that other antibodies known in the art or produced using methods known in the art can be used in accordance with the present invention. Examples of suitable antibodies include Anti-Human IgG $F_{ab}$ fragment antibody [4A11] (#ab771, Abcam, Cambridge, Mass.), Anti-Human IgG ($F_{ab}$ specific) antibody produced in goat (#MFCD00162431, Sigma-Aldrich), and Monoclonal Anti-Human IgG ($F_{ab}$ specific) antibody produced in mouse (#MFCD00162431, Sigma-Aldrich).

Production of Lentiviral Vectors

Lentivirus was produced by co-transfection of 293T cells with a CAR lentiviral vector construct plasmid (10 µg) in conjunction with packaging and pseudotyping vectors including the lentiviral packaging plasmid pCMVDR8.2DVPR (7 µg) and the vesicular stomatitis virus envelope glycoprotein G expression vector pHCMVG (3 µg) using BioT transfection reagent (per the manufacturer's protocol, Bioland, Paramount, Calif.) with 5×10$^6$ 293 T cells that had been seeded in a T75 tissue culture flask 24 hours previously. Supernatants were obtained 24 and 48 hours after transfection, passed through a 0.45 µm filter, and concentrated by ultracentrifugation (26,000 rpm for 90 minutes at 4° C., SW28 rotor, Beckman Coulter, Fullerton, Calif.). Aliquots containing approximately 50 ng HIV-1 p24 antigen in 50 µl were frozen at −80° C. until use.

Cells and Media

The immortalized HIV-1-permissive CD4-expressing cell lines T1 (Salter, et al. (1985) Immunogenetics 21:235-246), T2 (Salter, et al. (1986) EMBO J 5:943-949), and Jurkat cells were maintained as previously described (Bennett, et al. (2007) J Virol 81:4973-4980; Yang, et al. (1996) J Virol 70:5799-5806; and Yang, et al. (1997) J Virol 71:3120-3128) in complete medium (R10) consisting of RPMI 1640 (Lonza, Allendale, N.J.) supplemented with 2 mM L-glutamine (Mediatech, Manassas, Va.), 100 U/ml penicillin (Mediatech, Manassas, Va.), 100 U/ml streptomycin (Mediatech, Manassas, Va.), 10 mM HEPES (Sigma, St. Louis, Mo.), and 10% heat-inactivated fetal bovine serum (FBS) (Sigma, St. Louis, Mo.). 293T cells were maintained in Dulbecco's Modified Essential Medium supplemented with L-glutamine, penicillin, streptomycin, and FBS as above and previously described (Bennett, et al. (2010) Aids 24:2619-2628). Primary CD8+ T lymphocytes were isolated from peripheral blood mononuclear cells (PBMCs) of healthy HIV-1-uninfected donors using anti-CD8 antibody coated magnetic beads as per manufacturer's directions (MACS column separation kit, Miltenyi, San Diego, Calif.) and then cultured for 5 days in R10 supplemented with 50 U/ml recombinant human interleukin-2 (NIH AIDS Reagent Repository) (R10-50) in the presence of the anti-CD3 antibody 12F6 (Wong, et al. (1987) J Immunol 139:1369-1374), yielding purity of >99% CD3+/CD8+ cells by flow cytometry. All experiments were confirmed with cells from multiple donors and showed no significant donor-specific differences.

Example 1

Construction of CAR Vectors

The backbone for the CAR-SCA constructs was the pTRPE123-cMET-BBζ CAR plasmid provided as the generous gift of Dr. Carl June. This lentiviral expression vector (FIG. 5) contained the gene for second generation CAR with a single chain antibody against hepatocyte growth factor receptor (cMET) fused to human IgG4 hinge sequence, human CD8 transmembrane sequence, and cytoplasmic domains of human 4.1BB (CD137) and human CD3 complex chain (CD247). This vector was modified by creating a novel Apa I restriction site via a silent mutation in the hinge sequence (FIG. 5). This was accomplished by subcloning the Xba I-Sma I restriction fragment into pUC19, in which the mutation was created by point mutagenesis (QuikChange kit, Invitrogen, Carlsbad, Calif.). After sequencing of the entire fragment to ensure no PCR-induced errors, this restriction fragment was ligated into the parental vector. Single chain antibody sequences of heavy chain-linker-light chain were synthesized as codon-optimized genes preceded by the signal sequence for granulocyte-macrophage colony stimulating factor and followed by the beginning of the hinge region, flanked by Xba I and Apa I restriction sites, allowing ligation into the parental vector after restriction digestion.

The amino acid sequences of the resulting CAR constructs showing the signal sequence (non-bolded italics (SEQ ID NO:1)) followed by the $V_H$ sequence (bold) linked to the $V_L$ sequence (bold italics) via a linker (underlined (SEQ ID NO:2)) followed by the transmembrane/signaling domains (regular font (SEQ ID NO:3)) are as follows:

```
VRC01 (SEQ ID NO. 4):
MLLLVTSLLLCELPHPAFLLIPQVQLVQSGGQMKKPGESMRISCRASGYEFIDCTLNWIRLAPGKR

PEWMGWLKPRGGAVNYARPLQGRVTMTRDVYSDTAFLELRSLTVDDTAVYFCTRGKNCDYNWDFEH

WGRGTPVIVSSGGGGSGGGGSGGGGSEIVLTQSPGTLSLSPGETAIISCRTSQYGSLAWYQQRPGQ

APRLVIYSGSTRAAGIPDRFSGSRWGPDYNLTISNLESGDFGVYYCQQYEFFGQGTKVQVDIKRES

KYGPPCPPCPAPEFLGGPSVFLFPPKPKDTLMISRIPEVTCVVVDVSQEDPEVQFNWYVDGVEVHN

AKTKPREEQFNSTYRVVSVLTVLHQDWLNGKEYKCKVSNKGLPSSIEKTISKAKGQPREPQVYTLP

PSQEEMTKNQVSLTCLVKGFYPSDIAVEWESNGQPENNYKTTPPVLDSDGSFFLYSRLTVDKSRWQ

EGNVFSCSVMHEALHNHYTQKSLSLSLGKDIYIWAPLAGTCGVLLLSLVITLYCKRGRKKLLYIFK

QPFMRPVQTTQEEDGCSCRFPEEEEGGCELRVKFSRSADAPAYKQGQNQLYNELNLGRREEYDVLD

KRRGRDPEMGGKPRRKNPQEGLYNELQKDKMAEAYSEIGMKGERRRGKGHDGLYQGLSTATKDTYD

ALHMQALPPR
```

The $V_H$ sequence and the $V_L$ sequence of VRC01 are SEQ ID NO:5, and SEQ ID NO:6, respectively.

```
3BNC117 (SEQ ID NO: 7):
MLLLVTSLLLCELPHPAFLLIPQVQLLQSGAAVTKPGASVRVSCEASGYNIRDYFIHWWRQAPGQG

LQWVGWINPKTGQPNNPRQFQGRVSLTRHASWDFDTFSFYMDLKALRSDDTAVYFCARQRSDYWDF

DVWGSGTQVTVSSASTKGPGGGGSGGGGSGGGGSDIQMTQSPSSLSASVGDTVTITCQANGYLNWY

QQRRGKAPKLLIYDGSKLERGVPSRFSGRRWGQEYNLTINNLQPEDIATYFCQVYEFVVPGTRLDL

KRTVAAPESKYGPPCPPCPAPEFLGGPSVFLFPPKPKDTLMISRTPEVICVVVDVSQEDPEVQFNW

YVDGVEVHNAKTKPREEQFNSTYRVVSVLTVLHQDWLNGKEYKCKVSNKGLPSSIEKTISKAKGQP

REPQVYTLPPSQEEMTKNQVSLTCLVKGFYPSDIAVEWESNGQPENNYKTTPPVLDSDGSFFLYSR

LTVDKSRWQEGNVFSCSVMHEALHNHYTQKSLSLSLGKDIYIWAPLAGTCGVLLLSLVITLYCKRG

RKKLLYIFKQPFMRPVQTTQEEDGCSCRFPEEEEGGCELRVKFSRSADAPAYKQGQNQLYNELNLG
```

-continued
RREEYDVLDKRRGRDPEMGGKPRRKNPQEGLYNELQKDKMAEAYSEIGMKGERRRGKHDGLYQGL

STATKDTYDALHMQALPPR

The V<sub>H</sub> sequence and the V<sub>L</sub> sequence of 3BNC117 are SEQ ID NO:8, and SEQ ID NO:9, respectively.

X5 (SEQ ID NO: 10):
MLLLVTSLLLCELPHPAFLLIPLEQSGAEVKKPGSSVQVSCKASGGTFSMYGFNWVRQAPGHGLEW

MGGIIPIFGTSNYAQKFRGRVTFTADQATSTAYMELTNLRSDDTAVYYCARDFGPDWEDGDSYDGS

GRGFFDFWGQGTLVTVSSGGGGSGGGGSGGGGSELVLTQSPGTLSLSAGERATLSCRASQSVSSGS

LAWYQQKPGQAPRLLIYGASTRATGIPDRFSGSGSGTDFTLTIGRLEPEDLAVYYCQQYGTSPYTF

GQGTKLEIESKYGPPCPPCPAPEFLGGPSVFLFPPKPKDTLMISRTPEVTCVVVDVSQEDPEVQFN

WYVDGVEVHNAKTKPREEQFNSTYRVVSVLTVLHQDWLNGKEYKCKVSNKGLPSSIEKTISKAKGQ

PREPQVYTLPPSQEEMTKNQVSLTCLVKGFYPSDIAVEWESNGQPENNYKTTPPVLDSDGSFFLYS

RLTVDKSRWQEGNVFSCSVMHEALHNHYTQKSLSLSLGKDIYIWAPLAGTCGVLLLSLVITLYCKR

GRKKLLYIFKQPFMRPVQTTQEEDGCSCRFPEEEEGGCELRVKFSRSADAPAYKQGQNQLYNELNL

GRREEYDVLDKRRGRDPEMGGKPRRKNPQEGLYNELQKDKMAEAYSEIGMKGERRRGKHDGLYQG

LSTATKDTYDALHMQALPPR

The V<sub>H</sub> sequence and the V<sub>L</sub> sequence of X5 are SEQ ID NO:11, and SEQ ID NO:12, respectively.

PGT126 (SEQ ID NO: 13):
MLLLVTSLLLCELPHPAFLLIPQPQLQESGPGLVEASETLSLTCTVSGDSTAACDYFWGWVRQPPG

KGLEWIGGLSHCAGYYNTGWTYHNPSLKSRLTISLDTPKNQVFLKLNSVTAADTAIYYCARFDGEV

LVYHDWPKPAWVDLWGRGTLVTVTSSGGGGSGGGGSGGGGSQSALTQPPSASGSPGQSISISCTG

TSNRFVSWYQQHPGKAPKLVIYGVNKRPSGVPDRFSGSKSGNTASLTVSGLQTDDEAVYYC

NWDVIFGGGTKLTVLESKYGPPCPPCPAPEFLGGPSVFLFPPKPKDTLMISRTPEVICVVVDVSQE

DPEVQFNNYVDGVEVHNAKTKPREEQFNSTYRVVSVLTVLHQDWLNGKEYKCKVSNKGLPSSIEKT

ISKAKGQPREPQVYTLPPSQEEMTKNQVSLTCLVKGFYPSDIAVEWESNGQPENNYKTTPPVLDSD

GSFFLYSRLTVDKSRWQEGNVFSCSVMHEALHNHYTQKSLSLSLGKDIYIWAPLAGTCGVLLLSLV

ITLYCKRGRKKLLYIFKQPFMRPVQTTQEEDGCSCRFPEEEEGGCELRVKFSRSADAPAYKQGQNQ

LYNELNLGRREEYDVLDKRRGRDPEMGGKPRRKNPQEGLYNELQKDKMAEAYSEIGMKGERRRGKG

HDGLYQGLSTATKDTYDALHMQALPPR

The V<sub>H</sub> sequence and the V<sub>L</sub> sequence of PGT126 are SEQ ID NO:14, and SEQ ID NO:15, respectively.

PGT128 (SEQ ID NO: 16):
MLLLVTSLLLCELPHPAFLLIPQPQLQESGPTLVEASETLSLTCAVSGDSTAACNSFWGWVRQPPG

KGLEWVGSLSHCASYWNRGWTYHNPSLKSRLTLALDTPKNLVFLKLNSVTAADTATYYCARFGGEV

LRYTDWPKPAWVDLWGRGTLVTVSSGGGGSGGGGSGGGGSQSALTQPPSASGSPGQSITISCTGTS

NNFVSWYQQHAGKAPKLVIYDVNKRPSGVPDRFSGSKSGNTASLTVSGLQTDDEAVYYCGSLVGNW

DVIFGGGTKLTVLESKYGPPCPPCPAPEFLGGPSVFLFPPKPKDTLMISRTPEVICVVVDVSQEDP

EVQFNNYVDGVEVHNAKTKPREEQFNSTYRVVSVLTVLHQDWLNGKEYKCKVSNKGLPSSIEKTIS

KAKGQPREPQVYTLPPSQEEMTKNQVSLTCLVKGFYPSDIAVEWESNGQPENNYKTTPPVLDSDGS

-continued

FFLYSRLTVDKSRWQEGNVFSCSVMHEALHNHYTQKSLSLSLGKDIYIWAPLAGTCGVLLLSLVIT

LYCKRGRKKLLYIFKQPFMRPVQTTQEEDGCSCRFPEEEEGGCELRVKFSRSADAPAYKQGQNQLY

NELNLGRREEYDVLDKRRGRDPEMGGKPRRKNPQEGLYNELQKDKMAEAYSEIGMKGERRRGKGHD

GLYQGLSTATKDTYDALHMQALPPR

The $V_H$ sequence and the $V_L$ sequence of PGT128 are SEQ ID NO:17, and SEQ ID NO:18, respectively.

PG9 (SEQ ID NO. 19):
*MLLLVTSLLLCELPHPAFLLI*PQRLVESGGGVVQPGSSLRLSCAASGFDFSRQGMHWVRQAPGQGL

EWVAFIKYDGSEKYHADSVWGRLSISRDNSKDTLYLQMNSLRVEDTATYFCVREAGGPDYRNGYNY

YDFYDGYYNYHYMDVWGKGTTVTVSSGGGGSGGGGSGGGGS*QSALTQPASVSGSPGQSITISCNGT*

*SNDVGGYESVSWYQQHPGKAPKVVIYDVSKRPSGVSNRFSGSKSGNTASLTISGLQAEDEGDYYCK*

*SLTSTRRRVFGTGTKLTVL*ESKYGPPCPPCPAPEFLGGPSVFLFPPKPKDTLMISRTPEVICVVVD

VSQEDPEVQFNNYVDGVEVHNAKTKPREEQFNSTYRVVSVLTVLHQDWLNGKEYKCKVSNKGLPSS

IEKTISKAKGQPREPQVYTLPPSQEEMTKNQVSLTCLVKGFYPSDIAVEWESNGQPENNYKTTPPV

LDSDGSFFLYSRLTVDKSRWQEGNVFSCSVMHEALHNHYTQKSLSLSLGKDIYIWAPLAGTCGVLL

LSLVITLYCKRGRKKLLYIFKQPFMRPVQTTQEEDGCSCRFPEEEEGGCELRVKFSRSADAPAYKQ

GQNQLYNELNLGRREEYDVLDKRRGRDPEMGGKPRRKNPQEGLYNELQKDKMAEAYSEIGMKGERR

RGKGHDGLYQGLSTATKDTYDALHMQALPPR

The $V_H$ sequence and the $V_L$ sequence of PG9 are SEQ ID NO:20, and SEQ ID NO:21, respectively.

10E8 (SEQ ID NO: 22):
*MLLLVTSLLLCELPHPAFLLI*PEVQLVESGGGLVKPGGSLRLSCSASGFDFDNAWMTWVRQPPGKG

LEWVGRITGPGEGWSVDYAAPVEGRFTISRLNSINFLYLEMNNLRMEDSGLYFCARTGKYYDFWSG

YPPGEEYFQDWGRGTLVTVSSGGGGSGGGGSGGGGS*SYELTQETGVSVALGRTVTITCRGDSLRSH*

*YASWYQKKPGQAPILLFYGKNNRPSGVPDRFSGSASGNRASLTISGAQAEDDAEYYCSSRDKSGS*

*LSVFGGGTKLTVL*ESKYGPPCPPCPAPEFLGGPSVFLFPPKPKDTLMISRTPEVTCVVVDVSQEDP

EVQFNWYVDGVEVHNAKTKPREEQFNSTYRVVSVLTVLHQDWLNGKEYKCKVSNKGLPSSIEKTIS

KAKGQPREPQVYTLPPSQEEMTKNQVSLTCLVKGFYPSDIAVEWESNGQPENNYKTTPPVLDSDGS

FFLYSRLTVDKSRWQEGNVFSCSVMHEALHNHYTQKSLSLSLGKDIYIWAPLAGTCGVLLLSLVIT

LYCKRGRKKLLYIFKQPFMRPVQTTQEEDGCSCRFPEEEEGGCELRVKFSRSADAPAYKQGQNQLY

NELNLGRREEYDVLDKRRGRDPEMGGKPRRKNPQEGLYNELQKDKMAEAYSEIGMKGERRRGKGHD

GLYQGLSTATKDTYDALHMQALPPR

The $V_H$ sequence and the $V_L$ sequence of 10E8 are SEQ ID NO:23, and SEQ ID NO:24, respectively.

The codon-optimized sequences encoding the CAR constructs are as follows:

VRC01 (SEQ ID NO: 25):
ATGCTGCTGCTGGTGACAAGCCTGCTGCTGTGCGAGCTGCCCCACCCCGCCTTTCTGCTGATCCCC

CAGGTGCAGCTGGTGCAGTCTGGCGGGCAGATGAAGAAACCCGGCGAGAGCATGCGGATCAGCTGC

CGGGCCTCCGGCTACGAGTTCATCGACTGCACCCTGAACTGGATCCGGCTGGCCCCTGGCAAGAGG

CCCGAGTGGATGGGCTGGCTGAAGCCCAGAGGCGGAGCCGTGAACTACGCCAGACCCCTCCAGGGC

-continued

AGAGTGACCATGACCCGGGACGTGTACAGCGATACCGCCTTCCTGGAACTGCGGAGCCTGACCGTG
GACGATACCGCCGTGTACTTCTGCACCCGGGGCAAGAACTGCGACTACAACTGGGACTTCGAGCAC
TGGGGCAGAGGCACCCCCGTGATCGTGTCTAGCGGAGGCGGAGGATCTGGAGGCGGAGGCTCTGGG
GGAGGCGGAAGCGAGATCGTGCTGACCCAGAGCCCTGGCACCCTGAGCCTGTCTCCCGGCGAAACC
GCCATCATCAGCTGCAGAACCAGCCAGTACGGCAGCCTCGCCTGGTATCAGCAGAGGCCAGGCCAG
GCCCCCAGACTGGTGATCTACAGCGGCAGCACCAGAGCCGCCGGAATCCCCGACAGATTCAGCGGC
TCCAGATGGGGACCTGACTACAACCTGACCATCAGCAACCTGGAAAGCGGCGACTTCGGCGTGTAC
TACTGCCAGCAGTACGAGTTCTTCGGCCAGGGCACCAAGGTGCAGGTGGACATCAAGCGGGAGAGC
AAATACGGGCCCCCCTGCCCCCCTTGCCCTGCCCCCGAGTTCCTGGGCGGACCCAGCGTGTTCCTG
TTCCCCCCCAAGCCCAAGGACACCCTGATGATCAGCCGGACCCCCGAGGTGACCTGTGTGGTGGTG
GACGTGTCCCAGGAGGACCCCGAGGTCCAGTTCAACTGGTACGTGGACGGCGTGGAGGTGCACAAC
GCCAAGACCAAGCCCCGGGAGGAGCAGTTCAATAGCACCTACCGGGTGGTGTCCGTGCTGACCGTG
CTGCACCAGGACTGGCTGAACGGCAAGGAATACAAGTGTAAGGTGTCCAACAAGGGCCTGCCCAGC
AGCATCGAGAAAACCATCAGCAAGGCCAAGGGCCAGCCTCGGGAGCCCCAGGTGTACACCCTGCCC
CCTAGCCAAGAGGAGATGACCAAGAACCAGGTGTCCCTGACCTGCCTGGTGAAGGGCTTCTACCCC
AGCGACATCGCCGTGGAGTGGGAGAGCAACGGCCAGCCCGAGAACAACTACAAGACCACCCCCCCT
GTGCTGGACAGCGACGGCAGCTTCTTCCTGTACAGCCGGCTGACCGTGGACAAGAGCCGGTGGCAG
GAGGGCAACGTCTTTAGCTGCTCCGTGATGCACGAGGCCCTGCACAACCACTACACCCAGAAGAGC
CTGAGCCTGTCCCTGGGCAAGGATATCTACATCTGGGCGCCCTTGGCCGGGACTTGTGGGGTCCTT
CTCCTGTCACTGGTTATCACCCTTTACTGCAAACGGGGCAGAAAGAAACTCCTGTATATATTCAAA
CAACCATTTATGAGACCAGTACAAACTACTCAAGAGGAAGATGGCTGTAGCTGCCGATTTCCAGAA
GAAGAAGAAGGAGGATGTGAACTGAGAGTGAAGTTCAGCAGGAGCGCAGACGCCCCCGCGTACAAG
CAGGGCCAGAACCAGCTCTATAACGAGCTCAATCTAGGACGAAGAGAGGAGTACGATGTTTTGGAC
AAGAGACGTGGCCGGGACCCTGAGATGGGGGGAAAGCCGAGAAGGAAGAACCCTCAGGAAGGCCTG
TACAATGAACTGCAGAAAGATAAGATGGCGGAGGCCTACAGTGAGATTGGGATGAAAGGCGAGCGC
CGGAGGGGCAAGGGGCACGATGGCCTTTACCAGGGTCTCAGTACAGCCACCAAGGACACCTACGAC
GCCCTTCACATGCAGGCCCTGCCCCCTCGCTAA

3BNC117 (SEQ ID NO: 26):
ATGCTGCTGCTGGTGACAAGCCTGCTGCTGTGCGAGCTGCCCCACCCTGCCTTTCTGCTGATCCCC
CAGGTGCAGCTGCTGCAGAGCGGAGCCGCCGTGACAAAGCCTGGCGCTTCTGTGCGGGTGTCCTGC
GAGGCCAGCGGCTACAACATCCGGGACTACTTCATCCACTGGTGGCGGCAGGCCCCAGGCCAGGGA
CTGCAGTGGGTGGGATGGATCAACCCCAAGACCGGCCAGCCCAACAACCCCCGGCAGTTCCAGGGC
CGGGTGTCCCTGACAAGACACGCCAGCTGGGACTTCGACACCTTCAGCTTCTACATGGACCTGAAG
GCCCTGCGGAGCGACGATACCGCCGTGTACTTCTGCGCCAGACAGCGGAGCGACTACTGGGATTTC
GACGTGTGGGGCAGCGGCACCCAGGTCACAGTGTCCAGCGCCAGCACAAAGGGACCTGGCGGCGGA
GGATCTGGCGGAGGCGGAAGTGGCGGAGGGGGCAGCGATATTCAGATGACCCAGAGCCCCAGCAGC
CTGAGCGCCAGCGTGGGCGACACCGTGACCATCACCTGTCAGGCCAACGGATACCTGAACTGGTAT
CAGCAGCGGAGAGGCAAGGCCCCCAAGCTGCTGATCTACGACGGCAGCAAGCTGGAACGGGGCGTG
CCCAGCCGGTTCAGCGGCAGAAGATGGGGCCAAGAGTACAACCTGACCATCAACAACCTGCAGCCC
GAGGATATTGCCACATACTTTTGCCAGGTGTACGAGTTCGTGGTGCCCGGGACCCGGCTGGATCTG
AAGAGAACCGTGGCCGCTCCCGAGAGCAAATACGGGCCCCCCTGCCCCCCTTGCCCTGCCCCCGAG

-continued
TTCCTGGGCGGACCCAGCGTGTTCCTGTTCCCCCCCAAGCCCAAGGACACCCTGATGATCAGCCGG

ACCCCCGAGGTGACCTGTGTGGTGGTGGACGTGTCCCAGGAGGACCCCGAGGTCCAGTTCAACTGG

TACGTGGACGGCGTGGAGGTGCACAACGCCAAGACCAAGCCCCGGGAGGAGCAGTTCAATAGCACC

TACCGGGTGGTGTCCGTGCTGACCGTGCTGCACCAGGACTGGCTGAACGGCAAGGAATACAAGTGT

AAGGTGTCCAACAAGGGCCTGCCCAGCAGCATCGAGAAAACCATCAGCAAGGCCAAGGGCCAGCCT

CGGGAGCCCCAGGTGTACACCCTGCCCCCTAGCCAAGAGGAGATGACCAAGAACCAGGTGTCCCTG

ACCTGCCTGGTGAAGGGCTTCTACCCCAGCGACATCGCCGTGGAGTGGGAGAGCAACGGCCAGCCC

GAGAACAACTACAAGACCACCCCCCCTGTGCTGGACAGCGACGGCAGCTTCTTCCTGTACAGCCGG

CTGACCGTGGACAAGAGCCGGTGGCAGGAGGGCAACGTCTTTAGCTGCTCCGTGATGCACGAGGCC

CTGCACAACCACTACACCCAGAAGAGCCTGAGCCTGTCCCTGGGCAAGGATATCTACATCTGGGCG

CCCTTGGCCGGGACTTGTGGGGTCCTTCTCCTGTCACTGGTTATCACCCTTTACTGCAAACGGGGC

AGAAAGAAACTCCTGTATATATTCAAACAACCATTTATGAGACCAGTACAAACTACTCAAGAGGAA

GATGGCTGTAGCTGCCGATTTCCAGAAGAAGAAGAAGGAGGATGTGAACTGAGAGTGAAGTTCAGC

AGGAGCGCAGACGCCCCCGCGTACAAGCAGGGCCAGAACCAGCTCTATAACGAGCTCAATCTAGGA

CGAAGAGAGGAGTACGATGTTTTGGACAAGAGACGTGGCCGGGACCCTGAGATGGGGGGAAAGCCG

AGAAGGAAGAACCCTCAGGAAGGCCTGTACAATGAACTGCAGAAAGATAAGATGGCGGAGGCCTAC

AGTGAGATTGGGATGAAAGGCGAGCGCCGGAGGGGCAAGGGGCACGATGGCCTTTACCAGGGTCTC

AGTACAGCCACCAAGGACACCTACGACGCCCTTCACATGCAGGCCCTGCCCCCTCGCTAA

X5 (SEQ ID NO: 27):
ATGCTGCTGCTCGTGACAAGCCTGCTGCTGTGCGAGCTGCCCCACCCCGCCTTTCTGCTGATCCCC

CTGGAACAGTCTGGCGCCGAAGTGAAGAAACCCGGCAGCAGCGTGCAGGTGTCCTGCAAGGCCAGC

GGCGGCACCTTCTCTATGTACGGCTTCAACTGGGTCCGCCAGGCTCCTGGACACGGCCTGGAATGG

ATGGGCGGCATCATCCCCATCTTCGGCACCTCCAACTACGCCCAGAAATTCCGGGGCAGAGTGACC

TTCACCGCCGACCAGGCCACCAGCACCGCCTACATGGAACTGACCAACCTGCGGAGCGACGACACC

GCCGTGTACTACTGCGCCAGAGACTTCGGCCCCGACTGGGAGGACGGCGACAGCTACGATGGCAGC

GGCAGAGGCTTCTTCGACTTCTGGGGCCAGGGCACCCTGGTGACAGTGTCTAGCGGAGGCGGAGGC

TCTGGAGGCGGAGGAAGTGGCGGAGGGGGATCTGAGCTGGTGCTGACCCAGAGCCCTGGCACCCTG

TCTCTGTCTGCCGGCGAGAGAGCCACCCTGAGCTGCAGAGCCAGCCAGAGCGTCTCCAGCGGCAGC

CTGGCCTGGTATCAGCAGAAGCCCGGCCAGGCCCCCAGACTGCTGATCTACGGCGCCAGCACCAGA

GCCACCGGCATCCCCGATAGATTCAGCGGAAGCGGCTCCGGCACCGACTTCACCCTGACCATCGGC

CGGCTGGAACCCGAGGACCTGGCCGTGTATTACTGTCAGCAGTACGGCACCAGCCCCTACACCTTC

GGCCAGGGGACCAAGCTGGAAATCGAGAGCAAATACGGGCCCCCTGCCCCCCTTGCCCTGCCCCC

GAGTTCCTGGGCGGACCCAGCGTGTTCCTGTTCCCCCCCAAGCCCAAGGACACCCTGATGATCAGC

CGGACCCCCGAGGTGACCTGTGTGGTGGTGGACGTGTCCCAGGAGGACCCCGAGGTCCAGTTCAAC

TGGTACGTGGACGGCGTGGAGGTGCACAACGCCAAGACCAAGCCCCGGGAGGAGCAGTTCAATAGC

ACCTACCGGGTGGTGTCCGTGCTGACCGTGCTGCACCAGGACTGGCTGAACGGCAAGGAATACAAG

TGTAAGGTGTCCAACAAGGGCCTGCCCAGCAGCATCGAGAAAACCATCAGCAAGGCCAAGGGCCAG

CCTCGGGAGCCCCAGGTGTACACCCTGCCCCCTAGCCAAGAGGAGATGACCAAGAACCAGGTGTCC

CTGACCTGCCTGGTGAAGGGCTTCTACCCCAGCGACATCGCCGTGGAGTGGGAGAGCAACGGCCAG

CCCGAGAACAACTACAAGACCACCCCCCCTGTGCTGGACAGCGACGGCAGCTTCTTCCTGTACAGC

CGGCTGACCGTGGACAAGAGCCGGTGGCAGGAGGGCAACGTCTTTAGCTGCTCCGTGATGCACGAG

-continued
GCCCTGCACAACCACTACACCCAGAAGAGCCTGAGCCTGTCCCTGGGCAAGGATATCTACATCTGG

GCGCCCTTGGCCGGGACTTGTGGGGTCCTTCTCCTGTCACTGGTTATCACCCTTTACTGCAAACGG

GGCAGAAAGAAACTCCTGTATATATTCAAACAACCATTTATGAGACCAGTACAAACTACTCAAGAG

GAAGATGGCTGTAGCTGCCGATTTCCAGAAGAAGAAGAAGGAGGATGTGAACTGAGAGTGAAGTTC

AGCAGGAGCGCAGACGCCCCCGCGTACAAGCAGGGCCAGAACCAGCTCTATAACGAGCTCAATCTA

GGACGAAGAGAGGAGTACGATGTTTTGGACAAGAGACGTGGCCGGGACCCTGAGATGGGGGGAAAG

CCGAGAAGGAAGAACCCTCAGGAAGGCCTGTACAATGAACTGCAGAAAGATAAGATGGCGGAGGCC

TACAGTGAGATTGGGATGAAAGGCGAGCGCCGGAGGGGCAAGGGCACGATGGCCTTTACCAGGGT

CTCAGTACAGCCACCAAGGACACCTACGACGCCCTTCACATGCAGGCCCTGCCCCCTCGCTAA

PGT126 (SEQ ID NO: 28):
ATGCTGCTGCTGGTGACAAGCCTGCTGCTGTGCGAGCTGCCCCACCCCGCCTTTCTGCTGATCCCC

CAGCCCCAGCTGCAGGAATCTGGCCCTGGCCTGGTGGAAGCCAGCGAGACACTGAGCCTGACCTGC

ACCGTGTCCGGCGATAGCACCGCCGCCTGCGACTACTTTTGGGGCTGGGTGCGCCAGCCTCCTGGC

AAGGGACTGGAATGGATCGGCGGCCTGAGCCACTGCGCCGGCTACTACAACACCGGCTGGACCTAC

CACAACCCCAGCCTCAAGTCCCGGCTGACCATCAGCCTGGACACCCCAAGAACCAGGTGTTCCTG

AAGCTGAACAGCGTGACAGCCGCCGACACCGCCATCTACTACTGCGCCAGATTCGACGGCGAGGTG

CTGGTGTACCACGACTGGCCCAAGCCCGCCTGGGTGGACCTGTGGGCAGAGGCACACTGGTGACA

GTGACCGTGTCTAGCGGCGGAGGCGGAAGCGGAGGTGGAGGATCTGGCGGCGGAGGAAGCCAGTCT

GCCCTGACACAGCCTCCCAGCGCCTCTGGCAGCCCTGGCCAGAGCATCAGCATCAGCTGCACCGGC

ACCAGCAACAGATTCGTGTCCTGGTATCAGCAGCACCCCGGCAAGGCCCCCAAGCTGGTGATCTAC

GGCGTGAACAAGCGGCCCAGCGGCGTGCCCGATCGGTTCAGCGGCAGCAAGAGCGGCAACACCGCC

AGCCTGACAGTGTCCGGCCTGCAGACCGACGACGAGGCCGTGTACTACTGCAGCAGCCTCGTGGGA

AACTGGGACGTGATCTTCGGCGGAGGCACCAAGCTGACCGTGCTGGAGAGCAAATACGGGCCCCCC

TGCCCCCCTTGCCCTGCCCCCGAGTTCCTGGGCGGACCCAGCGTGTTCCTGTTCCCCCCCAAGCCC

AAGGACACCCTGATGATCAGCCGGACCCCCGAGGTGACCTGTGTGGTGGTGGACGTGTCCCAGGAG

GACCCCGAGGTCCAGTTCAACTGGTACGTGGACGGCGTGGAGGTGCACAACGCCAAGACCAAGCCC

CGGGAGGAGCAGTTCAATAGCACCTACCGGGTGGTGTCCGTGCTGACCGTGCTGCACCAGGACTGG

CTGAACGGCAAGGAATACAAGTGTAAGGTGTCCAACAAGGGCCTGCCCAGCAGCATCGAGAAAACC

ATCAGCAAGGCCAAGGGCCAGCCTCGGGAGCCCCAGGTGTACACCCTGCCCCCTAGCCAAGAGGAG

ATGACCAAGAACCAGGTGTCCCTGACCTGCCTGGTGAAGGGCTTCTACCCCAGCGACATCGCCGTG

GAGTGGGAGAGCAACGGCCAGCCCGAGAACAACTACAAGACCACCCCCCCTGTGCTGGACAGCGAC

GGCAGCTTCTTCCTGTACAGCCGGCTGACCGTGGACAAGAGCCGGTGGCAGGAGGGCAACGTCTTT

AGCTGCTCCGTGATGCACGAGGCCCTGCACAACCACTACACCCAGAAGAGCCTGAGCCTGTCCCTG

GGCAAGGATATCTACATCTGGGCGCCCTTGGCCGGGACTTGTGGGGTCCTTCTCCTGTCACTGGTT

ATCACCCTTTACTGCAAACGGGGCAGAAAGAAACTCCTGTATATATTCAAACAACCATTTATGAGA

CCAGTACAAACTACTCAAGAGGAAGATGGCTGTAGCTGCCGATTTCCAGAAGAAGAAGAAGGAGGA

TGTGAACTGAGAGTGAAGTTCAGCAGGAGCGCAGACGCCCCCGCGTACAAGCAGGGCCAGAACCAG

CTCTATAACGAGCTCAATCTAGGACGAAGAGAGGAGTACGATGTTTTGGACAAGAGACGTGGCCGG

GACCCTGAGATGGGGGGAAAGCCGAGAAGGAAGAACCCTCAGGAAGGCCTGTACAATGAACTGCAG

AAAGATAAGATGGCGGAGGCCTACAGTGAGATTGGGATGAAAGGCGAGCGCCGGAGGGGCAAGGGG

-continued

CACGATGGCCTTTACCAGGGTCTCAGTACAGCCACCAAGGACACCTACGACGCCCTTCACATGCAG

GCCCTGCCCCCTCGCTAA

PGT128 (SEQ ID NO: 29):
ATGCTGCTGCTGGTGACAAGCCTGCTGCTGTGCGAGCTGCCCCACCCCGCCTTTCTGCTGATCCCC

CAGCCTCAGCTGCAGGAAAGCGGCCCTACACTGGTGGAAGCCAGCGAGACACTGAGCCTGACCTGC

GCCGTGTCCGGCGATAGCACCGCCGCCTGCAATAGCTTCTGGGGCTGGGTCCGCCAGCCCCCTGGC

AAGGGACTGGAATGGGTGGGAAGCCTGAGCCACTGCGCCAGCTACTGGAACCGGGGCTGGACCTAC

CACAACCCCAGCCTGAAGTCCCGGCTGACCCTGGCCCTGGACACCCCCAAGAACCTGGTGTTCCTG

AAGCTGAACAGCGTGACAGCCGCCGACACCGCCACCTACTACTGCGCCAGATTCGGCGGCGAGGTG

CTGCGGTACACCGACTGGCCTAAGCCCGCCTGGGTGGACCTGTGGGCAGAGGCACCCTGGTGACA

GTGAGTAGCGGCGGAGGCGGAAGCGGTGGAGGGGGATCTGGCGGCGGAGGAAGCCAGTCTGCCCTG

ACACAGCCTCCCAGCGCCTCTGGCAGCCCTGGCCAGAGCATCACCATCAGCTGCACCGGCACCAGC

AACAACTTCGTGTCCTGGTATCAGCAGCACGCCGGCAAGGCCCCCAAGCTGGTGATCTACGACGTG

AACAAGCGGCCCAGCGGCGTGCCCGACAGATTCAGCGGCAGCAAGAGCGGCAACACCGCCAGCCTG

ACCGTGTCTGGCCTGCAGACCGACGACGAGGCCGTGTACTACTGCGCAGCCTCGTGGGAAACTGG

GACGTGATCTTCGGCGGAGGCACCAAGCTGACCGTGCTGGAGAGCAAATACGGGCCCCCCTGCCCC

CCTTGCCCTGCCCCCGAGTTCCTGGGCGGACCCAGCGTGTTCCTGTTCCCCCCCAAGCCCAAGGAC

ACCCTGATGATCAGCCGGACCCCCGAGGTGACCTGTGTGGTGGTGGACGTGTCCCAGGAGGACCCC

GAGGTCCAGTTCAACTGGTACGTGGACGGCGTGGAGGTGCACAACGCCAAGACCAAGCCCCGGGAG

GAGCAGTTCAATAGCACCTACCGGGTGGTGTCCGTGCTGACCGTGCTGCACCAGGACTGGCTGAAC

GGCAAGGAATACAAGTGTAAGGTGTCCAACAAGGGCCTGCCCAGCAGCATCGAGAAAACCATCAGC

AAGGCCAAGGGCCAGCCTCGGGAGCCCCAGGTGTACACCCTGCCCCCTAGCCAAGAGGAGATGACC

AAGAACCAGGTGTCCCTGACCTGCCTGGTGAAGGGCTTCTACCCCAGCGACATCGCCGTGGAGTGG

GAGAGCAACGGCCAGCCCGAGAACAACTACAAGACCACCCCCCCTGTGCTGGACAGCGACGGCAGC

TTCTTCCTGTACAGCCGGCTGACCGTGGACAAGAGCCGGTGGCAGGAGGGCAACGTCTTTAGCTGC

TCCGTGATGCACGAGGCCCTGCACAACCACTACACCCAGAAGAGCCTGAGCCTGTCCCTGGGCAAG

GATATCTACATCTGGGCGCCCTTGGCCGGGACTTGTGGGGTCCTTCTCCTGTCACTGGTTATCACC

CTTTACTGCAAACGGGGCAGAAAGAAACTCCTGTATATATTCAAACAACCATTTATGAGACCAGTA

CAAACTACTCAAGAGGAAGATGGCTGTAGCTGCCGATTTCCAGAAGAAGAAGAAGGAGGATGTGAA

CTGAGAGTGAAGTTCAGCAGGAGCGCAGACGCCCCCGCGTACAAGCAGGGCCAGAACCAGCTCTAT

AACGAGCTCAATCTAGGACGAAGAGAGGAGTACGATGTTTTGGACAAGAGACGTGGCCGGGACCCT

GAGATGGGGGGAAAGCCGAGAAGGAAGAACCCTCAGGAAGGCCTGTACAATGAACTGCAGAAAGAT

AAGATGGCGGAGGCCTACAGTGAGATTGGGATGAAAGGCGAGCGCCGGAGGGGCAAGGGGCACGAT

GGCCTTTACCAGGGTCTCAGTACAGCCACCAAGGACACCTACGACGCCCTTCACATGCAGGCCCTG

CCCCCTCGCTAA

PG9 (SEQ ID NO: 30):
ATGCTGCTGCTGGTGACAAGCCTGCTGCTGTGCGAGCTGCCCCACCCCGCATTTCTGCTGATCCCT

CAGCGGCTGGTGGAAAGCGGAGGCGGAGTGGTGCAGCCCGGGAGCAGCCTGAGACTGTCTTGCGCC

GCCAGCGGCTTCGACTTCAGCCGGCAGGGAATGCACTGGGTGCGCCAGGCTCCAGGCCAGGGACTG

GAATGGGTGGCCTTCATTAAGTACGACGGCAGCGAGAAGTACCACGCCGACAGCGTGTGGGGCAGA

CTGAGCATCAGCCGGGACAACAGCAAGGACACCCTGTACCTGCAGATGAACAGCCTGCGGGTGGAA

GATACCGCCACCTACTTTTGCGTGCGGGAAGCCGGCGGACCCGACTACCGGAACGGCTACAACTAC

-continued

```
TACGACTTCTACGACGGCTACTACAACTACCACTACATGGATGTGTGGGGCAAGGGCACCACCGTG

ACCGTGTCATCTGGCGGCGGAGGATCTGGGGGAGGCGGATCAGGCGGAGGCGGCAGCCAGTCTGCT

CTGACACAGCCTGCCAGCGTCTCCGGCAGCCCTGGCCAGAGCATCACCATCAGCTGCAACGGCACC

AGCAACGACGTGGGCGGCTACGAGAGCGTGTCCTGGTATCAGCAGCACCCCGGCAAGGCCCCCAAG

GTGGTGATCTACGACGTGTCCAAGCGGCCCAGCGGCGTGTCCAACCGGTTCAGCGGCAGCAAGAGC

GGCAACACCGCCAGCCTGACCATCAGCGGACTGCAGGCCGAGGACGAGGGCGACTACTACTGCAAG

AGCCTGACCAGCACCCGGCGGAGAGTGTTCGGCACCGGCACCAAGCTGACCGTGCTGGAGAGCAAA

TACGGGCCCCCCTGCCCCCCTTGCCCTGCCCCCGAGTTCCTGGGCGGACCCAGCGTGTTCCTGTTC

CCCCCCAAGCCCAAGGACACCCTGATGATCAGCCGGACCCCCGAGGTGACCTGTGTGGTGGTGGAC

GTGTCCCAGGAGGACCCCGAGGTCCAGTTCAACTGGTACGTGGACGGCGTGGAGGTGCACAACGCC

AAGACCAAGCCCCGGGAGGAGCAGTTCAATAGCACCTACCGGGTGGTGTCCGTGCTGACCGTGCTG

CACCAGGACTGGCTGAACGGCAAGGAATACAAGTGTAAGGTGTCCAACAAGGGCCTGCCCAGCAGC

ATCGAGAAACCATCAGCAAGGCCAAGGGCCAGCCTCGGGAGCCCCAGGTGTACACCCTGCCCCCT

AGCCAAGAGGAGATGACCAAGAACCAGGTGTCCCTGACCTGCCTGGTGAAGGGCTTCTACCCCAGC

GACATCGCCGTGGAGTGGGAGAGCAACGGCCAGCCCGAGAACAACTACAAGACCACCCCCCCTGTG

CTGGACAGCGACGGCAGCTTCTTCCTGTACAGCCGGCTGACCGTGGACAAGAGCCGGTGGCAGGAG

GGCAACGTCTTTAGCTGCTCCGTGATGCACGAGGCCCTGCACAACCACTACACCCAGAAGAGCCTG

AGCCTGTCCCTGGGCAAGGATATCTACATCTGGGCGCCCTTGGCCGGGACTTGTGGGGTCCTTCTC

CTGTCACTGGTTATCACCCTTTACTGCAAACGGGGCAGAAAGAAACTCCTGTATATATTCAAACAA

CCATTTATGAGACCAGTACAAACTACTCAAGAGGAAGATGGCTGTAGCTGCCGATTTCCAGAAGAA

GAAGAAGGAGGATGTGAACTGAGAGTGAAGTTCAGCAGGAGCGCAGACGCCCCCGCGTACAAGCAG

GGCCAGAACCAGCTCTATAACGAGCTCAATCTAGGACGAAGAGAGGAGTACGATGTTTTGGACAAG

AGACGTGGCCGGGACCCTGAGATGGGGGGAAAGCCGAGAAGGAAGAACCCTCAGGAAGGCCTGTAC

AATGAACTGCAGAAAGATAAGATGGCGGAGGCCTACAGTGAGATTGGGATGAAAGGCGAGCGCCGG

AGGGGCAAGGGGCACGATGGCCTTTACCAGGGTCTCAGTACAGCCACCAAGGACACCTACGACGCC

CTTCACATGCAGGCCCTGCCCCCTCGCTAA
```

10E8 (SEQ ID NO: 31):
```
ATGCTGCTGCTGGTGACAAGCCTGCTGCTGTGCGAGCTGCCCCACCCCGCCTTTCTGCTGATCCCC

GAGGTGCAGCTGGTGGAATCTGGCGGAGGCCTGGTGAAACCTGGCGGCAGCCTGAGACTGAGCTGC

AGCGCCAGCGGCTTCGACTTCGACAACGCCTGGATGACCTGGGTGCGCCAGCCTCCCGGCAAGGGC

CTGGAATGGGTGGGAAGAATCACCGGCCCTGGCGAGGGGTGGTCCGTGGATTATGCCGCCCCTGTG

GAAGGCCGGTTCACCATCAGCAGACTGAACAGCATCAACTTTCTGTACCTGGAAATGAACAACCTG

CGGATGGAAGATAGCGGCCTGTACTTCTGCGCCCGGACCGGCAAGTACTACGACTTTTGGAGCGGC

TACCCCCCTGGCGAAGAGTACTTCCAGGACTGGGGCAGAGGCACCCTGGTGACAGTGTCTAGCGGA

GGCGGAGGCTCTGGCGGCGGAGGAAGTGGCGGAGGCGGGAGCAGCTACGAGCTGACCCAGGAAACA

GGCGTCTCCGTCGCCCTCGGGCGGACCGTGACCATCACCTGTAGAGGCGACAGCCTGCGGAGCCAC

TACGCCAGCTGGTATCAGAAGAAGCCCGGCCAGGCCCCCATCCTGCTGTTCTACGGCAAGAACAAC

CGGCCCAGCGGCGTGCCCGACAGATTCTCTGGCAGCGCCTCCGGCAACCGGGCCAGCCTGACAATT

TCTGGGGCTCAGGCCGAGGACGACGCCGAGTACTACTGCAGCAGCCGGGACAAGAGCGGCAGCAGA

CTGTCTGTGTTCGGCGGAGGCACCAAGCTGACCGTGCTGGAGAGCAAATACGGGCCCCCCTGCCCC

CCTTGCCCTGCCCCCGAGTTCCTGGGCGGACCCAGCGTGTTCCTGTTCCCCCCCAAGCCCAAGGAC
```

-continued

```
ACCCTGATGATCAGCCGGACCCCCGAGGTGACCTGTGTGGTGGTGGACGTGTCCCAGGAGGACCCC

GAGGTCCAGTTCAACTGGTACGTGGACGGCGTGGAGGTGCACAACGCCAAGACCAAGCCCCGGGAG

GAGCAGTTCAATAGCACCTACCGGGTGGTGTCCGTGCTGACCGTGCTGCACCAGGACTGGCTGAAC

GGCAAGGAATACAAGTGTAAGGTGTCCAACAAGGGCCTGCCCAGCAGCATCGAGAAAACCATCAGC

AAGGCCAAGGGCCAGCCTCGGGAGCCCCAGGTGTACACCCTGCCCCCTAGCCAAGAGGAGATGACC

AAGAACCAGGTGTCCCTGACCTGCCTGGTGAAGGGCTTCTACCCCAGCGACATCGCCGTGGAGTGG

GAGAGCAACGGCCAGCCCGAGAACAACTACAAGACCACCCCCCCTGTGCTGGACAGCGACGGCAGC

TTCTTCCTGTACAGCCGGCTGACCGTGGACAAGAGCCGGTGGCAGGAGGGCAACGTCTTTAGCTGC

TCCGTGATGCACGAGGCCCTGCACAACCACTACACCCAGAAGAGCCTGAGCCTGTCCCTGGGCAAG

GATATCTACATCTGGGCGCCCTTGGCCGGGACTTGTGGGGTCCTTCTCCTGTCACTGGTTATCACC

CTTTACTGCAAACGGGGCAGAAAGAAACTCCTGTATATATTCAAACAACCATTTATGAGACCAGTA

CAAACTACTCAAGAGGAAGATGGCTGTAGCTGCCGATTTCCAGAAGAAGAAGAAGGAGGATGTGAA

CTGAGAGTGAAGTTCAGCAGGAGCGCAGACGCCCCGCGTACAAGCAGGGCCAGAACCAGCTCTAT

AACGAGCTCAATCTAGGACGAAGAGAGGAGTACGATGTTTTGGACAAGAGACGTGGCCGGGACCCT

GAGATGGGGGGAAAGCCGAGAAGGAAGAACCCTCAGGAAGGCCTGTACAATGAACTGCAGAAAGAT

AAGATGGCGGAGGCCTACAGTGAGATTGGGATGAAAGGCGAGCGCCGGAGGGGCAAGGGGCACGAT

GGCCTTTACCAGGGTCTCAGTACAGCCACCAAGGACACCTACGACGCCCTTCACATGCAGGCCCTG

CCCCCTCGCTAA
```

Example 2

Transduction of Cells

Because Jurkat cells are very highly permissive for lentiviral vector transduction, the CAR vectors were tested in these cells initially. For Jurkat cells, $10^6$ cells in log phase growth were incubated with the lentiviral vector for four hours with intermittent shaking, washed, and resuspended in fresh R10.

For transduction of primary CD8$^+$ T lymphocytes, polystyrene 6-well plates (BD Biosciences, San Jose, Calif.) were coated with RetroNectin according to the manufacturer's instructions (Takara, Mountain View, Calif.). An aliquot of lentiviral vector was diluted to 500 µl in R10 and placed in a pre-coated well, followed by centrifugation at 2000 g for 2 hours at 32° C. (Sorvall Legend RT, ThermoFisher Scientific, Grand Island, N.Y.). After aspiration of the medium, $10^6$ recently stimulated CD8$^+$ T lymphocytes were added per well in a total volume of 2 ml R10-50. After overnight incubation in a tissue culture incubator, the cells were transferred to fresh R10-50 and cultured for about 7 days before assessment of transduction efficiency.

High titer concentrated lentiviral stocks were produced to transduce primary polyclonal CD8$^+$ T lymphocytes from HIV-1-uninfected donors. Unfortunately, the transduction efficiency was low and required large volumes of supernatant from 293T cell transfections (two or three T150 flasks) to transduce a few million cells and attempts to purify transduced cells by sorting with anti-Human $F_{ab}$ antibody resulted in poor viability. Thus, after transduction of primary CD8$^+$ T lymphocytes with a given CAR vector, the cells were restimulated twice using anti-Human $F_{ab}$ antibody with irradiated allogeneic feeder PBMC and IL-2 as described in Example 3, and each passage was about 10 days. This resulted in selective enrichment of CAR-bearing cells without any cell sorting.

Western Blotting for CD3

To confirm expression of CAR-SCAs in transduced cells, Western blotting for CD3 ζ was performed. Cell lysate from $2\times10^6$ transduced cells was prepared by lysing the cells in lysis buffer (0.5% NP-40, 0.5% sodium deoxycholate, 50 mM NaCl, 25 mM Tris-HCl, 10 mM EDTA) containing 10 mM phenylmethyl sulfonyl (Sigma, St Louis, Mo.) and 1×HALT protease inhibitors (Invitrogen, Carlsbad, Calif.). Proteins were separated by loading 20 µl of the lysate onto a 10% NuPAGE Bis-Tris gel (Invitrogen, Carlsbad, Calif.) and electrophoresis, followed by blotting onto a 0.45 µM PVDF membrane (Millipore, Billerica, Mass.). The membrane was probed using a mouse anti-human CD247 monoclonal antibody (catalog #551033, BD Pharmingen, San Jose, Calif.) and the SuperSignal West Pico Detection Kit (Pierce, Rockford, Ill.).

Flow Cytometry for Cell Surface Single Chain Antibody Expression

To confirm cell surface expression of CAR-SCAs, transduced cells were washed, resuspended in 100 µl of wash buffer (5% BSA with 2 mM EDTA in PBS) containing either FITC-conjugated goat anti-human F(ab)$_2$ antibody (catalog #109-006-003, Jackson ImmunoResearch Laboratories, West Grove, Pa.) or isotype control antibody and incubated for 30 minutes at 4° C. after washing in fresh wash buffer, the cells were fixed in 1% paraformaldehyde and analyzed by flow cytometry (LSR Fortessa II cytometer, BD Biosciences, and FlowJo software, Ashland, Oreg.).

Example 3

Selective Enrichment and Expansion of Cells Transduced with CARs

The following is an exemplary protocol for selectively expanding and enriching cells expressing CAR-SCAs. On Day 0, CAR-transduced CD8$^+$ T cells (7 days post-transduction) were cultured at 5×10$^6$ in a 24-well plate in 1 ml of medium (RPMI 1640 with 10% heat-inactivated fetal calf serum/penicillin-streptomycin/L-glutamine/recombinant human interleukin-2 at 25 IU/ml) with 2×10$^6$ irradiated peripheral blood mononuclear cells and 400 ng/ml of goat anti-human IgG-F(ab)$_2$ (Jackson ImmunoResearch Laboratories, Inc, West Grove, Pa., Cat. #109-006-003). On Day 1, 1 ml of medium was added to the well (to bring the total volume to 2 ml). On Day 4, cells were fed by removing 1 ml supernatant medium (taking care not to disturb the cells settled at the bottom of the well) and replacing with 1 ml fresh medium. On Day 7, the expanding cells (entire 2 ml contents of the well) were transferred to a T25 flask and another 8 ml fresh medium are added. The transduced cells were then counted and used for assessment of purity by, for example, flow cytometry using cell surface staining with the same antibody in a FITC-conjugated version. This protocol can readily be modified for a desired SCA sequence or cell type and/or scaled up to produce commercial size lots of cells expressing CAR-SCAs.

Example 4

Flow Cytometry for CAR-Mediated Proliferation of Transduced CD8+T Lymphocytes in Response to HIV-1-Infected Target Cells HIV-1-infected T2 cells, which are MHC class I low due to a deletion in the transporter associated with processing (TAP) (Salter, et al. (1986) EMBO J 5:943-949) and previously shown to be suitable target cells for an HIV-1-specific CAR (Severino, et al. (2003) Virology 306:371-375), served as target cells. These were infected with an excess of HIV-1 NL4-3-based reporter virus containing a gene for murine CD24 (mCD24) in the vpr locus (Ali, et al. (2003) J Virol Methods 110:137-142) to yield >90% infected cells by 3 or 4 days after infection, as previously described (Bennett, et al. (2007) J Virol 81:4973-4980; Yang, et al. (1996) J Virol 70:5799-5806; and Yang, et al. (1997) J Virol 71:3120-3128). These were irradiated immediately before use with 10,000 rads in a cesium irradiator, as well as peripheral blood mononuclear cells from a healthy donor with 3,000 rads (feeder PBMCs). CAR-SCA transduced primary CD8+ T lymphocytes were labeled with CellTrace Violet and washed according to manufacturer's directions (ThermoFisher Scientific, Grand Island, N.Y.). In a 48 well plate well, 5×10$^5$ labeled transduced cells were added to 5×10$^5$ irradiated infected T2 cells and 2×10$^6$ irradiated feeder PBMCs, and cultured in 1 ml R10-50 for five days with a medium change after three days. Flow cytometry (LSR Fortessa II cytometer, BD Biosciences) was then performed with co-staining for human CD8 (PerCP-anti-human CD8, catalog #30130, Biolegend, San Diego, Calif.) and analysis of proliferation using FlowJo software (FlowJo, Ashland, Oreg.).

Example 5

Virus Suppression Assays

The ability of CAR-SCA transduced CD8+ T lymphocytes and expanded and enriched clones thereof to suppress the replication of HIV-1 was tested as previously described (Yang, et al. (1997) PNAS USA 94:11478-11483; and Yang, et al. (1997) J Virol 71:3120-3128). HIV-1 strains tested were obtained from the NIH AIDS Reference and Reagent including 94US_33931N (catalog #11250), 90 US873 (catalog #11251), 96TH_NP1538 (catalog #11252), 00TZ_A246 (catalog #11256). In brief, T1 cells transduced with human CCR5 were infected at a multiplicity of 0.1 tissue culture infectious doses per cell, and co-cultured in a 96-well plate with CAR-transduced cells at a ratio of 5×10$^4$ to 1.25×10$^4$ cells respectively in 200 μl of R10-50, or no effector cells as a control. The effector cells had been confirmed to be >90% transduced. Each condition was run in triplicate, and viral replication was monitored using p24 quantitative ELISA (XpressBio, Frederick, Md.).

Effector cells expressing CAR-SCAs were also tested for antiviral activity against infected CD4+ cells. T2-CCR5 cells were infected with a panel of HIV-1 strains including primary R5-tropic isolates and cultured in the absence or presence of the CAR-SCA transduced effector cells. Virus replication was assessed by measurement of p24 antigen between days 7 to 10 of culture. Suppression of replication was calculated as the difference of log$_{10}$ units of p24 between cultures without versus with effector cells, which was then normalized as the ratio to total replication without effector cells.

Example 6

Chromium Release Killing Assays for CAR-Mediated Killing of HIV-1-Infected Target Cells T2 cells infected with HIV-1 strain NL4-3 as above were used as target cells for the CAR-SCA transduced primary CD8+ T lymphocytes in standard $^{51}$Cr-release assays as previously described (Bennett, et al. (2007) J Virol 81:4973-4980; Yang, et al. (1996) J Virol 70:5799-5806; and Bennett, et al. (2010) Aids 24:2619-2628). Briefly, infected and control uninfected T2 cells were $^{51}$Cr-labeled for 1 hour and incubated with or without effector CD8+ T lymphocytes for 4 hours at varying cell ratios in a 96-well U-bottom plate. Supernatants were then harvested for measurement of extracellular $^{51}$Cr by micro204-scintillation counting in 96 well plates. Spontaneous release was measured on target cells without effector cells, and maximal release was measured on target cells lysed with 2.5% Triton X-100. Specific lysis was calculated as: (experimental released chromium− spontaneous release)÷(maximal release− spontaneous release).

As used herein, "specifically binds" refers to a specific binding agent's preferential interaction with a given ligand over other agents in a sample. For example, a specific binding agent that specifically binds a given ligand, binds the given ligand, under suitable conditions, in an amount or a degree that is observable over that of any nonspecific interaction with other components in the sample. Suitable conditions are those that allow interaction between a given specific binding agent and a given ligand. These conditions include pH, temperature, concentration, solvent, time of incubation, and the like, and may differ among given specific binding agent and ligand pairs, but may be readily determined by those skilled in the art.

As used herein, the term percent sequence "identity" refers to two or more sequences or subsequences that have a specified percentage of nucleotides or amino acid residues that are the same, when compared and aligned for maximum correspondence, as measured using one of the sequence comparison algorithms described below (e.g., BLASTP and BLASTN or other algorithms available to persons of skill) or by visual inspection. Depending on the application, the percent "identity" can exist over a region of the sequence being compared, e.g., over a functional domain, or, alternatively, exist over the full length of the two sequences to be compared.

For sequence comparison, typically one sequence acts as a reference sequence to which test sequences are compared.

When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, PNAS USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection.

One example of an algorithm that is suitable for determining percent sequence identity and sequence similarity is the BLAST algorithm, which is described in Altschul et al., J. Mol. Biol. 215:403-410 (1990). Software for performing BLAST analyses is publicly available through the National Center for Biotechnology Information (ncbi.nlm.nih.gov).

As used herein, the terms "individual", "subject", "host", and "patient", are used interchangeably to refer to humans and non-human animals. The term "non-human animal" includes all vertebrates, e.g., mammals and non-mammals, such as non-human primates, humans, canines, felines, ungulates (e.g., equines, bovines, ovines, porcines, and caprines), rodents, and other veterinary subjects and test animals.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

As used in the specification and the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely", "only", and the like in connection with the recitation of claim elements, or use of a "negative" limitation.

The use of "or" includes "and/or" unless the context dictates otherwise. As used herein, "and/or" means "and" or "or". For example, "A and/or B" means "A, B, or both A and B" and "A, B, C, and/or D" means "A, B, C, D, or a combination thereof" and said "combination thereof" means any subset of A, B, C, and D, for example, a single member subset (e.g., A or B or C or D), a two-member subset (e.g., A and B; A and C; etc.), or a three-member subset (e.g., A, B, and C; or A, B, and D; etc.), or all four members (e.g., A, B, C, and D).

To the extent necessary to understand or complete the disclosure of the present invention, all publications, patents, and patent applications mentioned herein are expressly incorporated by reference therein to the same extent as though each were individually so incorporated.

Having thus described exemplary embodiments of the present invention, it should be noted by those skilled in the art that the within disclosures are exemplary only and that various other alternatives, adaptations, and modifications may be made within the scope of the present invention. Accordingly, the present invention is not limited to the specific embodiments as illustrated herein, but is only limited by the following claims.

---

What is claimed is:

1. A method of expanding and enriching cells expressing a chimeric antigen receptor (CAR) comprising a single chain antibody domain (SCA), which comprises contacting the cells with an antibody that binds the SCA domain while culturing the cells to thereby expand and enrich cells expressing the CAR, wherein the SCA comprises:
- a first amino acid sequence having at least 95% sequence identity to a sequence selected from the group consisting of SEQ ID NO: 5, SEQ ID NO: 8, SEQ ID NO: 11, SEQ ID NO: 14, SEQ ID NO: 17, SEQ ID NO: 20, and SEQ ID NO: 23; and
- a second amino acid sequence having at least 95% sequence identity to a sequence selected from the group consisting of SEQ ID NO: 6, SEQ ID NO: 9, SEQ ID NO: 12, SEQ ID NO: 15, SEQ ID NO: 18, SEQ ID NO: 21, and SEQ ID NO: 24.

2. The method according to claim 1, wherein the antibody binds the CAR with a higher binding affinity than any endogenous T cell receptors expressed by the cells.

3. The method according to claim 1, wherein the antibody is an anti-human Fab antibody.

4. The method according to claim 3, wherein the antibody is a non-human antibody.

5. The method according to claim 1, wherein the antibody is an anti-IgG antibody.

6. The method according to claim 1, wherein the cells are cultured for at least one cell passage.

7. The method according to claim 1, wherein the cells are T cells.

8. The method according to claim 7, wherein the T cells are CD8+ T cells.

9. A composition comprising one or more expanded and/or enriched cells produced according to claim 1.

10. The composition according to claim 9, wherein the one or more expanded and/or enriched cells comprise least about 50% of the total cells in the composition.

11. A method of treating an HIV infection in a subject which comprises administering to the subject a therapeutically effective amount of one or more expanded and/or enriched cells produced according to claim 1 thereby treating the subject for the HIV infection.

12. The method according to claim 1, wherein the SCA comprises
SEQ ID NO: 5 and SEQ ID NO: 6;
SEQ ID NO: 8 and SEQ ID NO: 9;
SEQ ID NO: 11 and SEQ ID NO: 12;
SEQ ID NO: 14 and SEQ ID NO: 15;
SEQ ID NO: 17 and SEQ ID NO: 18;
SEQ ID NO: 20 and SEQ ID NO: 21; or
SEQ ID NO: 23 and SEQ ID NO: 24.

* * * * *

SEQUENCE LISTING

```
<160> NUMBER OF SEQ ID NOS: 31

<210> SEQ ID NO 1
<211> LENGTH: 22
<212> TYPE: PRT
<213> ORGANISM: Artificial Sequence
<220> FEATURE:
<223> OTHER INFORMATION: Signal sequence of CAR-SCA having SCA sequence
      based on antibody sequence against HIV.

<400> SEQUENCE: 1

Met Leu Leu Leu Val Thr Ser Leu Leu Leu Cys Glu Leu Pro His Pro
1               5                   10                  15

Ala Phe Leu Leu Ile Pro
            20

<210> SEQ ID NO 2
<211> LENGTH: 15
<212> TYPE: PRT
<213> ORGANISM: Artificial Sequence
<220> FEATURE:
<223> OTHER INFORMATION: Linker sequence of CAR-SCA having SCA sequence
      based on antibody sequence against HIV.

<400> SEQUENCE: 2

Gly Gly Gly Gly Ser Gly Gly Gly Gly Ser Gly Gly Gly Gly Ser
1               5                   10                  15
```

<210> SEQ ID NO 3
<211> LENGTH: 408
<212> TYPE: PRT
<213> ORGANISM: Artificial Sequence
<220> FEATURE:
<223> OTHER INFORMATION: Transmembrane/signaling domain of CAR-SCA having SCA sequence based on antibody sequence against HIV.

<400> SEQUENCE: 3

```
Glu Ser Lys Tyr Gly Pro Pro Cys Pro Pro Cys Pro Ala Pro Glu Phe
1               5                   10                  15

Leu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Ser Gln Glu Glu Met Thr Lys Asn Gln
    130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
    210                 215                 220

Leu Ser Leu Gly Lys Asp Ile Tyr Ile Trp Ala Pro Leu Ala Gly Thr
225                 230                 235                 240

Cys Gly Val Leu Leu Leu Ser Leu Val Ile Thr Leu Tyr Cys Lys Arg
                245                 250                 255

Gly Arg Lys Lys Leu Leu Tyr Ile Phe Lys Gln Pro Phe Met Arg Pro
            260                 265                 270

Val Gln Thr Thr Gln Glu Glu Asp Gly Cys Ser Cys Arg Phe Pro Glu
        275                 280                 285

Glu Glu Glu Gly Gly Cys Glu Leu Arg Val Lys Phe Ser Arg Ser Ala
    290                 295                 300

Asp Ala Pro Ala Tyr Lys Gln Gly Gln Asn Gln Leu Tyr Asn Glu Leu
305                 310                 315                 320

Asn Leu Gly Arg Arg Glu Glu Tyr Asp Val Leu Asp Lys Arg Arg Gly
                325                 330                 335

Arg Asp Pro Glu Met Gly Gly Lys Pro Arg Arg Lys Asn Pro Gln Glu
            340                 345                 350

Gly Leu Tyr Asn Glu Leu Gln Lys Asp Lys Met Ala Glu Ala Tyr Ser
        355                 360                 365
```

Glu Ile Gly Met Lys Gly Glu Arg Arg Arg Gly Lys Gly His Asp Gly
    370             375                 380

Leu Tyr Gln Gly Leu Ser Thr Ala Thr Lys Asp Thr Tyr Asp Ala Leu
385                 390                 395                 400

His Met Gln Ala Leu Pro Pro Arg
                405

<210> SEQ ID NO 4
<211> LENGTH: 670
<212> TYPE: PRT
<213> ORGANISM: Artificial Sequence
<220> FEATURE:
<223> OTHER INFORMATION: CAR-SCA having SCA sequence based on antibody
      sequence against HIV.

<400> SEQUENCE: 4

Met Leu Leu Leu Val Thr Ser Leu Leu Leu Cys Glu Leu Pro His Pro
1               5                   10                  15

Ala Phe Leu Leu Ile Pro Gln Val Gln Leu Val Gln Ser Gly Gly Gln
            20                  25                  30

Met Lys Lys Pro Gly Glu Ser Met Arg Ile Ser Cys Arg Ala Ser Gly
        35                  40                  45

Tyr Glu Phe Ile Asp Cys Thr Leu Asn Trp Ile Arg Leu Ala Pro Gly
    50                  55                  60

Lys Arg Pro Glu Trp Met Gly Trp Leu Lys Pro Arg Gly Gly Ala Val
65                  70                  75                  80

Asn Tyr Ala Arg Pro Leu Gln Gly Arg Val Thr Met Thr Arg Asp Val
                85                  90                  95

Tyr Ser Asp Thr Ala Phe Leu Glu Leu Arg Ser Leu Thr Val Asp Asp
            100                 105                 110

Thr Ala Val Tyr Phe Cys Thr Arg Gly Lys Asn Cys Asp Tyr Asn Trp
        115                 120                 125

Asp Phe Glu His Trp Gly Arg Gly Thr Pro Val Ile Val Ser Ser Gly
    130                 135                 140

Gly Gly Gly Ser Gly Gly Gly Gly Ser Gly Gly Gly Gly Ser Glu Ile
145                 150                 155                 160

Val Leu Thr Gln Ser Pro Gly Thr Leu Ser Leu Ser Pro Gly Glu Thr
                165                 170                 175

Ala Ile Ile Ser Cys Arg Thr Ser Gln Tyr Gly Ser Leu Ala Trp Tyr
            180                 185                 190

Gln Gln Arg Pro Gly Gln Ala Pro Arg Leu Val Ile Tyr Ser Gly Ser
        195                 200                 205

Thr Arg Ala Ala Gly Ile Pro Asp Arg Phe Ser Gly Ser Arg Trp Gly
    210                 215                 220

Pro Asp Tyr Asn Leu Thr Ile Ser Asn Leu Glu Ser Gly Asp Phe Gly
225                 230                 235                 240

Val Tyr Tyr Cys Gln Gln Tyr Glu Phe Phe Gly Gln Gly Thr Lys Val
                245                 250                 255

Gln Val Asp Ile Lys Arg Glu Ser Lys Tyr Gly Pro Pro Cys Pro Pro
            260                 265                 270

Cys Pro Ala Pro Glu Phe Leu Gly Gly Pro Ser Val Phe Leu Phe Pro
        275                 280                 285

Pro Lys Pro Lys Asp Thr Leu Met Ile Ser Arg Thr Pro Glu Val Thr
    290                 295                 300

Cys Val Val Val Asp Val Ser Gln Glu Asp Pro Glu Val Gln Phe Asn
305                 310                 315                 320

Trp Tyr Val Asp Gly Val Glu Val His Asn Ala Lys Thr Lys Pro Arg
                325                 330                 335

Glu Glu Gln Phe Asn Ser Thr Tyr Arg Val Val Ser Val Leu Thr Val
            340                 345                 350

Leu His Gln Asp Trp Leu Asn Gly Lys Glu Tyr Lys Cys Lys Val Ser
        355                 360                 365

Asn Lys Gly Leu Pro Ser Ser Ile Glu Lys Thr Ile Ser Lys Ala Lys
    370                 375                 380

Gly Gln Pro Arg Glu Pro Gln Val Tyr Thr Leu Pro Pro Ser Gln Glu
385                 390                 395                 400

Glu Met Thr Lys Asn Gln Val Ser Leu Thr Cys Leu Val Lys Gly Phe
            405                 410                 415

Tyr Pro Ser Asp Ile Ala Val Glu Trp Glu Ser Asn Gly Gln Pro Glu
        420                 425                 430

Asn Asn Tyr Lys Thr Thr Pro Pro Val Leu Asp Ser Asp Gly Ser Phe
    435                 440                 445

Phe Leu Tyr Ser Arg Leu Thr Val Asp Lys Ser Arg Trp Gln Glu Gly
450                 455                 460

Asn Val Phe Ser Cys Ser Val Met His Glu Ala Leu His Asn His Tyr
465                 470                 475                 480

Thr Gln Lys Ser Leu Ser Leu Ser Leu Gly Lys Asp Ile Tyr Ile Trp
            485                 490                 495

Ala Pro Leu Ala Gly Thr Cys Gly Val Leu Leu Leu Ser Leu Val Ile
        500                 505                 510

Thr Leu Tyr Cys Lys Arg Gly Arg Lys Lys Leu Leu Tyr Ile Phe Lys
    515                 520                 525

Gln Pro Phe Met Arg Pro Val Gln Thr Thr Gln Glu Glu Asp Gly Cys
530                 535                 540

Ser Cys Arg Phe Pro Glu Glu Glu Glu Gly Gly Cys Glu Leu Arg Val
545                 550                 555                 560

Lys Phe Ser Arg Ser Ala Asp Ala Pro Ala Tyr Lys Gln Gly Gln Asn
            565                 570                 575

Gln Leu Tyr Asn Glu Leu Asn Leu Gly Arg Arg Glu Glu Tyr Asp Val
        580                 585                 590

Leu Asp Lys Arg Arg Gly Arg Asp Pro Glu Met Gly Gly Lys Pro Arg
    595                 600                 605

Arg Lys Asn Pro Gln Glu Gly Leu Tyr Asn Glu Leu Gln Lys Asp Lys
610                 615                 620

Met Ala Glu Ala Tyr Ser Glu Ile Gly Met Lys Gly Glu Arg Arg Arg
625                 630                 635                 640

Gly Lys Gly His Asp Gly Leu Tyr Gln Gly Leu Ser Thr Ala Thr Lys
            645                 650                 655

Asp Thr Tyr Asp Ala Leu His Met Gln Ala Leu Pro Pro Arg
        660                 665                 670

<210> SEQ ID NO 5
<211> LENGTH: 121
<212> TYPE: PRT
<213> ORGANISM: Artificial Sequence
<220> FEATURE:
<223> OTHER INFORMATION: VH sequence of CAR-SCA having SCA sequence
      based on antibody sequence against HIV.

<400> SEQUENCE: 5

```
Gln Val Gln Leu Val Gln Ser Gly Gly Gln Met Lys Lys Pro Gly Glu
1               5                   10                  15

Ser Met Arg Ile Ser Cys Arg Ala Ser Gly Tyr Glu Phe Ile Asp Cys
            20                  25                  30

Thr Leu Asn Trp Ile Arg Leu Ala Pro Gly Lys Arg Pro Glu Trp Met
        35                  40                  45

Gly Trp Leu Lys Pro Arg Gly Gly Ala Val Asn Tyr Ala Arg Pro Leu
    50                  55                  60

Gln Gly Arg Val Thr Met Thr Arg Asp Val Tyr Ser Asp Thr Ala Phe
65                  70                  75                  80

Leu Glu Leu Arg Ser Leu Thr Val Asp Asp Thr Ala Val Tyr Phe Cys
                85                  90                  95

Thr Arg Gly Lys Asn Cys Asp Tyr Asn Trp Asp Phe Glu His Trp Gly
            100                 105                 110

Arg Gly Thr Pro Val Ile Val Ser Ser
        115                 120
```

<210> SEQ ID NO 6
<211> LENGTH: 104
<212> TYPE: PRT
<213> ORGANISM: Artificial Sequence
<220> FEATURE:
<223> OTHER INFORMATION: VL sequence of CAR-SCA having SCA sequence
      based on antibody sequence against HIV.

<400> SEQUENCE: 6

```
Glu Ile Val Leu Thr Gln Ser Pro Gly Thr Leu Ser Leu Ser Pro Gly
1               5                   10                  15

Glu Thr Ala Ile Ile Ser Cys Arg Thr Ser Gln Tyr Gly Ser Leu Ala
            20                  25                  30

Trp Tyr Gln Gln Arg Pro Gly Gln Ala Pro Arg Leu Val Ile Tyr Ser
        35                  40                  45

Gly Ser Thr Arg Ala Ala Gly Ile Pro Asp Arg Phe Ser Gly Ser Arg
    50                  55                  60

Trp Gly Pro Asp Tyr Asn Leu Thr Ile Ser Asn Leu Glu Ser Gly Asp
65                  70                  75                  80

Phe Gly Val Tyr Tyr Cys Gln Gln Tyr Glu Phe Phe Gly Gln Gly Thr
                85                  90                  95

Lys Val Gln Val Asp Ile Lys Arg
            100
```

<210> SEQ ID NO 7
<211> LENGTH: 679
<212> TYPE: PRT
<213> ORGANISM: Artificial Sequence
<220> FEATURE:
<223> OTHER INFORMATION: CAR-SCA having SCA sequence based on antibody
      sequence against HIV.

<400> SEQUENCE: 7

```
Met Leu Leu Leu Val Thr Ser Leu Leu Cys Glu Leu Pro His Pro
1               5                   10                  15

Ala Phe Leu Leu Ile Pro Gln Val Gln Leu Leu Gln Ser Gly Ala Ala
            20                  25                  30

Val Thr Lys Pro Gly Ala Ser Val Arg Val Ser Cys Glu Ala Ser Gly
        35                  40                  45
```

```
Tyr Asn Ile Arg Asp Tyr Phe Ile His Trp Trp Arg Gln Ala Pro Gly
     50                  55                  60

Gln Gly Leu Gln Trp Val Gly Trp Ile Asn Pro Lys Thr Gly Gln Pro
 65                  70                  75                  80

Asn Asn Pro Arg Gln Phe Gln Gly Arg Val Ser Leu Thr Arg His Ala
                 85                  90                  95

Ser Trp Asp Phe Asp Thr Phe Ser Phe Tyr Met Asp Leu Lys Ala Leu
                100                 105                 110

Arg Ser Asp Asp Thr Ala Val Tyr Phe Cys Ala Arg Gln Arg Ser Asp
                115                 120                 125

Tyr Trp Asp Phe Asp Val Trp Gly Ser Gly Thr Gln Val Thr Val Ser
            130                 135                 140

Ser Ala Ser Thr Lys Gly Pro Gly Gly Gly Ser Gly Gly Gly Gly
145                 150                 155                 160

Ser Gly Gly Gly Gly Ser Asp Ile Gln Met Thr Gln Ser Pro Ser Ser
                165                 170                 175

Leu Ser Ala Ser Val Gly Asp Thr Val Thr Ile Thr Cys Gln Ala Asn
            180                 185                 190

Gly Tyr Leu Asn Trp Tyr Gln Gln Arg Arg Gly Lys Ala Pro Lys Leu
            195                 200                 205

Leu Ile Tyr Asp Gly Ser Lys Leu Glu Arg Gly Val Pro Ser Arg Phe
210                 215                 220

Ser Gly Arg Arg Trp Gly Gln Glu Tyr Asn Leu Thr Ile Asn Asn Leu
225                 230                 235                 240

Gln Pro Glu Asp Ile Ala Thr Tyr Phe Cys Gln Val Tyr Glu Phe Val
                245                 250                 255

Val Pro Gly Thr Arg Leu Asp Leu Lys Arg Thr Val Ala Ala Pro Glu
            260                 265                 270

Ser Lys Tyr Gly Pro Pro Cys Pro Pro Cys Pro Ala Pro Glu Phe Leu
            275                 280                 285

Gly Gly Pro Ser Val Phe Leu Phe Pro Pro Lys Pro Lys Asp Thr Leu
290                 295                 300

Met Ile Ser Arg Thr Pro Glu Val Thr Cys Val Val Val Asp Val Ser
305                 310                 315                 320

Gln Glu Asp Pro Glu Val Gln Phe Asn Trp Tyr Val Asp Gly Val Glu
                325                 330                 335

Val His Asn Ala Lys Thr Lys Pro Arg Glu Glu Gln Phe Asn Ser Thr
            340                 345                 350

Tyr Arg Val Val Ser Val Leu Thr Val Leu His Gln Asp Trp Leu Asn
            355                 360                 365

Gly Lys Glu Tyr Lys Cys Lys Val Ser Asn Lys Gly Leu Pro Ser Ser
370                 375                 380

Ile Glu Lys Thr Ile Ser Lys Ala Lys Gly Gln Pro Arg Glu Pro Gln
385                 390                 395                 400

Val Tyr Thr Leu Pro Pro Ser Gln Glu Glu Met Thr Lys Asn Gln Val
                405                 410                 415

Ser Leu Thr Cys Leu Val Lys Gly Phe Tyr Pro Ser Asp Ile Ala Val
            420                 425                 430

Glu Trp Glu Ser Asn Gly Gln Pro Glu Asn Asn Tyr Lys Thr Thr Pro
            435                 440                 445

Pro Val Leu Asp Ser Asp Gly Ser Phe Phe Leu Tyr Ser Arg Leu Thr
450                 455                 460
```

Val Asp Lys Ser Arg Trp Gln Glu Gly Asn Val Phe Ser Cys Ser Val
465                 470                 475                 480

Met His Glu Ala Leu His Asn His Tyr Thr Gln Lys Ser Leu Ser Leu
            485                 490                 495

Ser Leu Gly Lys Asp Ile Tyr Ile Trp Ala Pro Leu Ala Gly Thr Cys
            500                 505                 510

Gly Val Leu Leu Leu Ser Leu Val Ile Thr Leu Tyr Cys Lys Arg Gly
            515                 520                 525

Arg Lys Lys Leu Leu Tyr Ile Phe Lys Gln Pro Phe Met Arg Pro Val
            530                 535                 540

Gln Thr Thr Gln Glu Glu Asp Gly Cys Ser Cys Arg Phe Pro Glu Glu
545                 550                 555                 560

Glu Glu Gly Gly Cys Glu Leu Arg Val Lys Phe Ser Arg Ser Ala Asp
            565                 570                 575

Ala Pro Ala Tyr Lys Gln Gly Gln Asn Gln Leu Tyr Asn Glu Leu Asn
            580                 585                 590

Leu Gly Arg Arg Glu Glu Tyr Asp Val Leu Asp Lys Arg Arg Gly Arg
595                 600                 605

Asp Pro Glu Met Gly Gly Lys Pro Arg Arg Lys Asn Pro Gln Glu Gly
610                 615                 620

Leu Tyr Asn Glu Leu Gln Lys Asp Lys Met Ala Glu Ala Tyr Ser Glu
625                 630                 635                 640

Ile Gly Met Lys Gly Glu Arg Arg Arg Gly Lys Gly His Asp Gly Leu
            645                 650                 655

Tyr Gln Gly Leu Ser Thr Ala Thr Lys Asp Thr Tyr Asp Ala Leu His
            660                 665                 670

Met Gln Ala Leu Pro Pro Arg
            675

<210> SEQ ID NO 8
<211> LENGTH: 129
<212> TYPE: PRT
<213> ORGANISM: Artificial Sequence
<220> FEATURE:
<223> OTHER INFORMATION: VH sequence of CAR-SCA having SCA sequence
      based on antibody sequence against HIV.

<400> SEQUENCE: 8

Gln Val Gln Leu Leu Gln Ser Gly Ala Ala Val Thr Lys Pro Gly Ala
1               5                   10                  15

Ser Val Arg Val Ser Cys Glu Ala Ser Gly Tyr Asn Ile Arg Asp Tyr
            20                  25                  30

Phe Ile His Trp Trp Arg Gln Ala Pro Gly Gln Gly Leu Gln Trp Val
            35                  40                  45

Gly Trp Ile Asn Pro Lys Thr Gly Gln Pro Asn Asn Pro Arg Gln Phe
        50                  55                  60

Gln Gly Arg Val Ser Leu Thr Arg His Ala Ser Trp Asp Phe Asp Thr
65                  70                  75                  80

Phe Ser Phe Tyr Met Asp Leu Lys Ala Leu Arg Ser Asp Asp Thr Ala
            85                  90                  95

Val Tyr Phe Cys Ala Arg Gln Arg Ser Asp Tyr Trp Asp Phe Asp Val
            100                 105                 110

Trp Gly Ser Gly Thr Gln Val Thr Val Ser Ser Ala Ser Thr Lys Gly
            115                 120                 125

Pro

<210> SEQ ID NO 9
<211> LENGTH: 105
<212> TYPE: PRT
<213> ORGANISM: Artificial Sequence
<220> FEATURE:
<223> OTHER INFORMATION: VL sequence of CAR-SCA having SCA sequence
      based on antibody sequence against HIV.

<400> SEQUENCE: 9

```
Asp Ile Gln Met Thr Gln Ser Pro Ser Ser Leu Ser Ala Ser Val Gly
1               5                   10                  15

Asp Thr Val Thr Ile Thr Cys Gln Ala Asn Gly Tyr Leu Asn Trp Tyr
            20                  25                  30

Gln Gln Arg Arg Gly Lys Ala Pro Lys Leu Leu Ile Tyr Asp Gly Ser
        35                  40                  45

Lys Leu Glu Arg Gly Val Pro Ser Arg Phe Ser Gly Arg Arg Trp Gly
50                  55                  60

Gln Glu Tyr Asn Leu Thr Ile Asn Asn Leu Gln Pro Glu Asp Ile Ala
65                  70                  75                  80

Thr Tyr Phe Cys Gln Val Tyr Glu Phe Val Val Pro Gly Thr Arg Leu
                85                  90                  95

Asp Leu Lys Arg Thr Val Ala Ala Pro
            100                 105
```

<210> SEQ ID NO 10
<211> LENGTH: 680
<212> TYPE: PRT
<213> ORGANISM: Artificial Sequence
<220> FEATURE:
<223> OTHER INFORMATION: CAR-SCA having SCA sequence based on antibody
      sequence against HIV.

<400> SEQUENCE: 10

```
Met Leu Leu Leu Val Thr Ser Leu Leu Leu Cys Glu Leu Pro His Pro
1               5                   10                  15

Ala Phe Leu Leu Ile Pro Leu Glu Gln Ser Gly Ala Glu Val Lys Lys
            20                  25                  30

Pro Gly Ser Ser Val Gln Val Ser Cys Lys Ala Ser Gly Gly Thr Phe
        35                  40                  45

Ser Met Tyr Gly Phe Asn Trp Val Arg Gln Ala Pro Gly His Gly Leu
50                  55                  60

Glu Trp Met Gly Gly Ile Ile Pro Ile Phe Gly Thr Ser Asn Tyr Ala
65                  70                  75                  80

Gln Lys Phe Arg Gly Arg Val Thr Phe Thr Ala Asp Gln Ala Thr Ser
                85                  90                  95

Thr Ala Tyr Met Glu Leu Thr Asn Leu Arg Ser Asp Asp Thr Ala Val
            100                 105                 110

Tyr Tyr Cys Ala Arg Asp Phe Gly Pro Asp Trp Glu Asp Gly Asp Ser
        115                 120                 125

Tyr Asp Gly Ser Gly Arg Gly Phe Phe Asp Phe Trp Gly Gln Gly Thr
130                 135                 140

Leu Val Thr Val Ser Ser Gly Gly Gly Ser Gly Gly Gly Gly Ser
145                 150                 155                 160

Gly Gly Gly Gly Ser Glu Leu Val Leu Thr Gln Ser Pro Gly Thr Leu
                165                 170                 175

Ser Leu Ser Ala Gly Glu Arg Ala Thr Leu Ser Cys Arg Ala Ser Gln
            180                 185                 190
```

```
Ser Val Ser Ser Gly Ser Leu Ala Trp Tyr Gln Gln Lys Pro Gly Gln
            195                 200                 205

Ala Pro Arg Leu Leu Ile Tyr Gly Ala Ser Thr Arg Ala Thr Gly Ile
210                 215                 220

Pro Asp Arg Phe Ser Gly Ser Gly Ser Gly Thr Asp Phe Thr Leu Thr
225                 230                 235                 240

Ile Gly Arg Leu Glu Pro Glu Asp Leu Ala Val Tyr Cys Gln Gln
                245                 250                 255

Tyr Gly Thr Ser Pro Tyr Thr Phe Gly Gln Gly Thr Lys Leu Glu Ile
            260                 265                 270

Glu Ser Lys Tyr Gly Pro Pro Cys Pro Pro Cys Pro Ala Pro Glu Phe
        275                 280                 285

Leu Gly Gly Pro Ser Val Phe Leu Phe Pro Pro Lys Pro Lys Asp Thr
290                 295                 300

Leu Met Ile Ser Arg Thr Pro Glu Val Thr Cys Val Val Val Asp Val
305                 310                 315                 320

Ser Gln Glu Asp Pro Glu Val Gln Phe Asn Trp Tyr Val Asp Gly Val
                325                 330                 335

Glu Val His Asn Ala Lys Thr Lys Pro Arg Glu Glu Gln Phe Asn Ser
            340                 345                 350

Thr Tyr Arg Val Val Ser Val Leu Thr Val Leu His Gln Asp Trp Leu
        355                 360                 365

Asn Gly Lys Glu Tyr Lys Cys Lys Val Ser Asn Lys Gly Leu Pro Ser
        370                 375                 380

Ser Ile Glu Lys Thr Ile Ser Lys Ala Lys Gly Gln Pro Arg Glu Pro
385                 390                 395                 400

Gln Val Tyr Thr Leu Pro Pro Ser Gln Glu Met Thr Lys Asn Gln
                405                 410                 415

Val Ser Leu Thr Cys Leu Val Lys Gly Phe Tyr Pro Ser Asp Ile Ala
            420                 425                 430

Val Glu Trp Glu Ser Asn Gly Gln Pro Glu Asn Asn Tyr Lys Thr Thr
        435                 440                 445

Pro Pro Val Leu Asp Ser Asp Gly Ser Phe Phe Leu Tyr Ser Arg Leu
450                 455                 460

Thr Val Asp Lys Ser Arg Trp Gln Glu Gly Asn Val Phe Ser Cys Ser
465                 470                 475                 480

Val Met His Glu Ala Leu His Asn His Tyr Thr Gln Lys Ser Leu Ser
                485                 490                 495

Leu Ser Leu Gly Lys Asp Ile Tyr Ile Trp Ala Pro Leu Ala Gly Thr
            500                 505                 510

Cys Gly Val Leu Leu Leu Ser Leu Val Ile Thr Leu Tyr Cys Lys Arg
        515                 520                 525

Gly Arg Lys Lys Leu Leu Tyr Ile Phe Lys Gln Pro Phe Met Arg Pro
        530                 535                 540

Val Gln Thr Thr Gln Glu Glu Asp Gly Cys Ser Cys Arg Phe Pro Glu
545                 550                 555                 560

Glu Glu Glu Gly Gly Cys Glu Leu Arg Val Lys Phe Ser Arg Ser Ala
                565                 570                 575

Asp Ala Pro Ala Tyr Lys Gln Gly Gln Asn Gln Leu Tyr Asn Glu Leu
            580                 585                 590

Asn Leu Gly Arg Arg Glu Glu Tyr Asp Val Leu Asp Lys Arg Arg Gly
        595                 600                 605
```

-continued

```
Arg Asp Pro Glu Met Gly Gly Lys Pro Arg Arg Lys Asn Pro Gln Glu
        610                 615                 620
Gly Leu Tyr Asn Glu Leu Gln Lys Asp Lys Met Ala Glu Ala Tyr Ser
625                 630                 635                 640
Glu Ile Gly Met Lys Gly Glu Arg Arg Arg Gly Lys Gly His Asp Gly
                645                 650                 655
Leu Tyr Gln Gly Leu Ser Thr Ala Thr Lys Asp Thr Tyr Asp Ala Leu
            660                 665                 670
His Met Gln Ala Leu Pro Pro Arg
        675                 680

<210> SEQ ID NO 11
<211> LENGTH: 128
<212> TYPE: PRT
<213> ORGANISM: Artificial Sequence
<220> FEATURE:
<223> OTHER INFORMATION: VH sequence of CAR-SCA having SCA sequence
      based on antibody sequence against HIV.

<400> SEQUENCE: 11

Leu Glu Gln Ser Gly Ala Glu Val Lys Lys Pro Gly Ser Ser Val Gln
1               5                   10                  15
Val Ser Cys Lys Ala Ser Gly Gly Thr Phe Ser Met Tyr Gly Phe Asn
            20                  25                  30
Trp Val Arg Gln Ala Pro Gly His Gly Leu Glu Trp Met Gly Gly Ile
        35                  40                  45
Ile Pro Ile Phe Gly Thr Ser Asn Tyr Ala Gln Lys Phe Arg Gly Arg
    50                  55                  60
Val Thr Phe Thr Ala Asp Gln Ala Thr Ser Thr Ala Tyr Met Glu Leu
65                  70                  75                  80
Thr Asn Leu Arg Ser Asp Asp Thr Ala Val Tyr Tyr Cys Ala Arg Asp
                85                  90                  95
Phe Gly Pro Asp Trp Glu Asp Gly Asp Ser Tyr Asp Gly Ser Gly Arg
            100                 105                 110
Gly Phe Phe Asp Phe Trp Gly Gln Gly Thr Leu Val Thr Val Ser Ser
        115                 120                 125

<210> SEQ ID NO 12
<211> LENGTH: 107
<212> TYPE: PRT
<213> ORGANISM: Artificial Sequence
<220> FEATURE:
<223> OTHER INFORMATION: VL sequence of CAR-SCA having SCA sequence
      based on antibody sequence against HIV.

<400> SEQUENCE: 12

Glu Leu Val Leu Thr Gln Ser Pro Gly Thr Leu Ser Leu Ser Ala Gly
1               5                   10                  15
Glu Arg Ala Thr Leu Ser Cys Arg Ala Ser Gln Ser Val Ser Ser Gly
            20                  25                  30
Ser Leu Ala Trp Tyr Gln Gln Lys Pro Gly Gln Ala Pro Arg Leu Leu
        35                  40                  45
Ile Tyr Gly Ala Ser Thr Arg Ala Thr Gly Ile Pro Asp Arg Phe Ser
    50                  55                  60
Gly Ser Gly Ser Gly Thr Asp Phe Thr Leu Thr Ile Gly Arg Leu Glu
65                  70                  75                  80
```

```
Pro Glu Asp Leu Ala Val Tyr Tyr Cys Gln Gln Tyr Gly Thr Ser Pro
                85                  90                  95

Tyr Thr Phe Gly Gln Gly Thr Lys Leu Glu Ile
            100                 105

<210> SEQ ID NO 13
<211> LENGTH: 687
<212> TYPE: PRT
<213> ORGANISM: Artificial Sequence
<220> FEATURE:
<223> OTHER INFORMATION: CAR-SCA having SCA sequence based on antibody
      sequence against HIV.

<400> SEQUENCE: 13

Met Leu Leu Leu Val Thr Ser Leu Leu Leu Cys Glu Leu Pro His Pro
1               5                   10                  15

Ala Phe Leu Leu Ile Pro Gln Pro Gln Leu Gln Glu Ser Gly Pro Gly
                20                  25                  30

Leu Val Glu Ala Ser Glu Thr Leu Ser Leu Thr Cys Thr Val Ser Gly
            35                  40                  45

Asp Ser Thr Ala Ala Cys Asp Tyr Phe Trp Gly Trp Val Arg Gln Pro
        50                  55                  60

Pro Gly Lys Gly Leu Glu Trp Ile Gly Gly Leu Ser His Cys Ala Gly
65                  70                  75                  80

Tyr Tyr Asn Thr Gly Trp Thr Tyr His Asn Pro Ser Leu Lys Ser Arg
                85                  90                  95

Leu Thr Ile Ser Leu Asp Thr Pro Lys Asn Gln Val Phe Leu Lys Leu
            100                 105                 110

Asn Ser Val Thr Ala Ala Asp Thr Ala Ile Tyr Tyr Cys Ala Arg Phe
        115                 120                 125

Asp Gly Glu Val Leu Val Tyr His Asp Trp Pro Lys Pro Ala Trp Val
    130                 135                 140

Asp Leu Trp Gly Arg Gly Thr Leu Val Thr Val Thr Val Ser Ser Gly
145                 150                 155                 160

Gly Gly Gly Ser Gly Gly Gly Gly Ser Gly Gly Gly Gly Ser Gln Ser
                165                 170                 175

Ala Leu Thr Gln Pro Pro Ser Ala Ser Gly Ser Pro Gly Gln Ser Ile
            180                 185                 190

Ser Ile Ser Cys Thr Gly Thr Ser Asn Arg Phe Val Ser Trp Tyr Gln
        195                 200                 205

Gln His Pro Gly Lys Ala Pro Lys Leu Val Ile Tyr Gly Val Asn Lys
    210                 215                 220

Arg Pro Ser Gly Val Pro Asp Arg Phe Ser Gly Ser Lys Ser Gly Asn
225                 230                 235                 240

Thr Ala Ser Leu Thr Val Ser Gly Leu Gln Thr Asp Asp Glu Ala Val
                245                 250                 255

Tyr Tyr Cys Ser Ser Leu Val Gly Asn Trp Asp Val Ile Phe Gly Gly
            260                 265                 270

Gly Thr Lys Leu Thr Val Leu Glu Ser Lys Tyr Gly Pro Pro Cys Pro
        275                 280                 285

Pro Cys Pro Ala Pro Glu Phe Leu Gly Gly Pro Ser Val Phe Leu Phe
    290                 295                 300

Pro Pro Lys Pro Lys Asp Thr Leu Met Ile Ser Arg Thr Pro Glu Val
305                 310                 315                 320

Thr Cys Val Val Val Asp Val Ser Gln Glu Asp Pro Glu Val Gln Phe
                325                 330                 335
```

-continued

```
Asn Trp Tyr Val Asp Gly Val Glu Val His Asn Ala Lys Thr Lys Pro
                340                 345                 350

Arg Glu Glu Gln Phe Asn Ser Thr Tyr Arg Val Val Ser Val Leu Thr
            355                 360                 365

Val Leu His Gln Asp Trp Leu Asn Gly Lys Glu Tyr Lys Cys Lys Val
        370                 375                 380

Ser Asn Lys Gly Leu Pro Ser Ser Ile Glu Lys Thr Ile Ser Lys Ala
385                 390                 395                 400

Lys Gly Gln Pro Arg Glu Pro Gln Val Tyr Thr Leu Pro Pro Ser Gln
                405                 410                 415

Glu Glu Met Thr Lys Asn Gln Val Ser Leu Thr Cys Leu Val Lys Gly
            420                 425                 430

Phe Tyr Pro Ser Asp Ile Ala Val Glu Trp Glu Ser Asn Gly Gln Pro
        435                 440                 445

Glu Asn Asn Tyr Lys Thr Thr Pro Pro Val Leu Asp Ser Asp Gly Ser
450                 455                 460

Phe Phe Leu Tyr Ser Arg Leu Thr Val Asp Lys Ser Arg Trp Gln Glu
465                 470                 475                 480

Gly Asn Val Phe Ser Cys Ser Val Met His Glu Ala Leu His Asn His
                485                 490                 495

Tyr Thr Gln Lys Ser Leu Ser Leu Ser Leu Gly Lys Asp Ile Tyr Ile
            500                 505                 510

Trp Ala Pro Leu Ala Gly Thr Cys Gly Val Leu Leu Leu Ser Leu Val
        515                 520                 525

Ile Thr Leu Tyr Cys Lys Arg Gly Arg Lys Lys Leu Leu Tyr Ile Phe
        530                 535                 540

Lys Gln Pro Phe Met Arg Pro Val Gln Thr Thr Gln Glu Glu Asp Gly
545                 550                 555                 560

Cys Ser Cys Arg Phe Pro Glu Glu Glu Gly Gly Cys Glu Leu Arg
                565                 570                 575

Val Lys Phe Ser Arg Ser Ala Asp Ala Pro Ala Tyr Lys Gln Gly Gln
            580                 585                 590

Asn Gln Leu Tyr Asn Glu Leu Asn Leu Gly Arg Arg Glu Glu Tyr Asp
        595                 600                 605

Val Leu Asp Lys Arg Arg Gly Arg Asp Pro Glu Met Gly Gly Lys Pro
        610                 615                 620

Arg Arg Lys Asn Pro Gln Glu Gly Leu Tyr Asn Glu Leu Gln Lys Asp
625                 630                 635                 640

Lys Met Ala Glu Ala Tyr Ser Glu Ile Gly Met Lys Gly Glu Arg Arg
                645                 650                 655

Arg Gly Lys Gly His Asp Gly Leu Tyr Gln Gly Leu Ser Thr Ala Thr
            660                 665                 670

Lys Asp Thr Tyr Asp Ala Leu His Met Gln Ala Leu Pro Pro Arg
        675                 680                 685

<210> SEQ ID NO 14
<211> LENGTH: 137
<212> TYPE: PRT
<213> ORGANISM: Artificial Sequence
<220> FEATURE:
<223> OTHER INFORMATION: VH sequence of CAR-SCA having SCA sequence
      based on antibody sequence against HIV.
```

<400> SEQUENCE: 14

Gln Pro Gln Leu Gln Glu Ser Gly Pro Gly Leu Val Glu Ala Ser Glu
1               5                   10                  15

Thr Leu Ser Leu Thr Cys Thr Val Ser Gly Asp Ser Thr Ala Ala Cys
            20                  25                  30

Asp Tyr Phe Trp Gly Trp Val Arg Gln Pro Pro Gly Lys Gly Leu Glu
        35                  40                  45

Trp Ile Gly Gly Leu Ser His Cys Ala Gly Tyr Tyr Asn Thr Gly Trp
    50                  55                  60

Thr Tyr His Asn Pro Ser Leu Lys Ser Arg Leu Thr Ile Ser Leu Asp
65                  70                  75                  80

Thr Pro Lys Asn Gln Val Phe Leu Lys Leu Asn Ser Val Thr Ala Ala
                85                  90                  95

Asp Thr Ala Ile Tyr Tyr Cys Ala Arg Phe Asp Gly Glu Val Leu Val
            100                 105                 110

Tyr His Asp Trp Pro Lys Pro Ala Trp Val Asp Leu Trp Gly Arg Gly
        115                 120                 125

Thr Leu Val Thr Val Thr Val Ser Ser
    130                 135

<210> SEQ ID NO 15
<211> LENGTH: 105
<212> TYPE: PRT
<213> ORGANISM: Artificial Sequence
<220> FEATURE:
<223> OTHER INFORMATION: VL sequence of CAR-SCA having SCA sequence
      based on antibody sequence against HIV.

<400> SEQUENCE: 15

Gln Ser Ala Leu Thr Gln Pro Pro Ser Ala Ser Gly Ser Pro Gly Gln
1               5                   10                  15

Ser Ile Ser Ile Ser Cys Thr Gly Thr Ser Asn Arg Phe Val Ser Trp
            20                  25                  30

Tyr Gln Gln His Pro Gly Lys Ala Pro Lys Leu Val Ile Tyr Gly Val
        35                  40                  45

Asn Lys Arg Pro Ser Gly Val Pro Asp Arg Phe Ser Gly Ser Lys Ser
    50                  55                  60

Gly Asn Thr Ala Ser Leu Thr Val Ser Gly Leu Gln Thr Asp Asp Glu
65                  70                  75                  80

Ala Val Tyr Tyr Cys Ser Ser Leu Val Gly Asn Trp Asp Val Ile Phe
                85                  90                  95

Gly Gly Gly Thr Lys Leu Thr Val Leu
            100                 105

<210> SEQ ID NO 16
<211> LENGTH: 685
<212> TYPE: PRT
<213> ORGANISM: Artificial Sequence
<220> FEATURE:
<223> OTHER INFORMATION: CAR-SCA having SCA sequence based on antibody
      sequence against HIV.

<400> SEQUENCE: 16

Met Leu Leu Leu Val Thr Ser Leu Leu Cys Glu Leu Pro His Pro
1               5                   10                  15

Ala Phe Leu Leu Ile Pro Gln Pro Gln Leu Gln Glu Ser Gly Pro Thr
            20                  25                  30

```
Leu Val Glu Ala Ser Glu Thr Leu Ser Leu Thr Cys Ala Val Ser Gly
             35                  40                  45

Asp Ser Thr Ala Ala Cys Asn Ser Phe Trp Gly Trp Val Arg Gln Pro
 50                  55                  60

Pro Gly Lys Gly Leu Glu Trp Val Gly Ser Leu Ser His Cys Ala Ser
 65                  70                  75                  80

Tyr Trp Asn Arg Gly Trp Thr Tyr His Asn Pro Ser Leu Lys Ser Arg
                 85                  90                  95

Leu Thr Leu Ala Leu Asp Thr Pro Lys Asn Leu Val Phe Leu Lys Leu
            100                 105                 110

Asn Ser Val Thr Ala Ala Asp Thr Ala Thr Tyr Tyr Cys Ala Arg Phe
            115                 120                 125

Gly Gly Glu Val Leu Arg Tyr Thr Asp Trp Pro Lys Pro Ala Trp Val
130                 135                 140

Asp Leu Trp Gly Arg Gly Thr Leu Val Thr Val Ser Ser Gly Gly Gly
145                 150                 155                 160

Gly Ser Gly Gly Gly Gly Ser Gly Gly Gly Gly Ser Gln Ser Ala Leu
                165                 170                 175

Thr Gln Pro Pro Ser Ala Ser Gly Ser Pro Gly Gln Ser Ile Thr Ile
            180                 185                 190

Ser Cys Thr Gly Thr Ser Asn Asn Phe Val Ser Trp Tyr Gln Gln His
            195                 200                 205

Ala Gly Lys Ala Pro Lys Leu Val Ile Tyr Asp Val Asn Lys Arg Pro
210                 215                 220

Ser Gly Val Pro Asp Arg Phe Ser Gly Ser Lys Ser Gly Asn Thr Ala
225                 230                 235                 240

Ser Leu Thr Val Ser Gly Leu Gln Thr Asp Asp Glu Ala Val Tyr Tyr
                245                 250                 255

Cys Gly Ser Leu Val Gly Asn Trp Asp Val Ile Phe Gly Gly Gly Thr
            260                 265                 270

Lys Leu Thr Val Leu Glu Ser Lys Tyr Gly Pro Pro Cys Pro Pro Cys
            275                 280                 285

Pro Ala Pro Glu Phe Leu Gly Gly Pro Ser Val Phe Leu Phe Pro Pro
290                 295                 300

Lys Pro Lys Asp Thr Leu Met Ile Ser Arg Thr Pro Glu Val Thr Cys
305                 310                 315                 320

Val Val Val Asp Val Ser Gln Glu Asp Pro Glu Val Gln Phe Asn Trp
                325                 330                 335

Tyr Val Asp Gly Val Glu Val His Asn Ala Lys Thr Lys Pro Arg Glu
            340                 345                 350

Glu Gln Phe Asn Ser Thr Tyr Arg Val Val Ser Val Leu Thr Val Leu
            355                 360                 365

His Gln Asp Trp Leu Asn Gly Lys Glu Tyr Lys Cys Lys Val Ser Asn
370                 375                 380

Lys Gly Leu Pro Ser Ser Ile Glu Lys Thr Ile Ser Lys Ala Lys Gly
385                 390                 395                 400

Gln Pro Arg Glu Pro Gln Val Tyr Thr Leu Pro Pro Ser Gln Glu Glu
                405                 410                 415

Met Thr Lys Asn Gln Val Ser Leu Thr Cys Leu Val Lys Gly Phe Tyr
            420                 425                 430

Pro Ser Asp Ile Ala Val Glu Trp Glu Ser Asn Gly Gln Pro Glu Asn
            435                 440                 445
```

```
Asn Tyr Lys Thr Thr Pro Pro Val Leu Asp Ser Asp Gly Ser Phe Phe
    450                 455                 460

Leu Tyr Ser Arg Leu Thr Val Asp Lys Ser Arg Trp Gln Glu Gly Asn
465                 470                 475                 480

Val Phe Ser Cys Ser Val Met His Glu Ala Leu His Asn His Tyr Thr
                485                 490                 495

Gln Lys Ser Leu Ser Leu Ser Leu Gly Lys Asp Ile Tyr Ile Trp Ala
            500                 505                 510

Pro Leu Ala Gly Thr Cys Gly Val Leu Leu Ser Leu Val Ile Thr
            515                 520                 525

Leu Tyr Cys Lys Arg Gly Arg Lys Lys Leu Leu Tyr Ile Phe Lys Gln
        530                 535                 540

Pro Phe Met Arg Pro Val Gln Thr Thr Gln Glu Glu Asp Gly Cys Ser
545                 550                 555                 560

Cys Arg Phe Pro Glu Glu Glu Gly Gly Cys Glu Leu Arg Val Lys
                565                 570                 575

Phe Ser Arg Ser Ala Asp Ala Pro Ala Tyr Lys Gln Gly Gln Asn Gln
            580                 585                 590

Leu Tyr Asn Glu Leu Asn Leu Gly Arg Arg Glu Tyr Asp Val Leu
        595                 600                 605

Asp Lys Arg Arg Gly Arg Asp Pro Glu Met Gly Gly Lys Pro Arg Arg
610                 615                 620

Lys Asn Pro Gln Glu Gly Leu Tyr Asn Glu Leu Gln Lys Asp Lys Met
625                 630                 635                 640

Ala Glu Ala Tyr Ser Glu Ile Gly Met Lys Gly Glu Arg Arg Arg Gly
                645                 650                 655

Lys Gly His Asp Gly Leu Tyr Gln Gly Leu Ser Thr Ala Thr Lys Asp
            660                 665                 670

Thr Tyr Asp Ala Leu His Met Gln Ala Leu Pro Pro Arg
            675                 680                 685

<210> SEQ ID NO 17
<211> LENGTH: 135
<212> TYPE: PRT
<213> ORGANISM: Artificial Sequence
<220> FEATURE:
<223> OTHER INFORMATION: VH sequence of CAR-SCA having SCA sequence
      based on antibody sequence against HIV.

<400> SEQUENCE: 17

Gln Pro Gln Leu Gln Glu Ser Gly Pro Thr Leu Val Glu Ala Ser Glu
1               5                   10                  15

Thr Leu Ser Leu Thr Cys Ala Val Ser Gly Asp Ser Thr Ala Ala Cys
            20                  25                  30

Asn Ser Phe Trp Gly Trp Val Arg Gln Pro Pro Gly Lys Gly Leu Glu
        35                  40                  45

Trp Val Gly Ser Leu Ser His Cys Ala Ser Tyr Trp Asn Arg Gly Trp
    50                  55                  60

Thr Tyr His Asn Pro Ser Leu Lys Ser Arg Leu Thr Leu Ala Leu Asp
65                  70                  75                  80

Thr Pro Lys Asn Leu Val Phe Leu Lys Leu Asn Ser Val Thr Ala Ala
                85                  90                  95

Asp Thr Ala Thr Tyr Tyr Cys Ala Arg Phe Gly Gly Glu Val Leu Arg
            100                 105                 110
```

```
Tyr Thr Asp Trp Pro Lys Pro Ala Trp Val Asp Leu Trp Gly Arg Gly
            115                 120                 125

Thr Leu Val Thr Val Ser Ser
            130                 135

<210> SEQ ID NO 18
<211> LENGTH: 105
<212> TYPE: PRT
<213> ORGANISM: Artificial Sequence
<220> FEATURE:
<223> OTHER INFORMATION: VL sequence of CAR-SCA having SCA sequence
      based on antibody sequence against HIV.

<400> SEQUENCE: 18

Gln Ser Ala Leu Thr Gln Pro Pro Ser Ala Ser Gly Ser Pro Gly Gln
1               5                   10                  15

Ser Ile Thr Ile Ser Cys Thr Gly Thr Ser Asn Asn Phe Val Ser Trp
            20                  25                  30

Tyr Gln Gln His Ala Gly Lys Ala Pro Lys Leu Val Ile Tyr Asp Val
        35                  40                  45

Asn Lys Arg Pro Ser Gly Val Pro Asp Arg Phe Ser Gly Ser Lys Ser
    50                  55                  60

Gly Asn Thr Ala Ser Leu Thr Val Ser Gly Leu Gln Thr Asp Asp Glu
65                  70                  75                  80

Ala Val Tyr Tyr Cys Gly Ser Leu Val Gly Asn Trp Asp Val Ile Phe
                85                  90                  95

Gly Gly Gly Thr Lys Leu Thr Val Leu
            100                 105

<210> SEQ ID NO 19
<211> LENGTH: 691
<212> TYPE: PRT
<213> ORGANISM: Artificial Sequence
<220> FEATURE:
<223> OTHER INFORMATION: CAR-SCA having SCA sequence based on antibody
      sequence against HIV.

<400> SEQUENCE: 19

Met Leu Leu Leu Val Thr Ser Leu Leu Cys Glu Leu Pro His Pro
1               5                   10                  15

Ala Phe Leu Leu Ile Pro Gln Arg Leu Val Glu Ser Gly Gly Gly Val
            20                  25                  30

Val Gln Pro Gly Ser Ser Leu Arg Leu Ser Cys Ala Ala Ser Gly Phe
        35                  40                  45

Asp Phe Ser Arg Gln Gly Met His Trp Val Arg Gln Ala Pro Gly Gln
    50                  55                  60

Gly Leu Glu Trp Val Ala Phe Ile Lys Tyr Asp Gly Ser Glu Lys Tyr
65                  70                  75                  80

His Ala Asp Ser Val Trp Gly Arg Leu Ser Ile Ser Arg Asp Asn Ser
                85                  90                  95

Lys Asp Thr Leu Tyr Leu Gln Met Asn Ser Leu Arg Val Glu Asp Thr
            100                 105                 110

Ala Thr Tyr Phe Cys Val Arg Glu Ala Gly Pro Asp Tyr Arg Asn
        115                 120                 125

Gly Tyr Asn Tyr Tyr Asp Phe Tyr Asp Gly Tyr Tyr Asn Tyr His Tyr
    130                 135                 140

Met Asp Val Trp Gly Lys Gly Thr Thr Val Thr Val Ser Ser Gly Gly
145                 150                 155                 160
```

```
Gly Gly Ser Gly Gly Gly Gly Ser Gly Gly Gly Ser Gln Ser Ala
            165                 170                 175

Leu Thr Gln Pro Ala Ser Val Ser Gly Ser Pro Gly Gln Ser Ile Thr
            180                 185                 190

Ile Ser Cys Asn Gly Thr Ser Asn Asp Val Gly Gly Tyr Glu Ser Val
            195                 200                 205

Ser Trp Tyr Gln Gln His Pro Gly Lys Ala Pro Lys Val Val Ile Tyr
            210                 215                 220

Asp Val Ser Lys Arg Pro Ser Gly Val Ser Asn Arg Phe Ser Gly Ser
225                 230                 235                 240

Lys Ser Gly Asn Thr Ala Ser Leu Thr Ile Ser Gly Leu Gln Ala Glu
            245                 250                 255

Asp Glu Gly Asp Tyr Tyr Cys Lys Ser Leu Thr Ser Thr Arg Arg Arg
            260                 265                 270

Val Phe Gly Thr Gly Thr Lys Leu Thr Val Leu Glu Ser Lys Tyr Gly
            275                 280                 285

Pro Pro Cys Pro Pro Cys Pro Ala Pro Glu Phe Leu Gly Gly Pro Ser
            290                 295                 300

Val Phe Leu Phe Pro Pro Lys Pro Lys Asp Thr Leu Met Ile Ser Arg
305                 310                 315                 320

Thr Pro Glu Val Thr Cys Val Val Val Asp Val Ser Gln Glu Asp Pro
            325                 330                 335

Glu Val Gln Phe Asn Trp Tyr Val Asp Gly Val Glu Val His Asn Ala
            340                 345                 350

Lys Thr Lys Pro Arg Glu Glu Gln Phe Asn Ser Thr Tyr Arg Val Val
            355                 360                 365

Ser Val Leu Thr Val Leu His Gln Asp Trp Leu Asn Gly Lys Glu Tyr
            370                 375                 380

Lys Cys Lys Val Ser Asn Lys Gly Leu Pro Ser Ser Ile Glu Lys Thr
385                 390                 395                 400

Ile Ser Lys Ala Lys Gly Gln Pro Arg Glu Pro Gln Val Tyr Thr Leu
            405                 410                 415

Pro Pro Ser Gln Glu Glu Met Thr Lys Asn Gln Val Ser Leu Thr Cys
            420                 425                 430

Leu Val Lys Gly Phe Tyr Pro Ser Asp Ile Ala Val Glu Trp Glu Ser
            435                 440                 445

Asn Gly Gln Pro Glu Asn Asn Tyr Lys Thr Thr Pro Pro Val Leu Asp
450                 455                 460

Ser Asp Gly Ser Phe Phe Leu Tyr Ser Arg Leu Thr Val Asp Lys Ser
465                 470                 475                 480

Arg Trp Gln Glu Gly Asn Val Phe Ser Cys Ser Val Met His Glu Ala
            485                 490                 495

Leu His Asn His Tyr Thr Gln Lys Ser Leu Ser Leu Ser Leu Gly Lys
            500                 505                 510

Asp Ile Tyr Ile Trp Ala Pro Leu Ala Gly Thr Cys Gly Val Leu Leu
            515                 520                 525

Leu Ser Leu Val Ile Thr Leu Tyr Cys Lys Arg Gly Arg Lys Lys Leu
            530                 535                 540

Leu Tyr Ile Phe Lys Gln Pro Phe Met Arg Pro Val Gln Thr Thr Gln
545                 550                 555                 560

Glu Glu Asp Gly Cys Ser Cys Arg Phe Pro Glu Glu Glu Glu Gly Gly
            565                 570                 575
```

```
Cys Glu Leu Arg Val Lys Phe Ser Arg Ser Ala Asp Ala Pro Ala Tyr
            580                 585                 590

Lys Gln Gly Gln Asn Gln Leu Tyr Asn Glu Leu Asn Leu Gly Arg Arg
        595                 600                 605

Glu Glu Tyr Asp Val Leu Asp Lys Arg Gly Arg Asp Pro Glu Met
    610                 615                 620

Gly Gly Lys Pro Arg Arg Lys Asn Pro Gln Glu Gly Leu Tyr Asn Glu
625                 630                 635                 640

Leu Gln Lys Asp Lys Met Ala Glu Ala Tyr Ser Glu Ile Gly Met Lys
                645                 650                 655

Gly Glu Arg Arg Arg Gly Lys Gly His Asp Gly Leu Tyr Gln Gly Leu
                660                 665                 670

Ser Thr Ala Thr Lys Asp Thr Tyr Asp Ala Leu His Met Gln Ala Leu
                675                 680                 685

Pro Pro Arg
    690

<210> SEQ ID NO 20
<211> LENGTH: 136
<212> TYPE: PRT
<213> ORGANISM: Artificial Sequence
<220> FEATURE:
<223> OTHER INFORMATION: VH sequence of CAR-SCA having SCA sequence
      based on antibody sequence against HIV.

<400> SEQUENCE: 20

Gln Arg Leu Val Glu Ser Gly Gly Gly Val Val Gln Pro Gly Ser Ser
1               5                   10                  15

Leu Arg Leu Ser Cys Ala Ala Ser Gly Phe Asp Phe Ser Arg Gln Gly
                20                  25                  30

Met His Trp Val Arg Gln Ala Pro Gly Gln Gly Leu Glu Trp Val Ala
            35                  40                  45

Phe Ile Lys Tyr Asp Gly Ser Glu Lys Tyr His Ala Asp Ser Val Trp
    50                  55                  60

Gly Arg Leu Ser Ile Ser Arg Asp Asn Ser Lys Asp Thr Leu Tyr Leu
65                  70                  75                  80

Gln Met Asn Ser Leu Arg Val Glu Asp Thr Ala Thr Tyr Phe Cys Val
                85                  90                  95

Arg Glu Ala Gly Gly Pro Asp Tyr Arg Asn Gly Tyr Asn Tyr Tyr Asp
                100                 105                 110

Phe Tyr Asp Gly Tyr Tyr Asn Tyr His Tyr Met Asp Val Trp Gly Lys
            115                 120                 125

Gly Thr Thr Val Thr Val Ser Ser
    130                 135

<210> SEQ ID NO 21
<211> LENGTH: 110
<212> TYPE: PRT
<213> ORGANISM: Artificial Sequence
<220> FEATURE:
<223> OTHER INFORMATION: VL sequence of CAR-SCA having SCA sequence
      based on antibody sequence against HIV.

<400> SEQUENCE: 21

Gln Ser Ala Leu Thr Gln Pro Ala Ser Val Ser Gly Ser Pro Gly Gln
1               5                   10                  15

Ser Ile Thr Ile Ser Cys Asn Gly Thr Ser Asn Asp Val Gly Gly Tyr
                20                  25                  30
```

```
Glu Ser Val Ser Trp Tyr Gln Gln His Pro Gly Lys Ala Pro Lys Val
                35                  40                  45

Val Ile Tyr Asp Val Ser Lys Arg Pro Ser Gly Val Ser Asn Arg Phe
 50                  55                  60

Ser Gly Ser Lys Ser Gly Asn Thr Ala Ser Leu Thr Ile Ser Gly Leu
 65                  70                  75                  80

Gln Ala Glu Asp Glu Gly Asp Tyr Tyr Cys Lys Ser Leu Thr Ser Thr
                85                  90                  95

Arg Arg Arg Val Phe Gly Thr Gly Thr Lys Leu Thr Val Leu
                100                 105                 110

<210> SEQ ID NO 22
<211> LENGTH: 685
<212> TYPE: PRT
<213> ORGANISM: Artificial Sequence
<220> FEATURE:
<223> OTHER INFORMATION: CAR-SCA having SCA sequence based on antibody
      sequence against HIV.

<400> SEQUENCE: 22

Met Leu Leu Leu Val Thr Ser Leu Leu Leu Cys Glu Leu Pro His Pro
 1               5                  10                  15

Ala Phe Leu Leu Ile Pro Glu Val Gln Leu Val Glu Ser Gly Gly Gly
                20                  25                  30

Leu Val Lys Pro Gly Gly Ser Leu Arg Leu Ser Cys Ser Ala Ser Gly
                35                  40                  45

Phe Asp Phe Asp Asn Ala Trp Met Thr Trp Val Arg Gln Pro Pro Gly
 50                  55                  60

Lys Gly Leu Glu Trp Val Gly Arg Ile Thr Gly Pro Gly Glu Gly Trp
 65                  70                  75                  80

Ser Val Asp Tyr Ala Ala Pro Val Glu Gly Arg Phe Thr Ile Ser Arg
                85                  90                  95

Leu Asn Ser Ile Asn Phe Leu Tyr Leu Glu Met Asn Asn Leu Arg Met
                100                 105                 110

Glu Asp Ser Gly Leu Tyr Phe Cys Ala Arg Thr Gly Lys Tyr Tyr Asp
                115                 120                 125

Phe Trp Ser Gly Tyr Pro Pro Gly Glu Glu Tyr Phe Gln Asp Trp Gly
                130                 135                 140

Arg Gly Thr Leu Val Thr Val Ser Ser Gly Gly Gly Gly Ser Gly Gly
145                 150                 155                 160

Gly Gly Ser Gly Gly Gly Gly Ser Ser Tyr Glu Leu Thr Gln Glu Thr
                165                 170                 175

Gly Val Ser Val Ala Leu Gly Arg Thr Val Thr Ile Thr Cys Arg Gly
                180                 185                 190

Asp Ser Leu Arg Ser His Tyr Ala Ser Trp Tyr Gln Lys Lys Pro Gly
                195                 200                 205

Gln Ala Pro Ile Leu Leu Phe Tyr Gly Lys Asn Asn Arg Pro Ser Gly
                210                 215                 220

Val Pro Asp Arg Phe Ser Gly Ser Ala Ser Gly Asn Arg Ala Ser Leu
225                 230                 235                 240

Thr Ile Ser Gly Ala Gln Ala Glu Asp Asp Ala Glu Tyr Tyr Cys Ser
                245                 250                 255

Ser Arg Asp Lys Ser Gly Ser Arg Leu Ser Val Phe Gly Gly Gly Thr
                260                 265                 270
```

```
Lys Leu Thr Val Leu Glu Ser Lys Tyr Gly Pro Pro Cys Pro Pro Cys
            275                 280                 285
Pro Ala Pro Glu Phe Leu Gly Gly Pro Ser Val Phe Leu Phe Pro Pro
        290                 295                 300
Lys Pro Lys Asp Thr Leu Met Ile Ser Arg Thr Pro Glu Val Thr Cys
305                 310                 315                 320
Val Val Val Asp Val Ser Gln Glu Asp Pro Glu Val Gln Phe Asn Trp
                325                 330                 335
Tyr Val Asp Gly Val Glu Val His Asn Ala Lys Thr Lys Pro Arg Glu
            340                 345                 350
Glu Gln Phe Asn Ser Thr Tyr Arg Val Val Ser Val Leu Thr Val Leu
        355                 360                 365
His Gln Asp Trp Leu Asn Gly Lys Glu Tyr Lys Cys Lys Val Ser Asn
    370                 375                 380
Lys Gly Leu Pro Ser Ser Ile Glu Lys Thr Ile Ser Lys Ala Lys Gly
385                 390                 395                 400
Gln Pro Arg Glu Pro Gln Val Tyr Thr Leu Pro Pro Ser Gln Glu Glu
                405                 410                 415
Met Thr Lys Asn Gln Val Ser Leu Thr Cys Leu Val Lys Gly Phe Tyr
            420                 425                 430
Pro Ser Asp Ile Ala Val Glu Trp Glu Ser Asn Gly Gln Pro Glu Asn
        435                 440                 445
Asn Tyr Lys Thr Thr Pro Pro Val Leu Asp Ser Asp Gly Ser Phe Phe
    450                 455                 460
Leu Tyr Ser Arg Leu Thr Val Asp Lys Ser Arg Trp Gln Glu Gly Asn
465                 470                 475                 480
Val Phe Ser Cys Ser Val Met His Glu Ala Leu His Asn His Tyr Thr
                485                 490                 495
Gln Lys Ser Leu Ser Leu Ser Leu Gly Lys Asp Ile Tyr Ile Trp Ala
            500                 505                 510
Pro Leu Ala Gly Thr Cys Gly Val Leu Leu Leu Ser Leu Val Ile Thr
        515                 520                 525
Leu Tyr Cys Lys Arg Gly Arg Lys Lys Leu Leu Tyr Ile Phe Lys Gln
    530                 535                 540
Pro Phe Met Arg Pro Val Gln Thr Thr Gln Glu Glu Asp Gly Cys Ser
545                 550                 555                 560
Cys Arg Phe Pro Glu Glu Glu Glu Gly Gly Cys Glu Leu Arg Val Lys
                565                 570                 575
Phe Ser Arg Ser Ala Asp Ala Pro Ala Tyr Lys Gln Gly Gln Asn Gln
            580                 585                 590
Leu Tyr Asn Glu Leu Asn Leu Gly Arg Arg Glu Glu Tyr Asp Val Leu
        595                 600                 605
Asp Lys Arg Arg Gly Arg Asp Pro Glu Met Gly Gly Lys Pro Arg Arg
    610                 615                 620
Lys Asn Pro Gln Glu Gly Leu Tyr Asn Glu Leu Gln Lys Asp Lys Met
625                 630                 635                 640
Ala Glu Ala Tyr Ser Glu Ile Gly Met Lys Gly Glu Arg Arg Arg Gly
                645                 650                 655
Lys Gly His Asp Gly Leu Tyr Gln Gly Leu Ser Thr Ala Thr Lys Asp
            660                 665                 670
Thr Tyr Asp Ala Leu His Met Gln Ala Leu Pro Pro Arg
        675                 680                 685
```

<210> SEQ ID NO 23
<211> LENGTH: 131
<212> TYPE: PRT
<213> ORGANISM: Artificial Sequence
<220> FEATURE:
<223> OTHER INFORMATION: VH sequence of CAR-SCA having SCA sequence based on antibody sequence against HIV.

<400> SEQUENCE: 23

```
Glu Val Gln Leu Val Glu Ser Gly Gly Gly Leu Val Lys Pro Gly Gly
1               5                   10                  15

Ser Leu Arg Leu Ser Cys Ser Ala Ser Gly Phe Asp Phe Asp Asn Ala
            20                  25                  30

Trp Met Thr Trp Val Arg Gln Pro Pro Gly Lys Gly Leu Glu Trp Val
        35                  40                  45

Gly Arg Ile Thr Gly Pro Gly Glu Gly Trp Ser Val Asp Tyr Ala Ala
    50                  55                  60

Pro Val Glu Gly Arg Phe Thr Ile Ser Arg Leu Asn Ser Ile Asn Phe
65                  70                  75                  80

Leu Tyr Leu Glu Met Asn Asn Leu Arg Met Glu Asp Ser Gly Leu Tyr
                85                  90                  95

Phe Cys Ala Arg Thr Gly Lys Tyr Tyr Asp Phe Trp Ser Gly Tyr Pro
            100                 105                 110

Pro Gly Glu Glu Tyr Phe Gln Asp Trp Gly Arg Gly Thr Leu Val Thr
        115                 120                 125

Val Ser Ser
        130
```

<210> SEQ ID NO 24
<211> LENGTH: 109
<212> TYPE: PRT
<213> ORGANISM: Artificial Sequence
<220> FEATURE:
<223> OTHER INFORMATION: VL sequence of CAR-SCA having SCA sequence based on antibody sequence against HIV.

<400> SEQUENCE: 24

```
Ser Tyr Glu Leu Thr Gln Glu Thr Gly Val Ser Val Ala Leu Gly Arg
1               5                   10                  15

Thr Val Thr Ile Thr Cys Arg Gly Asp Ser Leu Arg Ser His Tyr Ala
            20                  25                  30

Ser Trp Tyr Gln Lys Lys Pro Gly Gln Ala Pro Ile Leu Leu Phe Tyr
        35                  40                  45

Gly Lys Asn Asn Arg Pro Ser Gly Val Pro Asp Arg Phe Ser Gly Ser
    50                  55                  60

Ala Ser Gly Asn Arg Ala Ser Leu Thr Ile Ser Gly Ala Gln Ala Glu
65                  70                  75                  80

Asp Asp Ala Glu Tyr Tyr Cys Ser Ser Arg Asp Lys Ser Gly Ser Arg
                85                  90                  95

Leu Ser Val Phe Gly Gly Gly Thr Lys Leu Thr Val Leu
            100                 105
```

<210> SEQ ID NO 25
<211> LENGTH: 2013
<212> TYPE: DNA
<213> ORGANISM: Artificial Sequence
<220> FEATURE:
<223> OTHER INFORMATION: Nucleic acid sequence encoding CAR-SCA having SCA sequence based on antibody sequence against HIV.

<400> SEQUENCE: 25

```
atgctgctgc tggtgacaag cctgctgctg tgcgagctgc ccacccgc ctttctgctg      60
atcccccagg tgcagctggt gcagtctggc gggcagatga agaaacccgg cgagagcatg     120
cggatcagct gccgggcctc cggctacgag ttcatcgact gcaccctgaa ctggatccgg     180
ctggccctg gcaagaggcc cgagtggatg ggctggctga gcccagagg cggagccgtg      240
aactacgcca ccccctcca gggcagagtg accatgaccc gggacgtgta cagcgatacc     300
gccttcctgg aactgcggag cctgaccgtg gacgataccg ccgtgtactt ctgcacccgg     360
ggcaagaact gcgactacaa ctgggacttc agcactggg gcagaggcac cccgtgatc     420
gtgtctagcg gaggcggagg atctggaggc ggaggctctg ggggaggcgg aagcgagatc     480
gtgctgaccc agagccctgg caccctgagc ctgtctcccg gcgaaacgc catcatcagc     540
tgcagaacca gccagtacgg cagcctcgcc tggtatcagc agaggccagg ccaggccccc     600
agactggtga tctacagcgg cagcaccaga gccgccggaa tccccgacag attcagcggc     660
tccagatggg gacctgacta caacctgacc atcagcaacc tggaaagcgg cgacttcggc     720
gtgtactact gccagcagta cgagttcttc ggccagggca ccaaggtgca ggtggacatc     780
aagcgggaga gcaaatacgg cccccctgc cccccttgcc ctgccccga gttcctgggc     840
ggacccagcg tgttcctgtt cccccccaag cccaaggaca ccctgatgat cagccggacc     900
cccgaggtga cctgtgtggt ggtggacgtg tcccaggagg accccgaggt ccagttcaac     960
tggtacgtgg acggcgtgga ggtgcacaac gccaagacca gccccgggga ggagcagttc    1020
aatagcaccct accgggtggt gtccgtgctg accgtgctgc accaggactg gctgaacggc    1080
aaggaataca gtgtaaggt gtccaacaag ggcctgccca gcagcatcga gaaaaccatc    1140
agcaaggcca agggccagcc tcgggagccc caggtgtaca ccctgccccc tagccaagag    1200
gagatgacca agaaccaggt gtccctgacc tgcctggtga agggcttcta ccccagcgac    1260
atcgccgtgg agtgggagag caacggccag cccgagaaca actacaagac cacccccct    1320
gtgctggaca gcgacggcag cttcttcctg tacagccggc tgaccgtgga caagagccgg    1380
tggcaggagg gcaacgtctt tagctgctcc gtgatgcacg aggccctgca caaccactac    1440
acccagaaga gcctgagcct gtccctgggc aaggatatct acatctgggc gcccttggcc    1500
gggacttgtg gggtccttct cctgtcactg gttatcaccc tttactgcaa cggggcagaa    1560
aagaaactcc tgtatatatt caaacaacca tttatgagac cagtacaaac tactcaagag    1620
gaagatggct gtagctgccg atttccagaa gaagaagaag gaggatgtga actgagagtg    1680
aagttcagca ggagcgcaga cgcccccgcg tacaagcagg gccagaacca gctctataac    1740
gagctcaatc taggacgaag agaggagtac gatgttttgg acaagagacg tggccgggac    1800
cctgagatgg ggggaaagcc gagaaggaag aaccctcagg aaggcctgta caatgaactg    1860
cagaaagata gatggcgga ggcctacagt gagattggga tgaaaggcga gcgccggagg    1920
ggcaagggc acgatggcct ttaccagggt ctcagtacag ccaccaagga cacctacgac    1980
gcccttcaca tgcaggccct gccccctcgc taa                                 2013
```

<210> SEQ ID NO 26
<211> LENGTH: 2040
<212> TYPE: DNA
<213> ORGANISM: Artificial Sequence
<220> FEATURE:
<223> OTHER INFORMATION: Nucleic acid sequence encoding CAR-SCA having SCA sequence based on antibody sequence against HIV.

<400> SEQUENCE: 26

```
atgctgctgc tggtgacaag cctgctgctg tgcgagctgc ccacccctgc ctttctgctg      60
atcccccagg tgcagctgct gcagagcgga gccgccgtga caaagcctgg cgcttctgtg     120
cgggtgtcct gcgaggccag cggctacaac atccgggact acttcatcca ctggtggcgg     180
caggccccag ccagggact gcagtgggtg ggatggatca accccaagac cggccagccc     240
aacaaccccc ggcagttcca gggccgggtg tccctgacaa acacgccag ctgggacttc     300
gacaccttca gcttctacat ggacctgaag gccctgcgga gcgacgatac cgccgtgtac     360
ttctgcgcca gacagcggag cgactactgg gatttcgacg tgtggggcag cggcacccag     420
gtcacagtgt ccagcgccag cacaaaggga cctggcggcg aggatctggc ggaggcgga     480
agtggcggag gggcagcga tattcagatg acccagagcc ccagcagcct gagcgccagc     540
gtgggcgaca ccgtgaccat cacctgtcag gccaacggat acctgaactg gtatcagcag     600
cggagaggca aggcccccaa gctgctgatc tacgacggca gcaagctgga acggggcgtg     660
cccagccggt tcagcggcag aagatggggc caagagtaca acctgaccat caacaacctg     720
cagcccgagg atattgccac atacttttgc caggtgtacg agttcgtggt gcccgggacc     780
cggctggatc tgaagagaac cgtggccgct cccgagagca aatacgggcc ccctgcccc     840
ccttgccctg ccccgagtt cctgggcgga cccagcgtgt tcctgttccc cccaagccc     900
aaggacaccc tgatgatcag ccggaccccc gaggtgacct gtgtggtggt ggacgtgtcc     960
caggaggacc ccgaggtcca gttcaactgg tacgtggacg gcgtggaggt gcacaacgcc    1020
aagaccaagc ccgggagga gcagttcaat agcacctacc gggtggtgtc cgtgctgacc    1080
gtgctgcacc aggactggct gaacggcaag gaatacaagt gtaaggtgtc caacaagggc    1140
ctgcccagca gcatcgagaa aaccatcagc aaggccaagg gccagcctcg ggagccccag    1200
gtgtacaccc tgcccccctag ccaagaggag atgaccaaga accaggtgtc cctgacctgc    1260
ctggtgaagg gcttctaccc cagcgacatc gccgtggagt gggagagcaa cggccagccc    1320
gagaacaact acaagaccac cccccctgtg ctggacagcg acggcagctt cttcctgtac    1380
agccggctga ccgtggacaa gagccggtgg caggagggca acgtctttag ctgctccgtg    1440
atgcacgagg ccctgcacaa ccactacacc cagaagagcc tgagcctgtc cctgggcaag    1500
gatatctaca tctgggcgcc cttggccggg acttgtgggg tccttctcct gtcactggtt    1560
atccccttt actgcaaacg gggcagaaag aaactcctgt atatattcaa acaaccattt    1620
atgagaccag tacaaactac tcaagaggaa gatggctgta gctgccgatt ccagaagaa    1680
gaagaaggag gatgtgaact gagagtgaag ttcagcagga gcgcagacgc ccccgcgtac    1740
aagcagggcc agaaccagct ctataacgag ctcaatctag gacgaagaga ggagtacgat    1800
gttttggaca gagacgtgg ccgggaccct gagatggggg gaaagccgag aaggaagaac    1860
cctcaggaag gcctgtacaa tgaactgcag aaagataaga tggcggaggc ctacagtgag    1920
attgggatga aggcgagcg ccggaggggc aaggggcacg atggcctta ccagggtctc    1980
agtacagcca ccaaggacac ctacgacgcc cttcacatgc aggccctgcc ccctcgctaa    2040
```

<210> SEQ ID NO 27
<211> LENGTH: 2043
<212> TYPE: DNA
<213> ORGANISM: Artificial Sequence
<220> FEATURE:
<223> OTHER INFORMATION: Nucleic acid sequence encoding CAR-SCA having SCA sequence based on antibody sequence against HIV.

<400> SEQUENCE: 27

```
atgctgctgc tcgtgacaag cctgctgctg tgcgagctgc ccacccgc ctttctgctg      60
atccccctgg aacagtctgg cgccgaagtg aagaaacccg gcagcagcgt gcaggtgtcc     120
tgcaaggcca gcggcggcac cttctctatg tacggcttca actgggtccg ccaggctcct    180
ggacacggcc tggaatggat gggcggcatc atccccatct tcggcacctc caactacgcc    240
cagaaattcc ggggcagagt gaccttcacc gccgaccagg ccaccagcac cgcctacatg    300
gaactgacca acctgcggag cgacgacacc gccgtgtact actgcgccag agacttcggc    360
cccgactggg aggacggcga cagctacgat ggcagcggca gaggcttctt cgacttctgg    420
ggccagggca ccctggtgac agtgtctagc ggaggcggag gctctggagg cggaggaagt    480
ggcggagggg gatctgagct ggtgctgacc cagagccctg gcaccctgtc tctgtctgcc    540
ggcgagagag ccaccctgag ctgcagagcc agccagagcg tctccagcgg cagcctggcc    600
tggtatcagc agaagcccgg ccaggcccc agactgctga tctacggcgc cagcaccaga    660
gccaccggca tccccgatag attcagcgga agcggctccg gcaccgactt caccctgacc    720
atcggccggc tggaacccga ggacctggcc gtgtattact gtcagcagta cggcaccagc    780
ccctacacct tcggccaggg gaccaagctg gaaatcgaga gcaaatacgg ccccccctgc    840
ccccttgcc ctgcccccga gttcctgggc ggacccagcg tgttcctgtt ccccccaag    900
cccaaggaca ccctgatgat cagccggacc cccgaggtga cctgtgtggt ggtggacgtg    960
tcccaggagg accccgaggt ccagttcaac tggtacgtgg acggcgtgga ggtgcacaac   1020
gccaagacca gccccgggga ggagcagttc aatagcacct accgggtggt gtccgtgctg   1080
accgtgctgc accaggactg gctgaacggc aaggaataca agtgtaaggt gtccaacaag   1140
ggcctgccca gcagcatcga aaaaccatc agcaaggcca agggccagcc tcgggagccc   1200
caggtgtaca ccctgccccc tagccaagag gagatgacca gaaccaggt gtccctgacc   1260
tgcctggtga agggcttcta ccccagcgac atcgccgtgg agtgggagag caacggccag   1320
cccgagaaca actacaagac cacccccct gtgctggaca cgacggcag cttcttcctg   1380
tacagccggc tgaccgtgga caagagccgg tggcaggagg gcaacgtctt tagctgctcc   1440
gtgatgcacg aggccctgca caaccactac acccagaaga gcctgagcct gtccctgggc   1500
aaggatatct acatctgggc gcccttggcc gggacttgtg gggtccttct cctgtcactg   1560
gttatcaccc tttactgcaa acggggcaga aagaaactcc tgtatatatt caaacaacca   1620
tttatgagac cagtacaaac tactcaagag gaagatggct gtagctgccg atttccagaa   1680
gaagaagaag gaggatgtga actgagagtg aagttcagca ggagcgcaga cgcccccgcg   1740
tacaagcagg gccagaacca gctctataac gagctcaatc taggacgaag agaggagtac   1800
gatgttttgg acaagagacg tggccgggac cctgagatgg ggggaaagcc gagaaggaag   1860
aaccctcagg aaggcctgta caatgaactg cagaaagata gatggcggaa ggcctacagt   1920
gagattggga tgaaaggcga gcgccggagg ggcaaggggc acgatggcct ttaccagggt   1980
ctcagtacag ccaccaagga cacctacgac gcccttcaca tgcaggccct gccccctcgc   2040
taa                                                                 2043
```

<210> SEQ ID NO 28
<211> LENGTH: 2064
<212> TYPE: DNA
<213> ORGANISM: Artificial Sequence
<220> FEATURE:
<223> OTHER INFORMATION: Nucleic acid sequence encoding CAR-SCA having SCA sequence based on antibody sequence against HIV.

<400> SEQUENCE: 28

```
atgctgctgc tggtgacaag cctgctgctg tgcgagctgc cccaccccgc ctttctgctg     60
atcccccagc cccagctgca ggaatctggc cctggcctgg tggaagccag cgagacactg    120
agcctgacct gcaccgtgtc cggcgatagc accgccgcct gcgactactt ttggggctgg    180
gtgcgccagc ctcctggcaa gggactggaa tggatcggcg gcctgagcca ctgcgccggc    240
tactacaaca ccggctggac ctaccacaac cccagcctca agtcccggct gaccatcagc    300
ctggacaccc ccaagaacca ggtgttcctg aagctgaaca gcgtgacagc cgccgacacc    360
gccatctact actgcgccag attcgacggc gaggtgctgg tgtaccacga ctggcccaag    420
cccgcctggg tggacctgtg ggcagaggc acactggtga cagtgaccgt gtctagcggc     480
ggaggcggaa gcggaggtgg aggatctggc ggcggaggaa gccagtctgc cctgacacag    540
cctcccagcg cctctggcag ccctggccag agcatcagca tcagctgcac cggcaccagc    600
aacagattcg tgtcctggta tcagcagcac cccggcaagg cccccaagct ggtgatctac    660
ggcgtgaaca agcggcccag cggcgtgccc gatcggttca gcggcagcaa gagcggcaac    720
accgccagcc tgacagtgtc cggcctgcag accgacgacg aggccgtgta ctactgcagc    780
agcctcgtgg gaaactggga cgtgatcttc ggcggaggca ccaagctgac cgtgctggag    840
agcaaatacg ggcccccctg cccccttgc cctgcccccg agttcctggg cggacccagc     900
gtgttcctgt tccccccaa gcccaaggac accctgatga tcagccggac ccccgaggtg     960
acctgtgtgg tggtggacgt gtcccaggag gaccccgagg tccagttcaa ctggtacgtg   1020
gacggcgtgg aggtgcacaa cgccaagacc aagccccggg aggagcagtt caatagcacc   1080
taccgggtgg tgtccgtgct gaccgtgctg caccaggact ggctgaacgg caaggaatac   1140
aagtgtaagg tgtccaacaa gggcctgccc agcagcatcg agaaaaccat cagcaaggcc   1200
aagggccagc ctcgggagcc ccaggtgtac accctgcccc ctagccaaga ggagatgacc   1260
aagaaccagg tgtccctgac ctgcctggtg aagggcttct accccagcga catcgccgtg   1320
gagtgggaga gcaacggcca gcccgagaac aactacaaga ccacccccc tgtgctggac    1380 agcgacggca gcttcttcct gtacagccgg ctgaccgtgg acaagagccg gtggcaggag   1440
ggcaacgtct ttagctgctc cgtgatgcac gaggccctgc acaaccacta cacccagaag   1500
agcctgagcc tgtccctggg caaggatatc tacatctggg cgcccttggc cgggacttgt   1560
ggggtccttc tcctgtcact ggttatcacc ctttactgca aacggggcag aaagaaactc   1620
ctgtatatat tcaaacaacc atttatgaga ccagtacaaa ctactcaaga ggaagatggc   1680
tgtagctgcc gatttccaga agaagaagaa ggaggatgtg aactgagagt gaagttcagc   1740
aggagcgcag acgcccccgc gtacaagcag ggccagaacc agctctataa cgagctcaat   1800
ctaggacgaa gagaggagta cgatgttttg gacaagagac gtggccggga ccctgagatg   1860
gggggaaagc cgagaaggaa gaaccctcag gaaggcctgt acaatgaact gcagaaagat   1920
aagatggcgg aggcctacag tgagattggg atgaaaggcg agcgccggag gggcaagggg   1980
cacgatggcc tttaccaggg tctcagtaca gccaccaagg acacctacga cgcccttcac   2040
atgcaggccc tgccccctcg ctaa                                          2064
```

<210> SEQ ID NO 29
<211> LENGTH: 2058
<212> TYPE: DNA
<213> ORGANISM: Artificial Sequence
<220> FEATURE:
<223> OTHER INFORMATION: Nucleic acid sequence encoding CAR-SCA having SCA sequence based on antibody sequence against HIV.

<400> SEQUENCE: 29

```
atgctgctgc tggtgacaag cctgctgctg tgcgagctgc cccaccccgc ctttctgctg      60
atcccccagc ctcagctgca ggaaagcggc cctacactgg tggaagccag cgagacactg     120
agcctgacct gcgccgtgtc cggcgatagc accgccgcct gcaatagctt ctggggctgg     180
gtccgccagc cccctggcaa gggactggaa tgggtgggaa gcctgagcca ctgcgccagc     240
tactggaacc ggggctggac ctaccacaac cccagcctga agtcccggct gaccctggcc     300
ctggacaccc ccaagaacct ggtgttcctg aagctgaaca gcgtgacagc cgccgacacc     360
gccacctact actgcgccag attcggcggc gaggtgctgc ggtacaccga ctggcctaag     420
cccgcctggg tggacctgtg ggcagaggc accctggtga cagtgagtag cggcggaggc      480
ggaagcggtg gagggggatc tggcggcgga ggaagccagt ctgccctgac acagcctccc     540
agcgcctctg gcagccctgg ccagagcatc accatcagct gcaccggcac cagcaacaac     600
ttcgtgtcct ggtatcagca gcacgccggc aaggccccca agctggtgat ctacgacgtg     660
aacaagcggc ccagcggcgt gcccgacaga ttcagcggca gcaagagcgg caacaccgcc     720
agcctgaccg tgtctggcct gcagaccgac gacgaggccg tgtactactg cggcagcctc     780
gtgggaaact gggacgtgat cttcggcgga ggcaccaagc tgaccgtgct ggagagcaaa     840
tacgggcccc cctgcccccc ttgccctgcc cccgagttcc tgggcggacc cagcgtgttc     900
ctgttccccc ccaagcccaa ggacaccctg atgatcagcc ggacccccga ggtgacctgt     960
gtggtggtgg acgtgtccca ggaggacccc gaggtccagt tcaactggta cgtggacggc    1020
gtggaggtgc acaacgccaa gaccaagccc cgggaggagc agttcaatag cacctaccgg    1080
gtggtgtccg tgctgaccgt gctgcaccag gactggctga acggcaagga atacaagtgt    1140
aaggtgtcca acaagggcct gcccagcagc atcgagaaaa ccatcagcaa ggccaagggc    1200
cagcctcggg agccccaggt gtacaccctg ccccctagcc aagaggagat gaccaagaac    1260
caggtgtccc tgacctgcct ggtgaagggc ttctacccca gcgacatcgc cgtggagtgg    1320
gagagcaacg gccagcccga gaacaactac aagaccaccc cccctgtgct ggacagcgac    1380
ggcagcttct tcctgtacag ccggctgacc gtggacaaga gccggtggca ggagggcaac    1440
gtctttagct gctccgtgat gcacgaggcc ctgcacaacc actacaccca gaagagcctg    1500
agcctgtccc tgggcaagga tatctacatc tgggcgccct tggccgggac ttgtggggtc    1560
cttctcctgt cactggttat caccctttac tgcaaacggg gcagaaagaa actcctgtat    1620
atattcaaac aaccatttat gagaccagta caaactactc aagaggaaga tggctgtagc    1680
tgccgatttc cagaagaaga agaaggagga tgtgaactga gagtgaagtt cagcaggagc    1740
gcagacgccc ccgcgtacaa gcagggccag aaccagctct ataacgagct caatctagga    1800
cgaagagagg agtacgatgt tttggacaag agacgtggcc gggaccctga gatgggggga    1860
aagccgagaa ggaagaaccc tcaggaaggc ctgtacaatg aactgcagaa agataagatg    1920
gcggaggcct acagtgagat tgggatgaaa ggcgagcgcc ggaggggcaa ggggcacgat    1980
ggcctttacc agggtctcag tacagccacc aaggacacct acgacgccct tcacatgcag    2040
gccctgcccc ctcgctaa                                                  2058
```

-continued

<210> SEQ ID NO 30
<211> LENGTH: 2076
<212> TYPE: DNA
<213> ORGANISM: Artificial Sequence
<220> FEATURE:
<223> OTHER INFORMATION: Nucleic acid sequence encoding CAR-SCA having SCA sequence based on antibody sequence against HIV.

<400> SEQUENCE: 30

```
atgctgctgc tggtgacaag cctgctgctg tgcgagctgc cccaccccgc atttctgctg      60
atccctcagc ggctggtgga aagcggaggc ggagtggtgc agcccgggag cagcctgaga     120
ctgtcttgcg ccgccagcgg cttcgacttc agccggcagg gaatgcactg ggtgcgccag     180
gctccaggcc agggactgga atgggtggcc ttcattaagt acgacggcag cgagaagtac     240
cacgccgaca gcgtgtgggg cagactgagc atcagccggg acaacagcaa ggacaccctg     300
tacctgcaga tgaacagcct gcgggtggaa gataccgcca cctacttttg cgtgcgggaa     360
gccggcggac ccgactaccg gaacggctac aactactacg acttctacga cggctactac     420
aactaccact acatggatgt gtggggcaag ggcaccaccg tgaccgtgtc atctggcggc     480
ggaggatctg gggggaggcgg atcaggcgga ggcggcagcc agtctgctct gacacagcct     540
gccagcgtct ccggcagccc tggccagagc atcaccatca gctgcaacgg caccagcaac     600
gacgtgggcg gctacgagag cgtgtcctgg tatcagcagc accccggcaa ggcccccaag     660
gtggtgatct acgacgtgtc caagcggccc agcggcgtgt ccaaccggtt cagcggcagc     720
aagagcggca acaccgccag cctgaccatc agcggactgc aggccgagga cgagggcgac     780
tactactgca agagcctgac cagcacccgg cggagagtgt tcggcaccgg caccaagctg     840
accgtgctgg agagcaaata cgggccccc tgcccccctt gccctgcccc cgagttcctg     900
ggcggaccca gcgtgttcct gttccccccc aagcccaagg acaccctgat gatcagccgg     960
acccccgagg tgacctgtgt ggtggtggac gtgtcccagg aggaccccga ggtccagttc    1020
aactggtacg tggacggcgt ggaggtgcac aacgccaaga ccaagccccg ggaggagcag    1080
ttcaatagca cctaccgggt ggtgtccgtg ctgaccgtgc tgcaccagga ctggctgaac    1140
ggcaaggaat acaagtgtaa ggtgtccaac aagggcctgc ccagcagcat cgagaaaacc    1200
atcagcaagg ccaagggcca gcctcgggag ccccaggtgt acaccctgcc ccctagccaa    1260
gaggagatga ccaagaacca ggtgtccctg acctgcctgg tgaagggctt ctaccccagc    1320
gacatcgccg tggagtggga gagcaacggc cagcccgaga acaactacaa gaccaccccc    1380
cctgtgctgg acagcgacgg cagcttcttc ctgtacagcc ggctgaccgt ggacaagagc    1440
cggtggcagg agggcaacgt ctttagctgc tccgtgatgc acgaggccct gcacaaccac    1500
tacacccaga agagcctgag cctgtccctg ggcaaggata tctacatctg ggcgcccttg    1560
gccgggactt gtggggtcct tctcctgtca ctggttatca ccctttactg caaacggggc    1620
agaaagaaac tcctgtatat attcaaacaa ccatttatga gaccagtaca aactactcaa    1680
gaggaagatg gctgtagctg ccgatttcca gaagaagaag aaggaggatg tgaactgaga    1740
gtgaagttca gcaggagcgc agacgccccc gcgtacaagc agggccagaa ccagctctat    1800
aacgagctca atctaggacg aagagaggag tacgatgttt tggacaagag acgtggccgg    1860
gaccctgaga tggggggaaa gccgagaagg aagaaccctc aggaaggcct gtacaatgaa    1920
ctgcagaaag ataagatggc ggaggcctac agtgagattg ggatgaaagg cgagcgccgg    1980
aggggcaagg ggcacgatgg cctttaccag ggtctcagta cagccaccaa ggacacctac    2040
gacgcccttc acatgcaggc cctgccccct cgctaa                              2076
```

<210> SEQ ID NO 31
<211> LENGTH: 2058
<212> TYPE: DNA
<213> ORGANISM: Artificial Sequence
<220> FEATURE:
<223> OTHER INFORMATION: Nucleic acid sequence encoding CAR-SCA having SCA sequence based on antibody sequence against HIV.

<400> SEQUENCE: 31

```
atgctgctgc tggtgacaag cctgctgctg tgcgagctgc cccaccccgc ctttctgctg     60
atccccgagg tgcagctggt ggaatctggc ggaggcctgg tgaaacctgg cggcagcctg    120
agactgagct gcagcgccag cggcttcgac ttcgacaacg cctggatgac ctgggtgcgc    180
cagcctcccg gcaagggcct ggaatgggtg ggaagaatca ccggccctgg cgaggggtgg    240
tccgtggatt atgccgcccc tgtggaaggc cggttcacca tcagcagact gaacagcatc    300
aactttctgt acctggaaat gaacaacctg cggatggaag atagcggcct gtacttctgc    360
gcccggaccg gcaagtacta cgacttttgg agcggctacc cccctggcga agagtacttc    420
caggactggg gcagaggcac cctggtgaca gtgtctagcg gaggcggagg ctctggcggc    480
ggaggaagtg gcggaggcgg gagcagctac gagctgaccc aggaaacagg cgtctccgtc    540
gccctcgggc ggaccgtgac catcacctgt agaggcgaca gcctgcggag ccactacgcc    600
agctggtatc agaagaagcc cggccaggcc cccatcctgc tgttctacgg caagaacaac    660
cggcccagcg gcgtgcccga cagattctct ggcagcgcct ccggcaaccg ggccagcctg    720
acaatttctg gggctcaggc cgaggacgac gccgagtact actgcagcag ccgggacaag    780
agcggcagca gactgtctgt gttcggcgga ggcaccaagc tgaccgtgct ggagagcaaa    840
tacgggcccc cctgcccccc ttgccctgcc cccgagttcc tgggcggacc cagcgtgttc    900
ctgttccccc ccaagcccaa ggacaccctg atgatcagcc ggacccccga ggtgacctgt    960
gtggtggtgg acgtgtccca ggaggacccc gaggtccagt tcaactggta cgtggacggc   1020
gtggaggtgc acaacgccaa gaccaagccc cgggaggagc agttcaatag cacctaccgg   1080
gtggtgtccg tgctgaccgt gctgcaccag gactggctga acggcaagga atacaagtgt   1140
aaggtgtcca acaagggcct gcccagcagc atcgagaaaa ccatcagcaa ggccaagggc   1200
cagcctcggg agccccaggt gtacaccctg ccccctagcc aagaggagat gaccaagaac   1260
caggtgtccc tgacctgcct ggtgaagggc ttctacccca gcgacatcgc cgtggagtgg   1320
gagagcaacg gccagcccga gaacaactac aagaccaccc cccctgtgct ggacagcgac   1380
ggcagcttct tcctgtacag ccggctgacc gtggacaaga gccggtggca ggagggcaac   1440
gtctttagct gctccgtgat gcacgaggcc ctgcacaacc actacaccca gaagagcctg   1500
agcctgtccc tgggcaagga tatctacatc tgggcgccct tggccgggac ttgtggggtc   1560
cttctcctgt cactggttat caccctttac tgcaaacggg gcagaaagaa actcctgtat   1620
atattcaaac aaccatttat gagaccagta caaactactc aagaggaaga tggctgtagc   1680
tgccgatttc cagaagaaga agaaggagga tgtgaactga gagtgaagtt cagcaggagc   1740
gcagacgccc ccgcgtacaa gcagggccag aaccagctct ataacgagct caatctagga   1800
cgaagagagg agtacgatgt tttggacaag agacgtggcc gggaccctga gatgggggga   1860
aagccgagaa ggaagaaccc tcaggaaggc ctgtacaatg aactgcagaa agataagatg   1920
gcggaggcct acagtgagat tgggatgaaa ggcgagcgcc ggaggggcaa ggggcacgat   1980
```

```
ggcctttacc agggtctcag tacagccacc aaggacacct acgacgccct tcacatgcag    2040
gccctgcccc ctcgctaa                                                  2058
```